US007838278B2

(12) United States Patent
Fatland-Bloom et al.

(10) Patent No.: US 7,838,278 B2
(45) **Date of Patent: *Nov. 23, 2010**

(54) COMPOSITIONS AND METHODS FOR MANIPULATING CARBON FLUX IN CELLS

(75) Inventors: Beth Fatland-Bloom, Decatur, IL (US); P. John Rayapati, Monticello, IL (US); Nyerhovwo John Tonukari, Delta State (NG)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/409,072

(22) Filed: Mar. 23, 2009
(Under 37 CFR 1.47)

(65) Prior Publication Data

US 2010/0112651 A1 May 6, 2010

Related U.S. Application Data

(63) Continuation-in-part of application No. 12/195,869, filed on Aug. 21, 2008, now Pat. No. 7,566,563, which is a continuation of application No. 11/334,713, filed on Jan. 17, 2006, now Pat. No. 7,435,168.

(60) Provisional application No. 60/643,982, filed on Jan. 14, 2005.

(51) Int. Cl.

| | |
|---|---|
| *C12N 1/20* | (2006.01) |
| *C12N 1/00* | (2006.01) |
| *C12N 15/74* | (2006.01) |
| *C12N 15/76* | (2006.01) |
| *C12N 15/77* | (2006.01) |
| *C12N 15/00* | (2006.01) |
| *C12N 9/00* | (2006.01) |
| *C12N 9/10* | (2006.01) |
| *C12P 19/34* | (2006.01) |
| *C12P 21/06* | (2006.01) |
| *C07H 21/04* | (2006.01) |

(52) U.S. Cl. ............................. 435/252.3; 435/252.32; 435/252.33; 435/252.34; 435/254.21; 435/254.3; 435/254.9; 435/255.2; 435/471; 435/483; 435/486; 435/487; 435/183; 435/193; 536/23.2; 536/24.1

(58) Field of Classification Search .............. 435/252.3, 435/252.32, 252.33, 252.34, 254.21, 254.3, 435/254.9, 255.2, 69.1, 91.1, 320.1, 471, 435/483, 486, 487, 183, 193; 536/23.2, 24.1
See application file for complete search history.

(56) References Cited

U.S. PATENT DOCUMENTS

| | | | | |
|---|---|---|---|---|
| 6,171,833 | B1 | 1/2001 | Sinskey et al. | |
| 6,403,351 | B1 | 6/2002 | Sinskey et al. | |
| 6,884,606 | B2 | 4/2005 | Sinskey et al. | |
| 6,965,021 | B2 | 11/2005 | Hanke et al. | |
| 7,300,777 | B2 | 11/2007 | Hanke et al. | |
| 7,566,563 | B2 * | 7/2009 | Fatland-Bloom et al. | 435/252.3 |

OTHER PUBLICATIONS

Broun et al., Catalytic plasticity of fatty acid modification enzymes underlying chemical diversity of plant lipids. Science, 1998, vol. 282: 1315-1317.*

Devos et al., Practical limits of function prediction. Proteins: Structure, Function, and Genetics. 2000, vol. 41: 98-107.*

Seffernick et al., Melamine deaminase and Atrazine chlorohydrolase: 98 percent identical but functionally different. J. Bacteriol.,2001, vol. 183 (8): 2405-2410.*

Whisstock et al., Prediction of protein function from protein sequence. Q. Rev. Biophysics., 2003, vol. 36 (3): 307-340.*

Witkowski et al., Conversion of b-ketoacyl synthase to a Malonyl Decarboxylase by replacement of the active cysteine with glutamine. Biochemistry, 1999, vol. 38: 11643-11650.*

McKinlay, James B. et al., "Prospects for a bio-based succinate industry", Applied Microbiology. and Biotechnology (2007) 76:727-740.

Stucka, Rolf et al., "DNA sequences in chromosomes II and VII code for pyruvate carboxylase isoenzymes in *Saccharomyces cerevisiae*: analysis of pyruvate carboxylase-deficient strains", Molecular Genetics & Genomics (1991) 229:307-315.

Potera, Carol, "Making Succinate More Successful", Environmental Health Perspectives, vol. 113, No. 12, Dec. 2005, A832-A835.

Magnuson, Jon K. et al., "Organic Acid Production by Filamentous Fungi", Pacific Northwest National Laboratory, pp. 307-340, Adv. Fungal Biotechnol., 2004.

Goldberg, Israel et al., Organic acids: old metabolites, new themes, Journal of Chemical Technology and Biotechnology 81:1601-1611 (2006).

Engel, Carol A. et al., "Fumaric acid production by fermentation", Applied Microbiology and Biotechnology (2008) 78:379-389.

* cited by examiner

*Primary Examiner*—Ganapathirama Raghu

(57) ABSTRACT

Nucleotide and protein sequences that encode enzymes that change carbon flux through metabolic pathways that lead to lactic acid or fumarate production in a host cell, such as a *R. oryzae* cell, are provided. Methods of manipulating carbon flux in a cell also are provided.

7 Claims, 30 Drawing Sheets

FIG. 2

1 gaattctata ataaacagcg atatcaagac agatcaaaac tcctggacga cttgaatcac 61 aaacatactc ttggaaacat gcatcatact aatgcatgct gaaaggcact tcagtagttc 121 aaaagatatt tgttaccgcc actcattaaa ttaaatttcg accaaaacga tgctaaaaaa 181 atttttatct tttgttcctg aaaatttttt aaaggtaacc aatagcagac tattccgaaa 241 ttgaattgac tagagaaaaa caacctttat gacagcaaca aagtagctta taaccaagtc 301 gtgtgttatt tgagtataaa aacaattttt ttttccatat tggttttcta aaccatagtt 361 ctcattcgtt acaaggataa agactacttt ggcggagtaa aaagaaaaaa gcaaaacaga 421 gagtctccga ataaaataga agcatttcga aaaaagtttg cttcacttaa aataacagta 481 aacgtaaagc aaacattgtg gctgtcatac attgctcatt ttaggatcca tttccactgt 541 gagaatggac aagaaagaaa aaggtaaaag aacaacaaag agtaactcct aaagtaaaac 601 ttttgttgtg caacccaatc aagtcatgcc gttgtgacca tttccgcggt ggcttttcac 661 gcggaacaag aaaaaaaaat tttaaaacga gaaatttttt tgttattgtt tgttttctct 721 tttttctgtt actttataaa cttcctcaag taaggatact cactacgcca tccaacatgt 781 actaattcta ttcatcatag ccatgggtaa agataagact aacatcagta ttgttgtcat 841 cggtcacgtc gattccggta agtcta

FIG. 3

1 tccatttcca ctgtgagaat ggacaagaaa gaaaaaaata aaagaacaac aaagagtaac 61 tcctaaagta aaacttttgt tgtgcaaccc aatcaagtca tgccgttgtg accatttccg 121 cggtggcttt tcacgcggaa caagaaaaaa aaattttaaa acgagaaatt tttttgttat 181 tgtttgtttt ctcttttttc tgttacttta taaacttcct caagtaagga tactcactac 241 gccatccaac atgtactaat tctattcatc atagccatgg gtaaagataa gactaacatc 301 agtattgttg tcatcggtca cgtcgattcc ggtaagtcta

FIG. 4

1 AGCTTGAATG TGTTAGCATG GAATAATGAA ATATGACTTT AGTCCTATTT TCGTTGGTTT

61 AGGTACTTCA GTAATGATGA ATAGAAACGG TTAGGGGCAT TTGTATTTGG TCGCTAGAGG

121 TGAAATTCTT GGATTGACCG AAGACAAACT ACTGCGAAAG CATTTGACCC GGGACGTTTT

181 CATTGATCAA GGTCTAAAGT TAAGGGATCG AAGACGATTA GATACCGTCG TAGTCTTAAC

241 CACAAACTAT GCCGACTAGA GATTGGGCGT GTTTATTATG ACTCGCTCAG CATCTTAGCG

301 AAAGTAAAGT TTTTGGGTTC TGGGGGGAGT ATGGGACGCA AGGCTGAAAC TTAAAGGAAT

361 TGACGGAAGG GCACCACCAG GAGTGGAGCC TGCGGCTTAA TTTGACTCAA CACGGGGAAA

421 CTCACCAGGT CCAGACATAG TAAGGATTGA CAGATTGAAA GCTCTTTCTA GATTCTATGG

481 GTGGTGGTGC ATGGCCGTTC TTAGTTCGTG GAGTGATTTG TCTGGTTAAT TCCCGATAAC

541 GAACGAGACC TTATTCTGCT AATTAGACAG GCTAACTCTT TCGGGTTGGT TTATATTTAA

601 TATTTAACTG GCTTCTTAAA GAAACTATCG GCTTCNAGCC GAAGGAAGTT TTAGGCAATA

661 ACAGGTCTGT GATGCCCTTA GATGTTCTGG GCCGCACGCG CGCTACACTG ATGAAGTCAG

721 CGAGTTTATA ACCTTGGCCG GAAGGTCTGG GTAAACTTTT GAAACTTCAT CGTGCTGGGG

781 ATAGAGCATT GTAATTATTG CTCTTCAACG AGGAATTCCT AGTAAGCGCA AGTCATCAGC

841 TTGCGTTGAT TACGTCCCCT GCCCTTTGTA CACACCGCCC GTCGCTACTA CCGATTGAAT

901 GGTTATAGTG AGCATATGGG ATCAGTAGGA TTTGACTGGC AACAGTCATT TCCTGCAGAG

961 AACTATGGCA AACTAGGCTA TTTAGAGGAA GTAAAAGTCG TAACAAGGTT TCCGTAGGTG

1021 AACCTGCGGA AGG

FIG. 5A

Pyruvate dehydrogenase from Rhizopus oryzae

```
PDH E1B RO g    1 gaaaccctatctttctcaacagacgatgaccttccttacagctattcaccgtatggctcc
PDH E1B RO c    1 gaaaccctatctttctcaacagacgatgaccttccttacagctattcaccgtatggctcc

PDH E1B RO g   61 tgctgccattaagcaggctgctactgcctctgttaagcccactgctgttgctttcactca
PDH E1B RO c   61 tgctgccattaagcaggctgctactgcctctgttaagcccactgctgttgctttcactca

PDH E1B RO g  121 aaagcgtttcaactccactggctctgaggtatagaaaaaaaaaaaatagataatgtaaa
PDH E1B RO c  121 aaagcgtttcaactccactggctctg----------------------------------

PDH E1B RO g  181 cttatatcccccggcttttagatgactgttcgtgaagctttaaaccaagctttggaagaa
PDH E1B RO c  147 -------------------agatgactgttcgtgaagctttaaaccaagctttggaagaa

PDH E1B RO g  241 gaaatgatcaaggatgaaacagtctacatcctcggtgaagaagttgctcaatacaacggt
PDH E1B RO c  188 gaaatgatcaaggatgaaacagtctacatcctcggtgaagaagttgctcaatacaacggt

PDH E1B RO g  301 gcttataaggtattttatcgcgtattttatttgtaggggtattatgggattattcgggaa
PDH E1B RO c  248 gcttata-----------------------------------------------------

PDH E1B RO g  361 aaagcgaaaaaagattggggtgacgaaaagggaggagtttaaaaagaaaactttttaat
PDH E1B RO c  255 ------------------------------------------------------------

PDH E1B RO g  421 ttttttccattgcctaggtgaccaaaggtttattagacaagtttggtgctaagcgtgtg
PDH E1B RO c  255 ----------------aggtgaccaaaggtttattagacaagtttggtgctaagcgtgtg

PDH E1B RO g  481 atcgatacccccattaccgaaatgggttttgctggtattgctgttggttctgccttcagc
PDH E1B RO c  299 atcgatacccccattaccgaaatgggttttgctggtattgctgttggttctgccttcagc
```

FIG. 5B

PDH E1B RO g 541 ggtttgaagcctgtttgtgaattcatgactttcaattttgccatgcaggtaaatacagaa

PDH E1B RO c 359 ggtttgaagcctgtttgtgaattcatgactttcaattttgccatgc--------------

PDH E1B RO g 601 attttttcactaaaaaaatatattcacagtgtttgtattaggctattgatcaaatcgtta

PDH E1B RO c 405 --------------------------------------aggctattgatcaaatcgtta

PDH E1B RO g 661 actctgctgccaagacctactacatgtctggtggtggtgtcaagtgtcctatcgttttcc

PDH E1B RO c 426 actctgctgccaagacctactacatgtctggtggtggtgtcaagtgtcctatcgttttcc

PDH E1B RO g 721 gtggcctaccgtgctgctgctggtgtccggccccaacctctcaagattctctgcctggat

PDH E1B RO c 486 gtggcctaccgtgctgctgctggtgtccggccccaacctctcaagattctctgcctggat

PDH E1B RO g 781 gggtctgttcccgcttgaaggtcccttttcctggaccccttgaagatgctaaggttgttga

PDH E1B RO c 546 gggtctgttcccgcttgaaggtcccttttcctggaccccttgaagatgctaaggttgttga

PDH E1B RO g 841 aggctgccattcgtgaccccaaccctgttgtcttccttgaaaacgaactcgaatatggtg

PDH E1B RO c 606 aggctgccattcgtgaccccaaccctgttgtcttccttgaaaacgaactcgaatatggtg

PDH E1B RO g 901 tctcttaccctgtctcttccgaagctctttcttctgactttgttctccctatcggtaagg

PDH E1B RO c 666 tctcttaccctgtctcttccgaagctctttcttctgactttgttctccctatcggtaagg

PDH E1B RO g 961 ccaagattgaacgtgaaggtaaggatgtgactatcgtttcccactctcgtcctgttggtt

PDH E1B RO c 726 ccaagattgaacgtgaaggtaaggatgtgactatcgtttcccactctcgtcctgttggtt

PDH E1B RO g 1021 tcgccatgaaggccgctgaacttttggccaaggatggtatttctgctgaagttatcaact

PDH E1B RO c 786 tcgccatgaaggccgctgaacttttggccaaggatggtatttctgctgaagttatcaact

FIG. 5C

PDH E1B RO g 1081 tgagatctatcaagcctcttgatgttgacactatcatcaagtccgtcaagaagaccaacc

PDH E1B RO c 846 tgagatctatcaagcctcttgatgttgacactatcatcaagtccgtcaagaagaccaacc

PDH E1B RO g 1141 accttatctctgttgaaaacgcctgggcctctttcggtgtcggttctgaaattgctgctc

PDH E1B RO c 906 accttatctctgttgaaaacgcctgggcctctttcggtgtcggttctgaaattgctgctc

PDH E1B RO g 1201 aagttatggaaagtaagtagtatagatttaaaaagatgcatttgtacaagtatagatgtt

PDH E1B RO c 966 aagttatggaaa------------------------------------------------

PDH E1B RO g 1261 aatttctgttaaaaggtgaggctttctggcacttggatgctcctatgagccgtgtcactg

PDH E1B RO c 978 ---------------gtgaggctttctggcacttggatgctcctatgagccgtgtcactg

PDH E1B RO g 1321 gtgctgatgttcccactccctatgctgccaaccttgaagcccttgctttccctgatgaac

PDH E1B RO c 1023 gtgctgatgttcccactccctatgctgccaaccttgaagcccttgctttccctgatgaac

PDH E1B RO g 1381 acgtcattgctaaggctgttagagataacttggacaaaaaagttggtttctaaaaaggat

PDH E1B RO c 1083 acgtcattgctaaggctgttagagataacttggacaaaaaagttggtttctaaaaaggat

PDH E1B RO g 1441 tataatttttactattccaataatatttgttttttcttctactttttccctctctct

PDH E1B RO c 1143 tataatttttactattccaataatatttgttttttcttctactttttccctctctct

PDH E1B RO g 1501 acacacatctttttcttttatagattggagatcaagaaaaaaaaaaccagcaaaatcaaa

PDH E1B RO c 1203 acacacatctttttcttttatagattggagatcaagaaaaaaaaaaccagcaaaatcaaa

PDH E1B RO g 1561 agaagtatttgatgt--------------------------

PDH E1B RO c 1263 agaagtatttgatgtaaaaaaaaaaaaaaaaaaaaaaaaaa

FIG. 6A

*Rhizopus oryzae* pyruvate carboxylase gene cDNA

GGACACTGACATGGACTGAACGAGTAGAAACGACTGGAGCTTTTGGACACTGACATGGAC 60

TGAAGGAGTAGAAACGACTGGAGCACGAGGACACTGACATGGACTGAAGGAGTAGAAAAT 120

TTCTTTCTTGTATTTTTTTTAAACACACACACACTTAAATAATAACGATGCCTGCTGCA 180

CCAGTACGTGAACATTCAGTGGATACCATTCGCAGAAATAGCGAAGTGATGGGTAACCTG 240

AGAAAATTGATGGTGGTTAATCGTGGTGAAATTGCTATACGTGTCTTTCGTACAGCTCAT 300

GAACTCTCTATGAAGACAGTAGCTATTTTCTCTCATGAAGATAGATTATCTATGCACAGA 360

TATAAGGCTGATGAATCCTATCAACTCGGTCGTATTGGTCAATACACACCTGTAGGTGAT 420

TATTTGGCACAAGATGAAGTCGTTCGAATCGCAAAGGAACGTGGTGTTAGCATGATTCAT 480

CCTGGTTATGGTTTCTTATCTGAAAATGCTGAATTCGCTCGCAAGGTGGAAGCTGCAGGA 540

GTCACTTTCATTGGTCCCTCTCCTGATGTCATTGAAAGTTTAGGCGATAAAACAAAAGCC 600

AGAACGATTGCCATGCAGTGTGAAGTCCCTGTTGTCCCTGGTACACCTGGACCAGTCAGT 660

GAATATAAAGAGGCCCTGAACTTTATCAAAGAATATGGTTTTCCTATTATCATCAAGGCT 720

GCCATGGGTGGTGGTGGTCGTGGTATGCGTGTGGTTCGTGACGAAGCCAGTCTAGAGGAC 780

GCGTTTACCCGTGCGAAATCTGAAGCTTTAGCTGCCTTTGGTGATGGTACTGTCTTCATC 840

GAACGTTTCCTTGATAAGCCTCGTCATATTGAGGTTCAATTGTTGGCAGATCGTGCAGGT 900

AACGTAGTCCATCTCTTTGAACGTGATTGGTCTGTGCAACGTCGTCACCAAAAGGTCGTA 960

AAAATTGCACCTGCCAAAAACTTGGATAACAAGGTACGTGAGGCCATCTTGAACGATGCG 1020

ATCAAGATTGCCAAGGCTGTAAAGTACAAGAACGCTGGTACTGCAGAATTCTTGGTTGAT 1080

AACCAAAACCGTCACTACTTTATCGAAATCAATCCTCGTATCCAAGTCGAACACACCATC 1140

ACAGAAGAAATCACAGGTATCGATATCGTTGCCGCTCAAATTCAGATCGCTGCTGGTGCC 1200

FIG. 6B

CTCTTGCCTCAATTGGGTCTTACCCAACAACGTATCCGTCAACGTGGGTTCGCGATCCAG 1260

TGTCGTGTGACAACCGAGGACCCCGAAAAGAATTTCCAGCCTGACACGGGTAAGATCGAA 1320

GTTTACCGTTCCTCTGGTGGTAACGGTGTTCGTCTGGATGGTGGTGCTGGTTACGCAGGT 1380

GCTATCATTACCCCTCATTATGATTCACTTTTGGTCAAAGTCTCTTGTTCTGGATCCACC 1440

TACGAAGTCGCTCGTCGAAAGATCGTTCGTGCCTTGGTCGAATTCAGAATTCGTGGCGTC 1500

AAGACCAATATCCCCTTCTTACAACGTCTCTTGACCCATGATACTTTCATCAACGGTAAC 1560

TGCTGGACAACTTTCATTGATGATACTCCCGATCTTTTCCGTCTTGTTCAATTCCAAAAC 1620

CGTGCTCAAAGACTTTTGGGTTACCTTGGTGATGTCGTCGTCAATGGTTCTCAAATCAAG 1680

GGTCAAATGGGTGATCCTATTCTGAACAAGAGATCGAAATTCCTGTTGCGTGAAAGTGGC 1740

AGCGACAAGACGGTCGATGTCTCTGCTCCTGCTACTGAAGGCTGGAGAAAGATCATTGTG 1800

GAACAAGGACCTGAAGCTTTCGCAAAAGCTGTCCGTGCTTACCCTGGTGTCTTGATCACC 1860

GATACCACCTGGAGAGACGCTCATCAGAGTTTATTGGCCACTCGTGTGAGAACCGTCGAT 1920

CTCTTACGTATCGCACCTGCTACCTCTCATGCTTTGGCCAACGCCTTTTCATTGGAATGT 1980

TGGGGAGGTGCTACCTTTGACGTTGCTATGCGTTTCCTTCATGAAGATCCTTGGGACCGT 2040

CTTGCTGCTTTGCGAAAGTTGGTACCCAATGTACCCTTCCAAATGCTTTTGCGTGGTGCC 2100

AATGCGGTAGGTTACACCTCTTACCCTGATAATGTTATCTATGAATTCTGTGACAAGGCA 2160

GTCAAGTGTGGTATGGATGTCTTCCGTATCTTTGATTCTCTCAATTATGTTGAAAACATG 2220

AGATTGGGTATTGACGCTGTCAAGAAGGCCGGTGGTGTTGTTGAAGCCACCATCTGTTAC 2280

ACTGGTGATGTCTCCAACCCTAGCCGCAAGAAGTACGACTTGAAGTACTACCTTGACCTT 2340

ACACAATCCTTGGTTAACGAAGGTATTCACATCTTGGGTATCAAGGACATGGCTGGTCTT 2400

GTCAAACCCCAGGCAGCCAAATTAGTGGTCCCCAGTATCCGTGCCAAGTTCCCTGACTTG 2460

CCCATTCACGTTCACACACACGATACTGCAGGTACTGGTGTTGCTAGCATGATGGCTGCT 2520

GCCGCTGCTGGTGCTGACGTTGTTGATGTTGCCGTTGACGCCATGTCCGGTATGACCTCT 2580

CAACCCGCTATGGGTGCCATTGTCGCTGGACTTGAACAGACCAATTTGGGTACCGGTATC 2640

FIG. 6C

CGCATGGAAGACATTCATGCCATCAATGCTTACTGGGAGCAATGTCGTTTGCTTTACTCT 2700

TGCTTCGAAGCCAACGTGCGTTCAGCCGATTCTGGTGTCTATGAACATGAAATGCCTGGT 2760

GGACAATATACCAACTTGATGTTCCAAGCACAACAACTCGGCTTGGGAACTCAATGGAAG 2820

CAAATCAAGAAGGCTTATAAGGAGGCAAACGAACTCTGTGGTGACTTGGTCAAGGTCACG 2880

CCTTCGTCCAAGGTCGTTGGTGATCTTGCTCAATTCATGGTTTCCAACCAACTTTCTGCC 2940

AAAGAATTTGAAGAACGCGCCTCTAGTCTCTCTCCCTACCTCTGTCATCGAGTTCTTC 3000

CAAGGTTATCTCGGTCAACCCTATGGTGGTTTCCCCGAGCCCTTGCGCTCCAACATCCTT 3060

CGTGATCTACCTCGCCTCGACGGTCGCCCTGGTGCTAGCTTGCCTTCACTTGACATGGCT 3120

AAACTCAAGGAAGAGTTGGTTGAAAAGTACGGTTCAAGTATCCGTGATTACGATGTGATC 3180

TCTGCTGCTCTTTACCCCAAGGTCTTTGCCGAATACCGTGATACCGTCAGTCAATACGGT 3240

GATCTCTCCGTTTTGCCTACACGTTACTTTTTGACTAAGCCTGAGATCAATGAAGAATTC 3300

CATGTTGAGATTGAAGAAGGAAAGACGTTGATTATAAAGTTATTGGCCGTTGGTCCTCTG 3360

AACAATGACGGTAAACGTGATGTTTACTTTGAATTGAACGGTGAAGCTCGTGTAGTGGGT 3420

ATTGTCGATCGCAATTCTGCTATTGAAATCGTCACACGTGAAAAGGCAAATCCCTCTAAC 3480

CCCGGTGACATTGGTGCTCCTATGTCTGGTGTTGTTGTTGAGATCCGTGCCAAGGAAGGT 3540

ACCCATGTTAAGGCTGGCGATCCTCTTGCTGTTCTCTCTGCTATGAAAATGGAAACAGTG 3600

GTCACTGCTCCCGTGGCTGGTAAAGTTGAGCGTGTTCCCATCCAAGAAGGTGATTCGTTA 3660

TCCGCTGGTGATTTGGTGGCTAAGGTTGTCAAAGAGGAAGCCTAAAAAAGGAAATTTCTT 3720

TTTCCCCTCATCTGAATTTTTTTTTTTCTGTAGAATAATAATAAAATAAGCTAAAAAAAT 3780

ACTTTGTTATCTTATCAAAAAAAAAAAAAAAAAAAAAAAAAAAAAA 3826

FIG. 6D

Genomic DNA

GGACACTGACATGGACTGAACGAGTAGAAACGACTGGAGCTTTTGGACACTGACATGGAC 60
TGAAGGAGTAGAAACGACTGGAGCACGAGGACACTGACATGGACTGAAGGAGTAGAAAAT 120
TTCTTTCTTGTATTTTTTTTAAACACACACACACTTAAATAATAACGATGCCTGCTGCA 180
CCAGTACGTGAACATTCAGTGGATACCATTCGCAGAAATAGCGAAGTGATGGGTAACCTG 240
AGAAAATTGATGGTGGTTAATCGTGGTGAAATTGCTATACGTGTCTTTCGTACAGCTCAT 300
GAACTCTCTATGAAGACAGTAGCTATTTTCTCTCATGAAGATAGATTATCTATGCACAGA 360
TATAAGGCTGATGAATCCTATCAACTCGGTCGTATTGGTCAATACACACCTGTAGGTGAT 420
TATTTGGCACAAGATGAAGTCGTTCGAATCGCAAAGGAACGTGGTGTTAGCATGATTCAT 480
CCTGGTTATGGTTTCTTATCTGAAAATGCTGAATTCGCTCGCAAGGTGGAAGCTGCAGGA 540
GTCACTTTCATTGGTCCCTCTCCTGATGTCATTGAAAGTTTAGGCGATAAAACAAAAGCC 600
AGAACGATTGCCATGCAGTGTGAAGTCCCTGTTGTCCCTGGTACACCTGGACCAGTCAGT 660
GAATATAAAGAGGCCCTGAACTTTATCAAAGAATATGGTTTTCCTATTATCATCAAGGCT 720
GCCATGGGTGGTGGTGGTCGTGGTATGCGTGTGGTTCGTGACGAAGCCAGTCTAGAGGAC 780
GCGTTTACCCGTGCGAAATCTGAAGCTTTAGCTGCCTTTGGTGATGGTACTGTCTTCATC 840
GAACGTTTCCTTGATAAGCCTCGTCATATTGAGGTTCAATTGTTGGCAGATCGTGCAGGT 900
AACGTAGTCCATCTCTTTGAACGTGATTGGTCTGTGCAACGTCGTCACCAAAAGGTCGTA 960
AAAATTGCACCTGCCAAAAACTTGGATAACAAGGTACGTGAGGCCATCTTGAACGATGCG 1020
ATCAAGATTGCCAAGGCTGTAAAGTACAAGAACGCTGGTACTGCAGAATTCTTGGTTGAT 1080
AACCAAAACCGTCACTACTTTATCGAAATCAATCCTCGTATCCAAGTCGAACACACCATC 1140
ACAGAAGAAATCACAGGTATCGATATCGTTGCCGCTCAAATTCAGATCGCTGCTGGTGCC 1200
CTCTTGCCTCAATTGGGTCTTACCCAACAACGTATCCGTCAACGTGGGTTCGCGATCCAG 1260
TGTCGTGTGACAACCGAGGACCCCGAAAAGAATTTCCAGCCTGACACGGGTAAGATCGAA 1320

FIG. 6E

GTTTACCGTTCCTCTGGTGGTAACGGTGTTCGTCTGGATGGTGGTGCTGGTTACGCAGGT 1380

GCTATCATTACCCCTCATTATGATTCACTTTTGGTCAAAGTCTCTTGTTCTGGATCCACC 1440

TACGAAGTCGCTCGTCGAAAGATCGTTCGTGCCTTGGTCGAATTCAGAATTCGTGGCGTC 1500

AAGACCAATATCCCCTTCTTACAACGTCTCTTGACCCATGATACTTTCATCAACGGTAAC 1560

TGCTGGACAACTTTCATTGATGATACTCCCGATCTTTTCCGTCTTGTTCAATTCCAAAAC 1620

CGTGCTCAAAGACTTTTGGGTTACCTTGGTGATGTCGTCGTCAATGGTTCTCAAATCAAG 1680

GGTCAAATGGGTGATCCTATTCTGAACAAGAGATCGAAATTCCTGTTGCGTGAAAGTGGC 1740

AGCGACAAGACGGTCGATGTCTCTGCTCCTGCTACTGAAGGCTGGAGAAAGATCATTGTG 1800

GAACAAGGACCTGAAGCTTTCGCAAAAGCTGTCCGTGCTTACCCTGGTGTCTTGATCACC 1860

GATACCACCTGGAGAGACGCTCATCAGAGTTTATTGGCCACTCGTGTGAGAACCGTCG*gt* 1920

*aagttgtaaaaaaaaagtggtatgatttttattgatttttttttttttttgaaaag*A 1980

TCTCTTACGTATCGCACCTGCTACCTCTCATGCTTTGGCCAACGCCTTTTCATTGGAATG 2040

TTGGGGAGGTGCTACCTTTGACGTTGCTATGCGTTTCCTTCATGAAGATCCTTGGGACCG 2100

TCTTGCTGCTTTGCGAAAGTTGGTACCCAATGTACCCTTCCAAATGCTTTTGCGTGGTGC 2160

CAATGCGGTAGGTTACACCTCTTACCCTGATAATGTTATCTATGAATTCTGTGACAAGGC 2220

AGTCAAGTGTGGTATGGATGTCTTCCGTATCTTTGATTCTCTCAATTATGTTGAAAACAT 2280

GAGATTGGGTATTGACGCTGTCAAGAAGGCCGGTGGTGTTGTTGAAGCCACCATCTGTTA 2340

CACTGGTGATGTCTCCAACCCTAGCCGCAAGAAGTACGACTTGAAGTACTACCTTGACCT 2400

TACACAATCCTTGGTTAACGAAGGTATTCACATCTTGGGTATCAAGGACATGGCTGGTCT 2460

TGTCAAACCCCAGGCAGCCAAATTAGTGGTCCCCAGTATCCGTGCCAAGTTCCCTGACTT 2520

GCCCATTCACGTTCACACACACGATACTGCAGGTACTGGTGTTGCTAGCATGATGGCTGC 2580

TGCCGCTGCTGGTGCTGACGTTGTTGATGTTGCCGTTGACGCCATGTCCGGTATGACCTC 2640

TCAACCCGCTATGGGTGCCATTGTCGCTGGACTTGAACAGACCAATTTGGGTACCGGTAT 2700

CCGCATGGAAGACATTCATGCCATCAATGCTTACTGGGAGCAATGTCGTTTGCTTTACTC 2760

FIG. 6F

TTGCTTCGAAGCCAACGTGCGTTCAGCCGATTCTGGTGTCTATGAACATGAAATGCCTGG 2820

TGGACAATATACCAACTTGATGTTCCAAGCACAACAACTCGGCTTGGGAACTCAATGGAA 2880

GCAAATCAAGAAGGCTTATAAGGAGGCAAACGAACTCTGTGGTGACTTGGTCAAGGTCAC 2940

GCCTTCGTCCAAGGTCGTTGGTGATCTTGCTCAATTCATGGTTTCCAACCAACTTTCTGC 3000

CAAAGAATTTGAAGAACGCGCCTCTAGTCTCTCTCCCTACCTCTGTCATCGAGTTCTT 3060

CCAAGGTTATCTCGGTCAACCCTATGGTGGTTTCCCCGAGCCCTTGCGCTCCAACATCCT 3120

TCGTGATCTACCTCGCCTCGACGGTCGCCCTGGTGCTAGCTTGCCTTCACTTGACATGGC 3180

TAAACTCAAGGAAGAGTTGGTTGAAAAGTACGGTTCAAGTATCCGTGATTACGATGTGAT 3240

CTCTGCTGCTCTTTACCCCAAGGTCTTTGCCGAATACCGTGATACCGTCAGTCAATACGG 3300

TGATCTCTCCGTTTTGCCTACACGTTACTTTTTGACTAAGCCTGAGATCAATGAAGAATT 3360

CCATGTTGAGATTGAAGAAGGAAAGACGTTGATTATAAAGTTATTGGCCGTTGGTCCTCT 3420

GAACAATGACGGTAAACGTGATGTTTACTTTGAATTGAACGGTGAAGCTCGTGTAGTGGG 3480

TATTGTCGATCGCAATTCTGCTATTGAAATCGTCACACGTGAAAAGGCAAATCCCTCTAA 3540

CCCCGGTGACATTGGTGCTCCTATGTCTGGTGTTGTTGTTGAGATCCGTGCCAAGGAAGG 3600

TACCCATGTTAAGGCTGGCGATCCTCTTGCTGTTCTCTCTGCTATGAAAATGGAAACAGT 3660

GGTCACTGCTCCCGTGGCTGGTAAAGTTGAGCGTGTTCCCATCCAAGAAGGTGATTCGTT 3720

ATCCGCTGGTGATTTGGTGGCTAAGGTTGTCAAAGAGGAAGCCTAAAAAAGGAAATTTCT 3780

TTTTCCCCTCATCTGAATTTTTTTTTTTCTGTAGAATAATAATAAAATAAGCTAAAAAAA 3840

TACTTTGTTATCTTATC 3857

FIG. 6G

Protein

MPAAPVREHSVDTIRRNSEVMGNLRKLMVVNRGEIAIRVF 40

RTAHELSMKTVAIFSHEDRLSMHRYKADESYQLGRIGQYT 80

PVGDYLAQDEVVRIAKERGVSMIHPGYGFLSENAEFARKV 120

EAAGVTFIGPSPDVIESLGDKTKARTIAMQCEVPVVPGTP 160

GPVSEYKEALNFIKEYGFPIIIKAAMGGGGRGMRVVRDEA 200

SLEDAFTRAKSEALAAFGDGTVFIERFLDKPRHIEVQLLA 240

DRAGNVVHLFERDWSVQRRHQKVVKIAPAKNLDNKVREAI 280

LNDAIKIAKAVKYKNAGTAEFLVDNQNRHYFIEINPRIQV 320

EHTITEEITGIDIVAAQIQIAAGALLPQLGLTQQRIRQRG 360

FAIQCRVTTEDPEKNFQPDTGKIEVYRSSGGNGVRLDGGA 400

GYAGAIITPHYDSLLVKVSCSGSTYEVARRKIVRALVEFR 440

IRGVKTNIPFLQRLLTHDTFINGNCWTTFIDDTPDLFRLV 480

QFQNRAQRLLGYLGDVVVNGSQIKGQMGDPILNKRSKFLL 520

RESGSDKTVDVSAPATEGWRKIIVEQGPEAFAKAVRAYPG 560

VLITDTTWRDAHQSLLATRVRTVDLLRIAPATSHALANAF 600

SLECWGGATFDVAMRFLHEDPWDRLAALRKLVPNVPFQML 640

LRGANAVGYTSYPDNVIYEFCDKAVKCGMDVFRIFDSLNY 680

VENMRLGIDAVKKAGGVVEATICYTGDVSNPSRKKYDLKY 720

YLDLTQSLVNEGIHILGIKDMAGLVKPQAAKLVVPSIRAK 760

FPDLPIHVHTHDTAGTGVASMMAAAAGADVVDVAVDAMS 800

GMTSQPAMGAIVAGLEQTNLGTGIRMEDIHAINAYWEQCR 840

LLYSCFEANVRSADSGVYEHEMPGGQYTNLMFQAQQLGLG 880

TQWKQIKKAYKEANELCGDLVKVTPSSKVVGDLAQFMVSN 920

FIG. 6H

QLSAKEFEERASSLSLPTSVIEFFQGYLGQPYGGFPEPLR 960

SNILRDLPRLDGRPGASLPSLDMAKLKEELVEKYGSSIRD 1000

YDVISAALYPKVFAEYRDTVSQYGDLSVLPTRYFLTKPEI 1040

NEEFHVEIEEGKTLIIKLLAVGPLNNDGKRDVYFELNGEA 1080

RVVGIVDRNSAIEIVTREKANPSNPGDIGAPMSGVVVEIR 1120

AKEGTHVKAGDPLAVLSAMKMETVVTAPVAGKVERVPIQE 1160

GDSLSAGDLVAKVVKEEA 1178

FIG. 7A

*Medicago sativa* – PEP carboxylase atg gca aac aag atg gaa aaa atg gca tca att gat gca cag ctt aga 48

Met Ala Asn Lys Met Glu Lys Met Ala Ser Ile Asp Ala Gln Leu Arg 1 5 10 15 caa ttg gtt cct gca aaa gtg agt gaa gat gat aaa ctt att gag tat 96

Gln Leu Val Pro Ala Lys Val Ser Glu Asp Asp Lys Leu Ile Glu Tyr 20 25 30 gat gct ttg ttg ttg gat cgg ttt ctt gat att ctt caa gat tta cat 144

Asp Ala Leu Leu Leu Asp Arg Phe Leu Asp Ile Leu Gln Asp Leu His 35 40 45 gga gag gat ctg aag gat tct gtt caa gaa gtg tat gaa ctg tct gct 192

Gly Glu Asp Leu Lys Asp Ser Val Gln Glu Val Tyr Glu Leu Ser Ala 50 55 60 gaa tat gaa aga aag cat gat cct aag aaa ctt gaa gag ctt gga aat 240

Glu Tyr Glu Arg Lys His Asp Pro Lys Lys Leu Glu Glu Leu Gly Asn 65 70 75 80 ttg atc aca agt ttc gat gca ggt gac tca att gtt gtt gcc aag tcc 288

Leu Ile Thr Ser Phe Asp Ala Gly Asp Ser Ile Val Val Ala Lys Ser 85 90 95 ttt tca cac atg ctt aac ttg gcc aac tta gct gaa gag gtt caa att 336

Phe Ser His Met Leu Asn Leu Ala Asn Leu Ala Glu Glu Val Gln Ile 100 105 110

FIG. 7B gcg cac cgc cga agg aac aag ttg aag aaa ggt gat ttt agg gat gag 384

Ala His Arg Arg Arg Asn Lys Leu Lys Lys Gly Asp Phe Arg Asp Glu 115 120 125 agc aat gca acc act gaa tct gac att gag gaa act ctc aag aaa ctt 432

Ser Asn Ala Thr Thr Glu Ser Asp Ile Glu Glu Thr Leu Lys Lys Leu 130 135 140 gtg ttt gac atg aag aaa tct cct caa gag gtt ttt gat gca ttg aag 480

Val Phe Asp Met Lys Lys Ser Pro Gln Glu Val Phe Asp Ala Leu Lys 145 150 155 160 aac cag act gtt gat ctt gtt ctt act gct cat cct act cag tcg gtt 528

Asn Gln Thr Val Asp Leu Val Leu Thr Ala His Pro Thr Gln Ser Val 165 170 175 cgt cga tct ttg ctt caa aag cac gga agg gta agg aac tgt tta tct 576

Arg Arg Ser Leu Leu Gln Lys His Gly Arg Val Arg Asn Cys Leu Ser 180 185 190 caa ttg tat gct aaa gac atc act cct gat gat aag cag gag ctt gat 624

Gln Leu Tyr Ala Lys Asp Ile Thr Pro Asp Asp Lys Gln Glu Leu Asp 195 200 205 gaa gct ctc cag agg gag att caa gct gca ttc cgt act gac gaa atc 672

Glu Ala Leu Gln Arg Glu Ile Gln Ala Ala Phe Arg Thr Asp Glu Ile 210 215 220 aag agg act cca cca act ccc caa gat gaa atg aga gct ggg atg agt 720

Lys Arg Thr Pro Pro Thr Pro Gln Asp Glu Met Arg Ala Gly Met Ser 225 230 235 240

FIG. 7C tac ttc cat gaa aca att tgg aag ggt gtc cct aaa ttt ctt cgc cgt 768

Tyr Phe His Glu Thr Ile Trp Lys Gly Val Pro Lys Phe Leu Arg Arg 245 250 255 gtt gat acg gca ttg aag aac ata ggg att aac gaa cgt gtt ccc tat 816

Val Asp Thr Ala Leu Lys Asn Ile Gly Ile Asn Glu Arg Val Pro Tyr 260 265 270 aat gct cct ctt att caa ttt tct tct tgg atg ggt ggt gat cgt gac 864

Asn Ala Pro Leu Ile Gln Phe Ser Ser Trp Met Gly Gly Asp Arg Asp 275 280 285 ggt aat cca aga gtg act cct gaa gtg aca agg gat gtt tgc tta cta 912

Gly Asn Pro Arg Val Thr Pro Glu Val Thr Arg Asp Val Cys Leu Leu 290 295 300 gct aga atg atg gct gct aac ttg tat tat tca cag ata gaa gat ctt 960

Ala Arg Met Met Ala Ala Asn Leu Tyr Tyr Ser Gln Ile Glu Asp Leu 305 310 315 320 atg ttt gaa ctt tct atg tgg cgt tgc aat gac gag cta cgt gtt cgc 1008

Met Phe Glu Leu Ser Met Trp Arg Cys Asn Asp Glu Leu Arg Val Arg 325 330 335 gca gaa gaa ctt cac agg aat tcc aag aaa gat gaa gtt gca aaa cac 1056

Ala Glu Glu Leu His Arg Asn Ser Lys Lys Asp Glu Val Ala Lys His 340 345 350 tat ata gag ttt tgg aaa aaa att cct ttg aat gaa cca tac cgt gtt 1104

Tyr Ile Glu Phe Trp Lys Lys Ile Pro Leu Asn Glu Pro Tyr Arg Val 355 360 365

FIG. 7D gta ctc ggg gag gta agg gac aag ctc tat cgc act cgt gag cgt tct 1152

Val Leu Gly Glu Val Arg Asp Lys Leu Tyr Arg Thr Arg Glu Arg Ser 370 375 380 cgt tat ctc cta gct cat ggc tac tgt gaa att cct gaa gaa gcc aca 1200

Arg Tyr Leu Leu Ala His Gly Tyr Cys Glu Ile Pro Glu Glu Ala Thr 385 390 395 400 ttc acc aat gtc gat gag ttt ctg gaa cct ctt gaa ctc tgc tac aga 1248

Phe Thr Asn Val Asp Glu Phe Leu Glu Pro Leu Glu Leu Cys Tyr Arg 405 410 415 tca ctc tgt gct tgt ggt gat cgt gca att gct gat gga agc ctt ctt 1296

Ser Leu Cys Ala Cys Gly Asp Arg Ala Ile Ala Asp Gly Ser Leu Leu 420 425 430 gat ttc ttg agg caa gtt tcc act ttt gga ctg tca ctt gta agg ctt 1344

Asp Phe Leu Arg Gln Val Ser Thr Phe Gly Leu Ser Leu Val Arg Leu 435 440 445 gat ata cgg caa gag tct gat cgt cac act gac gtg atg gat gcc att 1392

Asp Ile Arg Gln Glu Ser Asp Arg His Thr Asp Val Met Asp Ala Ile 450 455 460 acc aaa cat ttg gaa att gga tcc tac caa gaa tgg tct gaa gaa aaa 1440

Thr Lys His Leu Glu Ile Gly Ser Tyr Gln Glu Trp Ser Glu Glu Lys 465 470 475 480 aga cag gaa tgg ctt ttg tcc gag ttg att ggc aaa agg cca ctc ttt 1488

Arg Gln Glu Trp Leu Leu Ser Glu Leu Ile Gly Lys Arg Pro Leu Phe 485 490 495

FIG. 7E gga cct gac cta ccc caa acc gat gaa att aga gat gtt tta gac acg 1536

Gly Pro Asp Leu Pro Gln Thr Asp Glu Ile Arg Asp Val Leu Asp Thr 500 505 510 ttc cgt gtc ata gca gaa ctt cca tct gac aac ttt gga gcc tac atc 1584

Phe Arg Val Ile Ala Glu Leu Pro Ser Asp Asn Phe Gly Ala Tyr Ile 515 520 525 att tcg atg gca act gca ccg tct gat gtg ctg gca gtt gag ctt ctt 1632

Ile Ser Met Ala Thr Ala Pro Ser Asp Val Leu Ala Val Glu Leu Leu 530 535 540 caa cgt gaa tgc aaa gtc agg aat cca tta aga gtc gtt ccg ttg ttt 1680

Gln Arg Glu Cys Lys Val Arg Asn Pro Leu Arg Val Val Pro Leu Phe 545 550 555 560 gaa aag ctt gat gat ctt gag tct gct cct gct gca ttg gct cgg ttg 1728

Glu Lys Leu Asp Asp Leu Glu Ser Ala Pro Ala Ala Leu Ala Arg Leu 565 570 575 ttc tcc ata gac tgg tac att aac cgg atc gat ggg aag caa gaa gtt 1776

Phe Ser Ile Asp Trp Tyr Ile Asn Arg Ile Asp Gly Lys Gln Glu Val 580 585 590 atg att gga tat tct gat tca gga aaa gat gct gga agg ttt tct gca 1824

Met Ile Gly Tyr Ser Asp Ser Gly Lys Asp Ala Gly Arg Phe Ser Ala 595 600 605 gca tgg cag cta tat aag gct cag gag gac ctc atc aaa gtc gca cag 1872

Ala Trp Gln Leu Tyr Lys Ala Gln Glu Asp Leu Ile Lys Val Ala Gln 610 615 620

FIG. 7F aaa ttt ggt gtt aag cta acc atg ttc cac ggt cgt ggt gga act gtt 1920

Lys Phe Gly Val Lys Leu Thr Met Phe His Gly Arg Gly Gly Thr Val 625 630 635 640 gga aga gga ggt gga cct acc cat ctt gct atc ttg tct caa cca cca 1968

Gly Arg Gly Gly Gly Pro Thr His Leu Ala Ile Leu Ser Gln Pro Pro 645 650 655 gaa aca att cac gga tct ctt cgt gtg aca gtt caa ggt gaa gtt att 2016

Glu Thr Ile His Gly Ser Leu Arg Val Thr Val Gln Gly Glu Val Ile 660 665 670 gaa cag tcg ttc ggt gag gaa cac ttg tgc ttt agg aca ctg caa cgt 2064

Glu Gln Ser Phe Gly Glu Glu His Leu Cys Phe Arg Thr Leu Gln Arg 675 680 685 ttc act gct gct act cta gaa cat gga atg cgt ccc cca agc tct cca 2112

Phe Thr Ala Ala Thr Leu Glu His Gly Met Arg Pro Pro Ser Ser Pro 690 695 700 aaa cca gaa tgg cgc gcc ttg atg gat cag atg gct gtc att gca act 2160

Lys Pro Glu Trp Arg Ala Leu Met Asp Gln Met Ala Val Ile Ala Thr 705 710 715 720 gag gaa tac cgt tca att gtg ttc aag gaa cca cgt ttt gtt gag tat 2208

Glu Glu Tyr Arg Ser Ile Val Phe Lys Glu Pro Arg Phe Val Glu Tyr 725 730 735 ttc cgt ctg gct aca cca gag atg gag tat ggt agg atg aac att gga 2256

Phe Arg Leu Ala Thr Pro Glu Met Glu Tyr Gly Arg Met Asn Ile Gly 740 745 750

FIG. 7G agt cga ccg gca aag aga agg cct agt gga ggc att gaa aca ctg cgt 2304

Ser Arg Pro Ala Lys Arg Arg Pro Ser Gly Gly Ile Glu Thr Leu Arg 755 760 765 gcg ata cca tgg atc ttt gcc tgg aca cag aca agg ttt cat ctt cca 2352

Ala Ile Pro Trp Ile Phe Ala Trp Thr Gln Thr Arg Phe His Leu Pro 770 775 780 gta tgg ctg ggc ttt gga gca gca ttt aga caa gtt gtt cag aag gat 2400

Val Trp Leu Gly Phe Gly Ala Ala Phe Arg Gln Val Val Gln Lys Asp 785 790 795 800 gtt aag aat ctc cat atg ctg caa gag atg tac aat caa tgg cct ttc 2448

Val Lys Asn Leu His Met Leu Gln Glu Met Tyr Asn Gln Trp Pro Phe 805 810 815 ttt agg gtt aca att gat tta gtt gaa atg gtg ttt gcc aag ggt gac 2496

Phe Arg Val Thr Ile Asp Leu Val Glu Met Val Phe Ala Lys Gly Asp 820 825 830 cct ggt att gca gca ctg aat gat agg ctc cta gtt tca aag gat ctg 2544

Pro Gly Ile Ala Ala Leu Asn Asp Arg Leu Leu Val Ser Lys Asp Leu 835 840 845 tgg cca ttt ggg gaa caa ttg aga agc aaa tat gaa gaa act aag aaa 2592

Trp Pro Phe Gly Glu Gln Leu Arg Ser Lys Tyr Glu Glu Thr Lys Lys 850 855 860 ctc cta ctt cag gtg gct gca cac aag gaa gtt ctt gaa ggt gac ccc 2640

Leu Leu Leu Gln Val Ala Ala His Lys Glu Val Leu Glu Gly Asp Pro 865 870 875 880

FIG. 7H tac ttg aag caa aga ctc aga ctc cgt gat tcg tac att aca acc ctt 2688

Tyr Leu Lys Gln Arg Leu Arg Leu Arg Asp Ser Tyr Ile Thr Thr Leu 885 890 895 aat gtt ttc caa gcc tac aca ttg aaa cgg atc cgc gat cca aac tac 2736

Asn Val Phe Gln Ala Tyr Thr Leu Lys Arg Ile Arg Asp Pro Asn Tyr 900 905 910 aag gtg gag gtg cgc ccc cca ata tcg aaa gag tct gct gaa aca agt 2784

Lys Val Glu Val Arg Pro Pro Ile Ser Lys Glu Ser Ala Glu Thr Ser 915 920 925 aaa cca gct gat gaa ctt gta aca ttg aat cca aca agt gaa tat gct 2832

Lys Pro Ala Asp Glu Leu Val Thr Leu Asn Pro Thr Ser Glu Tyr Ala 930 935 940 cct ggt ttg gaa gac aca ctc att ctt acc atg aag ggt att gct gct 2880

Pro Gly Leu Glu Asp Thr Leu Ile Leu Thr Met Lys Gly Ile Ala Ala 945 950 955 960 ggc atg cag aac act ggt taa 2901

Gly Met Gln Asn Thr Gly

FIG. 8

N-terminus

C-terminus

ATP-binding domains

Pyruvate binding domain

Biotin binding domain

FIG. 10A

*Rhizopus oryzae* rRNA cluster region (promoter sequence in italics)

gggggaccac atgggaatac tggttgctgt agttttgctt tttttt*actt ttttttttact* 60

*tttttttttt tttactttac tttaaatgtt tccttaacag ctctaaaaca atcttagaac* 120

*aatttaatat atcttttttt tttttttttg catataaaat ataggcttaa aatgacctat* 180

*attgattgta aactatgata tagttcacta gtagtaagca tgccaaagat gaataaaaaa* 240

*gaatatgtgt ttaaaaaaat tcgaaaatca tatttttttt tacatgtaaa agatagttaa* 300

*aaatgggggg ttttttttat ttttattttt tttacatata aaacataggc ttaaaatgac* 360

*ctgtattgat tgtaaactat aatatagttc actagcagta cgcatgccaa agataagtaa* 420

*aaaagaatat gtgtttaaaa aagttcgaaa attatatttt ttttttttac atgtaaaaga* 480

*tagccttaaa atggggatta ttttttattt ttttttttac atataaaaca taggcttaaa* 540

*atgacctata ttgatcaagg attatagtaa agtacatttg taataggtaa ggtggctaag* 600

*attttaaaaa aaaagcctac ttaaaaattc caaaaaatag tttttttttt ttacatataa* 660

*attgtatctc caaaatgatt taaattgatc aaggactaca tcaaagtaca ttaacaataa* 720

*gtagggtaag taaagttaca aaagaaagcg catttaaaat gactaagaat ccatcactaa* 780

*gaatttatca ctaaaattta ccaagtgcat atctgggatt aaaattgaat caccgatttc* 840

*atctcaaact ctatgaaaaa acaccttaaa ttctaaataa ctctatgaaa acttatccaa* 900

*a*atgaacaag caatacgtag aattgtagaa aaaaaaatta ggtttttgac tatattttcg 960
gatttttgct aagtcatttt tggctgagat aaatttagtt ttgtccaaac cttgattttt 1020
ttttttcgga ccgatgattt tactaaaaaa taaataatca atgtccggat agcacatatt 1080
gaacctcatg gaaggcgaaa acgaaagttt gagcttttca cacatcgagg ctgtgagtct 1140
tggataacct atggtagaaa ggaaatatct tttctactgt taaagttccc ggattaaatc 1200
ttgtcgtaca cttccttatg ggagcagatg ggcgagtcgc tggctcctgc ggaagctctt 1260
tgagttaccg tagtgagaaa agatggggat tgtatattat tacctatcca ggtatgatta 1320

FIG. 10B caagccaact cctgggcacc tttattggag tccatcgact gatctgctgg gaaaaattta 1380
tttttctttg cgttgatcgg acgaaaactg taggattgct aaagggaaat taaagtagat 1440
tgtgcaaacg ttcagcagat atgcagaatg tagtatgatc tgctttctct ttcaaagggt 1500
ttatcccctt tgggtagtcg actggtacgc catggaaaaa aagtgggctc ttctttgaag 1560
agtctcgtct aagctttcga gtttaggcta actttttaac ctgatagtta cctggttgat 1620

FIG. 11A pyruvate carboxylase cDNA from *Rhizopus oryzae* NRRL 1526

ATGCCTGCTGCACCAGTACGTGAACACTCTGTGGATACCATTCGTAGAAATAGCGAAGTGAT
GGGTAACCTGAGAAAATTGATGGTGGTTAATCGTGGTGAAATTGCTATCCGTGTCTTTCGTA
CAGCTCATGAACTCTCTATGAAGACAGTAGCTATTTTCTCTCATGAAGATAGATTATCCATGC
ACAGATATAAGGCGGATGAATCCTATCAACTCGGTCGTATTGGTCAATACACACCTGTAGGT
GCTTATCTGGCACAAGATGAAGTCGTTCGAATCGCAAAGGAACGTGGTGTGAGCATGATTCA
TCCTGGTTATGGTTTCTTGTCTGAAAATGCTGAATTCGCTCGCAAGGTGGAAGCTGCAGGAA
TCACTTTCATTGGTCCCTCTCCTGATGTCATTGAAAGTTTAGGCGATAAGACAAAAGCCAGA
ACGATTGCCATGAAGTGTGAAGTCCCTGTTGTCCCTGGTACACCTGGACCTGTCAGTGAATA
CAAAGAGGCCCTGAACTTTATCAAAGAATATGGTTTCCTATCATCATCAAGGCTGCCATGG
GTGGTGGTGGTCGTGGTATGCGTGTGGTTCGTGACGAAGCCAGTCTAGAGGACGCGTTTACC
CGTGCGAAATCTGAAGCTTTGGCTGCCTTTGGTGATGGCACTGTCTTTATCGAACGTTTCCTT
GATAAGCCTCGTCATATCGAGGTTCAATTGTTGGCAGATCGTGCAGGTAACGTGGTCCATCT
CTTTGAACGTGATTGTTCTGTTCAGCGTCGTCACCAAAAGGTGGTTGAAATCGCCCCTGCCA
AAAACTTGGATAACAAGGTACGTGAGGCCATCTTGAACGATGCGATCAAGATTGCCAAGGC
TGTAAAGTACAAGAACGCGGGTACTGCAGAATTCTTGGTGGATAACCAAAACCGTCACTACT
TTATCGAAATCAATCCTCGTATCCAAGTCGAACATACCATCACAGAAGAAATCACGGGTATT
GATATCGTTGCCGCTCAAATTCAGATCGCTGCCGGTGCCCTCTTGCCTCAATTGGGTCTTACC
CAACAACGTATCCGTCAACGTGGGTTCGCGATCCAGTGTCGTGTGACAACCGAGGACCCCGA
AAAGAATTTCCAGCCTGACACGGGTAAGATCGAAGTGTACCGTTCCTCTGGTGGTAACGGTG
TTCGTCTGGATGGTGGTGCTGGTTACGCAGGTGCTATCATTACCCCTCACTATGATTCACTTT
TGGTCAAAGTCTCTTGTTCTGGATCCACCTACGAAGTCGCTCGTCGCAAGATCGTCCGTGCCT
TGGTCGAATTCAGAATCCGTGGTGTCAAGACCAATATCCCCTTCTTACAACGTCTCTTGACCC
ATGATACCTTCATCAACGGTAACTGCTGGACAACTTTCATTGATGATACTCCCGATCTTTTCC
GTCTTGTTCAATTCCAAAACCGTGCTCAAAGACTCTTGGGTTACCTGGGTGATGTCGTCGTCA
ATGGTTCTCAAATCAAGGGTCAAATGGGTGATCCCATTCTGAAGCAAGAGATCGAAATCCCC
GTGTTGCGTGAAAGTGGTAGTGACAAGACGGTCGATGTCTCTGCTCCTGCTACGGAAGGCTG
GAGAAAGATCATTGTGGAACAAGGACCTGAAGCTTTCGCAAAAGCTGTCCGTGCTTACCCTG
GTGTCTTGATCACCGATACCACCTGGAGAGACGCTCATCAGAGTTTATTGGCCACTCGTGTG
AGAACTGTCGATCTCTTGCGTATCGCCCCTGCTACCTCTCACGCTTTGGCCAACGCCTTTTCA
TTGGAATGTTGGGGAGGTGCTACGTTTGATGTTGCTATGCGTTTCCTTCATGAAGATCCTTGG

FIG. 11B

GACCGTCTTGCTGCTTTGCGAAAGTTGGTACCCAATGTACCCTTCCAAATGCTTTTGCGTGGT
GCCAATGCGGTAGGTTACACCTCTTACCCTGATAACGTTATCTATGAATTCTGTGACAAGGC
AGTCAAGTGTGGTATGGATGTCTTCCGTATCTTTGACTCTCTCAATTATGTTGAAAACATGAG
ATTGGGTATTGACGCTGTCAAGAAGGCCGGTGGTGTTGTTGAAGCCACCATCTGTTACACGG
GTGATGTCTCCAACCCTAACCGCAAGAAGTACGACTTGAAGTACTACCTTGACCTGACACAA
TCCTTGGTGAACGAAGGTATTCACATCTTGGGTATCAAGGACATGGCTGGTCTTCTCAAACC
CGAGGCAGCCAAGTTACTGGTCTCCAGTATCCGTGCCAAGTTCCCCGACTTGCCCATTCACG
TTCACACACACGATACCGCAGGTACGGGTGTTGCTAGCATGATGGCCGCTGCCGCTGCTGGT
GCTGACATTGTTGATGTTGCCGTGGACGCCATGTCCGGCATGACCTCTCAACCGGCGATGGG
TGCCATTGTCGCTGGACTTGAACAGACCAATTTGGGTACCGGTATCCGCATGGAAGACATTC
ATGCCATCAATTCTTACTGGGAGCAATGCCGTTTGCTTTACTCTTGCTTCGAAGCCAACGTGC
GTTCGGCCGATTCGGGTGTCTATGAACATGAAATGCCTGGTGGACAATATACCAACTTGATG
TTCCAAGCCCAACAACTCGGCTTGGGAACTCAGTGGAAGCAAATCAAGAAGGCTTACAAGG
AGGCCAACGAACTCTGTGGTGACTTGGTCAAGGTCACGCCTTCGTCCAAGGTCGTGGGTGAT
CTTGCTCAATTCATGGTTTCCAACCAACTCTCTGCCAAAGAATTTGAAGAACGCGCCTCGAG
TCTCTCTCTGCCCACCTCTGTCATCGAGTTCTTCCAAGGTTATCTCGGTCAACCCTATGGCGG
TTTCCCCGAGCCCTTGCGCTCCAACATCCTTCGTGATCTCCCTCGCCTCGACGGTCGCCCTGG
TGCTAGCCTGCCTCCGTTGGACATGGCTAAACTCAAGGAAGAGTTGGTTGAAAAGTACGGTT
CGAGCATCCGTGATTACGACGTGATCTCGGCTGCTCTTTACCCCAAGGTCTTTGCCGACTACC
GTGATACCGTCAGTCAATACGGTGATCTCTCCGTTTTGCCTACACGCTACTTTTTGTCCAAGC
CCGAGATCAATGAAGAATTCCATGTGGAGATTGAAGAAGGAAAGACGTTGATCATCAAGTT
ATTGGCCGTCGGTCCTCTGAACAATGACGGTAAACGTGATGTTTACTTTGAATTGAACGGTG
AAGCTCGTGTGGTGGGCATTGTGGATCGCAATTCTGCTATTGAAATCGTCACACGTGAAAAG
GCCAACCCCTCCAACCCCGGTGACATTGGTGCTCCTATGTCGGGTGTGGTTGTCGAGATCCG
TGCCAAGGAAGGTAGCCATGTCAAGGCCAGTGATCCTCTGGCTGTTCTCTCTGCTATGAAGA
TGGAAACAGTGGTCACTGCTCCCGTGGCTGGTAGAGTTGAGCGTGTTGCTATCCAAGAAGGT
GATTCATTATCCGCTGGTGATTTGGTGGCCAAGGTTGTCAAAGAGGAAGCCTAA

FIG. 11C pyruvate carboxylase protein translated from pyrC cDNA from *R. oryzae* 1526

MPAAPVREHSVDTIRRNSEVMGNLRKLMVVNRGEIAIRVFRTAHELSMKTVAIFSHEDRLSMHR
YKADESYQLGRIGQYTPVGAYLAQDEVVRIAKERGVSMIHPGYGFLSENAEFARKVEAAGITFIG
PSPDVIESLGDKTKARTIAMKCEVPVVPGTPGPVSEYKEALNFIKEYGFPIIIKAAMGGGGRGMRV
VRDEASLEDAFTRAKSEALAAFGDGTVFIERFLDKPRHIEVQLLADRAGNVVHLFERDCSVQRR
HQKVVEIAPAKNLDNKVREAILNDAIKIAKAVKYKNAGTAEFLVDNQNRHYFIEINPRIQVEHTIT
EEITGIDIVAAQIQIAAGALLPQLGLTQQRIRQRGFAIQCRVTTEDPEKNFQPDTGKIEVYRSSGGN
GVRLDGGAGYAGAIITPHYDSLLVKVSCSGSTYEVARRKIVRALVEFRIRGVKTNIPFLQRLLTHD
TFINGNCWTTFIDDTPDLFRLVQFQNRAQRLLGYLGDVVVNGSQIKGQMGDPILKQEIEIPVLRES
GSDKTVDVSAPATEGWRKIIVEQGPEAFAKAVRAYPGVLITDTTWRDAHQSLLATRVRTVDLLR
IAPATSHALANAFSLECWGGATFDVAMRFLHEDPWDRLAALRKLVPNVPFQMLLRGANAVGYT
SYPDNVIYEFCDKAVKCGMDVFRIFDSLNYVENMRLGIDAVKKAGGVVEATICYTGDVSNPNR
KKYDLKYYLDLTQSLVNEGIHILGIKDMAGLLKPEAAKLLVSSIRAKFPDLPIHVHTHDTAGTGV
ASMMAAAAAGADIVDVAVDAMSGMTSQPAMGAIVAGLEQTNLGTGIRMEDIHAINSYWEQCR
LLYSCFEANVRSADSGVYEHEMPGGQYTNLMFQAQQLGLGTQWKQIKKAYKEANELCGDLVK
VTPSSKVVGDLAQFMVSNQLSAKEFEERASSLSLPTSVIEFFQGYLGQPYGGFPEPLRSNILRDLP
RLDGRPGASLPPLDMAKLKEELVEKYGSSIRDYDVISAALYPKVFADYRDTVSQYGDLSVLPTR
YFLSKPEINEEFHVEIEEGKTLIIKLLAVGPLNNDGKRDVYFELNGEARVVGIVDRNSAIEIVTREK
ANPSNPGDIGAPMSGVVVEIRAKEGSHVKASDPLAVLSAMKMETVVTAPVAGRVERVAIQEGD
SLSLAGDLVAKVVKEEA

COMPOSITIONS AND METHODS FOR MANIPULATING CARBON FLUX IN CELLS

CROSS-REFERENCE TO RELATED APPLICATIONS

This application claims priority as a continuation-in-part of U.S. application Ser. No. 12/195,869, filed Aug. 21, 2008, now U.S. Pat. No. 7,566,563 issued Jul. 28, 2009, which itself claims priority as continuation of U.S. application Ser. No. 11/334,713, filed Jan. 17, 2006, now U.S. Pat. No. 7,435,168 issued Oct. 14, 2008, which claims priority to U.S. Provisional Application Ser. No. 60/643,982, filed Jan. 14, 2005, each of the contents of the entirety of which are incorporated by this reference.

FIELD OF THE INVENTION

The present invention relates to novel nucleic acids and related methods that can be used to regulate genes encoding enzymes that manipulate carbon flux through metabolic pathways.

BACKGROUND

Metabolic engineering of microorganisms is an effective means to produce commercially a number of chemicals useful for a variety of applications, including production of polymer monomers and food additives (see, e.g., Lee, S. Y., et al. *Macromol. Biosci.* 4:157-164 (2004)).

As an example, fumaric acid is an organic acid widely found in nature. In humans and other mammals, fumaric acid is a key intermediate in the tricarboxylic acid cycle for organic acid biosynthesis (also known as the Krebs cycle or the citric acid cycle). Fumaric acid is also an essential ingredient in plant life. Fumaric acid is the strongest organic food acid in titratable acidity and in sourness. In one example, commercial fumaric acid is made from N-butane that is oxidized to maleic acid that is then isomerized to fumaric acid. Production of fumaric acid by bioprocess methods has potential to avoid synthetic production processes that often are more costly than bioprocess methods.

As an additional example, lactic acid (lactate) is used in the food industry as an additive for preservation, flavor, and acidity. It is also used for the manufacture of poly-lactic acid, a biodegradable plastic, and ethyl lactate, an environmentally friendly nonchlorinated solvent. Worldwide, in excess of 100,000 tons of lactic acid is produced annually, with predictions of an increasing demand. The growth in demand is attributable to the poly-lactic acid and ethyl acetate products.

In a number of microorganisms, lactic acid is normally produced from pyruvic acid (pyruvate). The reaction also occurs in the cells of higher organisms when oxygen is limited. Glycolysis is the sequence of reactions that converts glucose into pyruvic acid (pyruvate). Glycolysis can be carried out anaerobically. Pyruvic acid has a number of fates depending on where the chemical reaction takes place and whether the reaction takes place in the presence or absence of oxygen.

As shown in FIG. 1, under aerobic conditions, pyruvic acid can be converted to acetyl-CoA by pyruvate dehydrogenase. Under anaerobic conditions, pyruvic acid can be converted to ethanol (alcoholic fermentation) or lactic acid (e.g., in contracting muscle). The conversion of pyruvic acid to lactic acid is catalyzed by lactate dehydrogenase (LDH). The efficiency of lactic acid fermentation can be quantified as the percent yield of lactate from glucose or as a decrease in the levels of co-products (e.g., glycerol, ethanol, and fumarate) found in the fermentation broth.

Lactic acid is often manufactured using *Lactobacilli*, which typically has specialized growth requirements and is unable to produce significant amounts of lactic acid below pH 4. (Skory, C. D. *J. Ind. Microbiol. Biotechnol.* 30:22-27 (2003)). Alternatively, maintenance of neutral pH results in decreased product solubility in the form of salts and requires further processing to regenerate the acid from the resulting lactate salt.

*Saccharomyces cerevisiae* is a hearty, acid-tolerant microorganism that is amenable to industrial processes. In these microorganisms, however, the major product of pyruvate metabolism is ethanol, by way of pyruvate decarboxylase. Skory reported the production of lactic acid in a yeast, *S. cerevisiae*, expressing an Idh gene derived from *Rhizopus oryzae*. (*J. Ind. Microbiol. Biotechnol.* 30:22-27, (2003)). Skory demonstrated an increase in lactic acid production in the recombinant yeast. Nevertheless, despite the increase in lactic acid production, the majority of carbon was diverted into ethanol. In the same report, when lactic acid production was studied in a *S. cerevisiae* mutant strain deficient in ethanol production, diminished ethanol production was observed, but the efficiency of lactic acid production also decreased.

Anderson et al. demonstrated that Idh activity had little or no effect on the flux of carbon to lactic acid in *Lactococcus lactis*. *Eur. J. Biochem.*, 268:6379-6389 (2001). Despite increasing the expression and activity of Idh to beyond that found in wild-type *L. lactis*, researchers observed no change in the flux of carbon to lactic acid.

Lactic acid can be synthesized chemically, but such synthesis results in a mixture of D and L isomers. The products of microbiological fermentation depend on the organism used and also may include a mixture of the two isomers or individual isomers in a stereospecific form. The desired stereospecificity of the product depends on the intended use; however, L-(+)-lactic acid is the form desired for most applications (Skory, C. D. *Appl. Environ. Microbiol.* 66:2343-2348 (2000)).

U.S. Pat. No. 6,528,636 describes *R. oryzae* (ATCC 9363) as a lactic acid producer found in the *Rhizopus* genus. *Rhizopus* is a filamentous fungus that is commercially versatile and used in the production of fermented foods, industrial enzymes such as glucoamylase and lipase, corticosteroids, chemicals such as glycerol and ethanol, as well as organic acids such as lactic acid and fumaric acid.

Production levels of different metabolites vary tremendously among the *Rhizopus* species, with some species producing predominantly lactic acid and others producing primarily fumaric acid. An ideal lactic acid-producing *Rhizopus* strain would produce little or none of these metabolites, since their production depletes sugars that could be used for conversion to lactic acid.

Ethanol is believed to be produced by most *Rhizopus* species primarily in low oxygen conditions. While *Rhizopus* is not typically considered an organism that grows under anaerobic conditions, it does possess ethanol fermentative enzymes that allow the fungus to grow for short periods in the absence of oxygen.

U.S. Pat. No. 4,877,731 discusses that fumaric acid production has been well studied in *Rhizopus* and that the fumarase gene also has been isolated. Synthesis of fumarate is believed to occur primarily through the conversion of pyruvate to oxaloacetate by pyruvate carboxylase. Conditions leading to increased fumaric acid usually are associated with aerobic growth in high glucose levels and low available nitrogen. Accumulation of fumarate often is a problem with lactic acid production, because its low solubility can lead to detrimental precipitations that compromise fermentative efficiency.

Glycerol is also a by-product that often is produced by *Rhizopus* grown in high glucose-containing medium. Glycerol is thought to accumulate in *Rhizopus* in a manner similar to that found in *Saccharomyces* (U.S. Pat. No. 6,268,189).

Oxaloacetate is also produced by *Rhizopus*. Pyruvate carboxylase [EC 6.4.1.1] is a member of the family of biotin-dependent carboxylases which catalyzes the carboxylation of pyruvate to form oxaloacetate with concomitant ATP cleavage. The resulting oxaloacetate can be used for the synthesis of glucose, fat, and some amino acids or other derivatives. The enzyme is highly conserved and is found in a wide variety of prokaryotes and eukaryotes. During fermentation by *Rhizopus oryzae*, pyruvate is primarily converted to lactic acid, but other by-products such as fumaric acid, ethanol and glycerol are also produced. In this fungus, there is evidence that fumaric acid production is predominantly from cytosolic oxaloacetate that is converted from pyruvate by pyruvate carboxylase (Osmani, S. A., et al., *Eur. J. Biochem.* 147:119-128 (1985)).

Active pyruvate carboxylase consists of four identical subunits arranged in a tetrahedron-like structure. Each subunit contains three functional domains: the biotin carboxylation domain, the transcarboxylation domain and the biotin carboxyl carrier domain (Jitrapakdee, S., et al., *Biochem. J.* 340:1-16 (1999)). Pyruvate carboxylases contain the prosthetic group biotin, which is covalently bound to the amino group of a specific lysine residue. The overall reaction catalyzed by pyruvate carboxylase involves two partial reactions that occur at spatially separate subsites within the active site, with the covalently bound biotin acting as a mobile carboxyl group carrier. In the first partial reaction, biotin is carboxylated using ATP and $HCO_3^-$ as substrates, while in the second partial reaction, the carboxyl group from carboxybiotin is transferred to pyruvate (Attwood, P. V., *Int. J. Biochem. Cell Biol.* 27:231-249 (1995)).

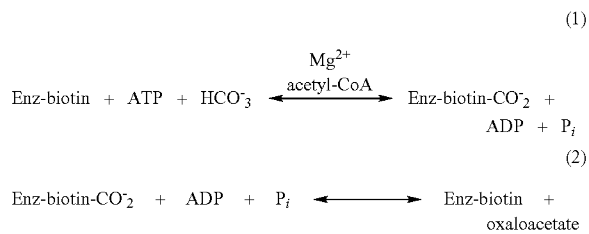

Pyruvate carboxylase was first described by (Utter, M. F., et al., *J. Biol. Chem.* 235:17-18 (1960)) in the course of defining the gluconeogenic pathway in chicken liver. Native pyruvate carboxylase from a number of sources, including bacteria, yeast, insects and mammals, consists of four identical subunits of approximately 120-130 kDa. Pyruvate carboxylases from many sources possess a reactive lysine residue that is essential for full enzymatic activity. Sequencing of cDNA encoding pyruvate carboxylase, as well as limited proteolysis and primary structure comparisons, have shown that pyruvate carboxylases from different species contain ATP, pyruvate, and biotin binding domains (Jitrapakdee and Wallace (1999); Koffas, M. A., et al., *Appl. Microbiol. Biotechnol.* 50:346-352 (1998)). In *S. cerevisiae* there are two pyruvate carboxylase isoenzymes (PYC1 and PYC2) encoded by separate genes (Stucka, R., et al., *Mol. Gen. Genet.* 229:307-315 (1991); Walker, M. E., et al., *Biochem. Biophys. Res. Commun.* 176:1210-1217 (1991)) while in mammals, no tissue-specific isoenzymes have been reported. Pyruvate carboxylase is most effectively activated by long-chain acyl-CoA derivatives, such as palmitoyl-CoA, and is inhibited by aspartate and 2-oxoglutarate (Osmani, S. A., et al., *Ann. N. Y. Acad. Sci.* 447:56-71 (1985)).

Fermentations with the fungus *Rhizopus* are often advantageous because the organism is able to produce optically metabolites, such as pure L-(+)-lactic acid. Therefore, the quality of the final product is considered to be superior to that obtained by bacterial fermentations. Furthermore, L-(+)-lactic acid is more desirable for making poly-lactic acid. (U.S. Pat. No. 6,268,189). Additionally, *Rhizopus* can grow in chemically simple medium without the need for complex components such as yeast extracts (Skory, C. D. *Curr. Microbiol.* 47:59-64 (2003)). Nevertheless, the efficiency of lactic acid and fumaric acid production (the amount of available carbon diverted to lactate or fumarate production) in *Rhizopus* generally is low as compared to bacterial fermentations. There also is little known in the art about gene regulatory elements for *Rhizopus*. There is a need for a method of increasing the efficiency and amount of lactate and fumarate production in *Rhizopus.*

SUMMARY

Provided herein are genes and genetic elements useful in modifying host cells, such as, without limitation, microorganisms. Further, the methods and compositions of the invention are useful for overexpressing, for example, and without limitation, specific metabolites in the microorganism, such as, without limitation, fumaric acid, lactic acid, malic acid and glycerol. Methods of manipulating carbon flux in a microorganism such as *R. oryzae* also are provided.

In one embodiment, an isolated polynucleotide is provided comprising a promoter such as a *Rhizopus* transcription elongation factor (tef) gene promoter or, in another embodiment, *Rhizopus* ribosomal RNA cluster (rRNA cluster) gene promoter. In one embodiment, the isolated polynucleotide comprises a promoter such as a *Rhizopus oryzae* transcription elongation factor (tef) gene promoter contained within a sequence shown in one of FIGS. 2, 3 and SEQ ID NO:1 and SEQ ID NO:2 as well as a *Rhizopus oryzae* ribosomal RNA cluster (rRNA cluster) gene promoter contained within a sequence shown in FIG. 10, SEQ ID NO:10 and SEQ ID NO:11. The isolated polynucleotide can comprise an expressed sequence, such as an open reading frame or a sequence encoding an antisense RNA or an interfering RNA operably linked to the promoter. In other embodiments, the expressed sequence encodes one of an siRNA and an antisense RNA directed to one of pyruvate dehydrogenase and pyruvate decarboxylase. In certain embodiments, the open reading frame encodes, for example, lactate dehydrogenase, pyruvate carboxylase, and phosphoenolpyruvate carboxylase. The polynucleotide may be contained within a vector and/or a host cell.

Also provided is the sequence of a novel pyruvate carboxylase gene (SEQ. ID NO:6 and SEQ ID NO: 26) and a protein product encoded thereof (SEQ ID NO:8 and SEQ ID NO: 27 respectively) obtained from *R. oryzae.*

In another embodiment, a method is provided for manipulating carbon flux in a microorganism comprising: culturing a cell containing a polynucleotide capable of expressing a sequence for manipulating carbon flux in a cell (for example, a sequence as described supra) and recovering one of lactic acid, glycerol and fumaric acid from the culture medium.

In another embodiment, a selectable marker for more efficient metabolic engineering of *Rhizopus* is provided.

It is to be understood that both the foregoing general description and the following detailed description are exemplary and explanatory only and are intended to provide further explanation of the invention as described and claimed.

BRIEF DESCRIPTION OF THE FIGURES

FIG. 2 shows the full length sequence of the tef gene promoter isolated from *R. oryzae*. (SEQ ID NO:1). The TATA box and ATG start codon are shown underlined.

FIG. 3 shows a truncated sequence of the tef gene promoter isolated from *R. oryzae*. (SEQ ID NO:2). The TATA box and ATG start codon are shown underlined.

FIG. 4 shows a portion of the external transcribed spacer (ETS) region of the 18s subunit of the ribosome isolated from *R. oryzae*. (SEQ ID NO:3).

FIGS. 5A-C show a comparison of nucleotide sequences pyruvate dehydrogenase from the genomic sequence "g" and the expressed sequence "c" of *R. oryzae* (SEQ ID NO:4 and SEQ ID NO:5, respectively).

FIGS. 6A-H show a cDNA sequence (SEQ ID NO:6) (FIGS. 6A-C), genomic DNA sequence (SEQ ID NO:7) (FIGS. 6D-F), and a protein sequence (SEQ ID NO:8) (FIGS. 6G-H) of *R. oryzae* 395 pyruvate carboxylase. The open reading frame encodes a protein of 1178 amino acids. The intron, 61 bp, is typed in italic lowercase.

FIGS. 7A-H show the cDNA and protein sequence of *Medicago sativa* phosphoenolpyruvate carboxylase (SEQ ID NO:9).

FIG. 8 shows conserved domains among *R. oryzae, S. cerevisiae, A. niger, A. terreus, P. pastoris*, and *S. pombe* pyruvate carboxylase proteins. The two ATP binding domains (amino acids 187-193 and 311-318 of the protein sequence provided in FIG. 6, underlined) and the biotin binding domain (amino acids 1138-1141 of the protein sequence provided in FIG. 6, underlined) are 100% conserved, while the pyruvate binding domain (amino acids 603-625 of the protein sequence provided in FIG. 6, underlined, with $W_{622}$ being the putative pyruvate binding site) is 89% conserved among these fungal proteins.

FIGS. 10A-B show a full length sequence of nucleotides 1-1043 of the rRNA cluster gene promoter region isolated from *R. oryzae* (SEQ ID NO:10). The rRNA cluster core promoter is shown in italics (SEQ ID NO:11).

FIGS. 11A-C show a cDNA sequence (SEQ ID NO:26) (FIGS. 11A-B) and a protein sequence (SEQ ID NO:27)(FIG. 11C) of *R. oryzae* 1526 pyruvate carboxylase. The open reading frame encodes a protein of 1179 amino acids.

DETAILED DESCRIPTION

Figure 1:
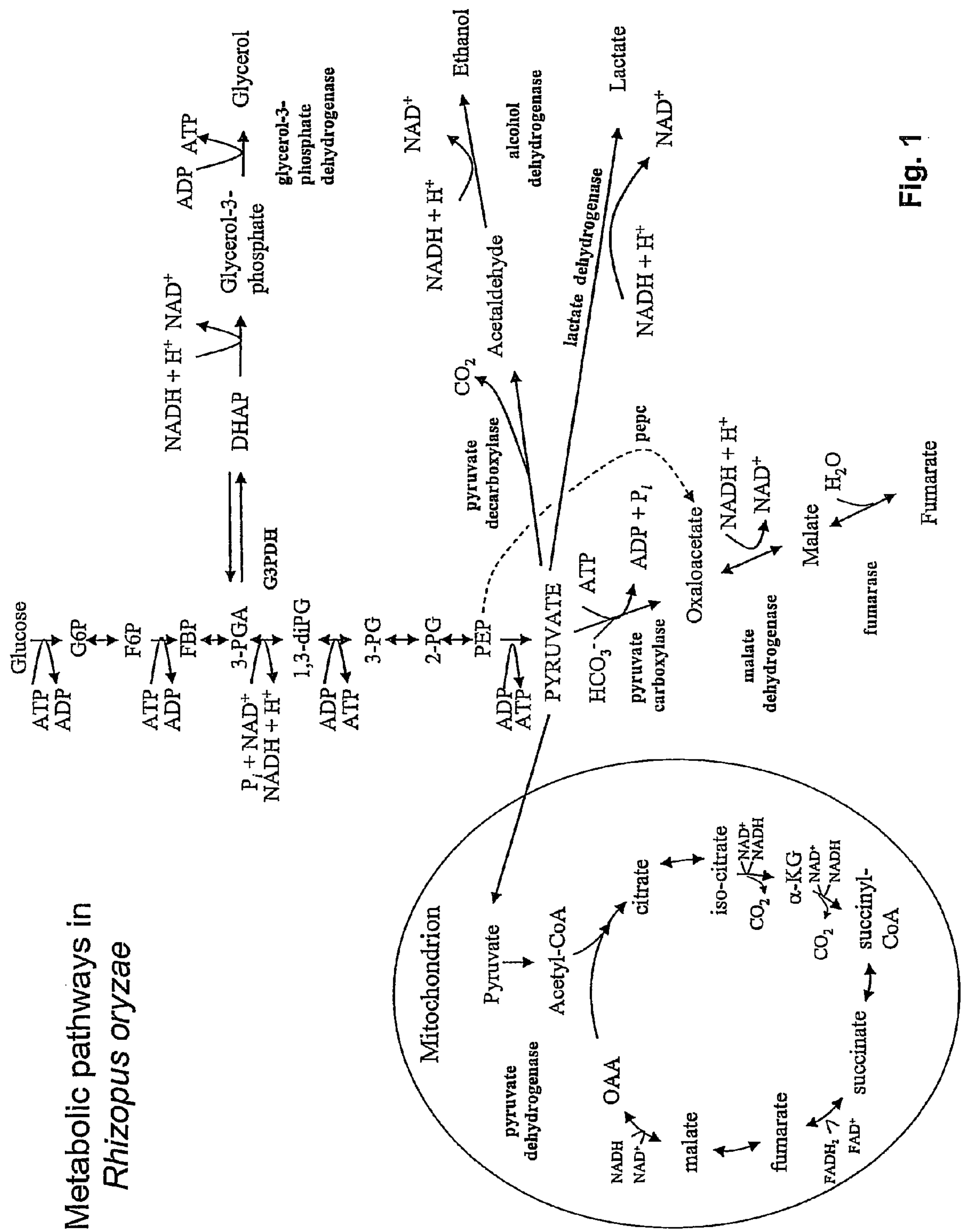
FIG. 1 is a diagram of common metabolic pathways in *R. oryzae*, with a PEP carboxylase pathway introduced by expression of phosphoenolpyruvate carboxylase gene (pepc) shown by the dotted line.

Provided herein are methods and compositions of matter useful in the manipulation of carbon flux in microorganisms, typically in members of the *Rhizopus* genus, and most typically in *R. oryzae*. As a non-limiting example, the manipulation of *R. oryzae* metabolic pathways depicted in FIG. 1 is facilitated by the methods and compositions of matter described herein. Tools for manipulating carbon flux described herein include novel promoters and/or gene sequences, as well as portions thereof and sequences complementary thereto which can be used in antisense and siRNA methods.

It is to be understood that certain descriptions of the present invention have been simplified to illustrate only those elements and limitations that are relevant to a clear understanding of the present invention, while eliminating, for purposes of clarity, other elements. Those of ordinary skill in the art, upon considering the present description of the invention, will recognize that other elements and/or limitations may be desirable in order to implement the present invention. However, because such other elements and/or limitations may be readily ascertained by one of ordinary skill upon considering the present description of the invention, and are not necessary for a complete understanding of the present invention, a discussion of such elements and limitations is not provided herein. As such, it is to be understood that the description set forth herein is merely exemplary to the present invention and is not intended to limit the scope of the claims.

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims may be read as if prefaced by the word "about", even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, may contain error(s) necessarily resulting from the standard deviation found in its underlying respective testing measurements. Furthermore, when numerical ranges are set forth herein, these ranges are inclusive of the recited range end points (end points may be used). When percentages by weight are used herein, the numerical values reported are relative to the total mass weight. Those of skill in the art recognize that percent mass weight and actual mass weight are interconvertable.

All referenced patents, patent applications, publications, sequence listings, electronic copies of sequence listings, or other disclosure material are incorporated by reference in whole but only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material. The articles "a,"

"an," and "the" are used herein to refer to one or more than one (i.e., to at least one) of the grammatical object of the article. By way of example, "an element" means one or more elements, and thus, possibly, more than one element is contemplated, and may be employed or used.

As used herein, the term "auxotroph" includes an organism that requires a specific growth factor (for example, an amino acid or sugar) for its growth. As used herein, the term "bradytroph" includes an organism that does not necessarily require a specific growth factor for its growth, but which produces a certain growth factor in lower amounts than a wild-type (w.t.) organism.

As used herein, the term "fumaric acid" includes trans 1,2-ethylenedicarboxylic acid in either the free acid or salt form. The salt form of fumaric acid is referred to as "fumarate" regardless of the anion, for example and without limitation, carbonate (e.g., neutralizing via calcium carbonate) or hydroxide (e.g., neutralizing via ammonium hydroxide).

As used herein, the term "lactic acid" includes 2-hydroxypropionic acid in either the free acid or salt form. The salt form of lactic acid is referred to as "lactate" regardless of the anion, for example and without limitation, carbonate (e.g., neutralizing via calcium carbonate) or hydroxide (e.g., neutralizing via ammonium hydroxide).

As used herein, the term "malic acid" includes hydroxybutanedioic acid in either the free acid or salt form. The salt form of malic acid is referred to as "malate" regardless of the anion, for example and without limitation, carbonate (e.g., neutralizing via calcium carbonate) or hydroxide (e.g., neutralizing via ammonium hydroxide).

As used herein, the term "gene" includes a segment of nucleic acid, DNA or RNA, which encodes and is capable of expressing a specific gene product. A gene often produces a protein or polypeptide as its gene product, but in its broader sense, a gene can produce any desired product, whether the product is a protein, polypeptide or nucleic acid. Functional or structural nucleic acid, such as, without limitation, rRNA, ribozymes, antisense RNA or interfering RNA (e.g., siRNA) also may be considered "gene products."

A "gene" contains an "expressed sequence" that can encode not only a protein or polypeptide, but a structural or functional nucleic acid, such as an antisense or siRNA. A gene may also contain sequences containing regulatory elements, such as, without limitation, promoters, enhancers and terminators; such regulatory elements may be "operably linked," most typically in an appropriate proximity to each other. Such promoters operate in cis (attached to each other on the same nucleic acid molecule) to cause expression of "a gene product." The choice of gene constituents, such as the particular combination of regulatory elements and expressed sequence, will dictate the conditions of expression. For example, a constitutive promoter, such as the CMV (cytomegalovirus) promoter, coupled to an expressed sequence will cause constitutive expression of the expressed sequence when transferred into a suitable host cell. A promoter is considered constitutive if it functions to promote transcription of a gene under normal growth conditions. A constitutive promoter is not tissue specific or developmentally specific, has broad cross-species tropism, and typically does not vary substantially in its expression under normal growth conditions.

A "gene" can include introns or other DNA sequences that can be spliced from the final RNA transcript. An expressed DNA sequence that encodes a protein or peptide ("protein encoding sequence") includes an open reading frame (ORF). The protein encoding sequence may comprise intervening introns. Further, the term "gene" includes expressed sequences as well as non-expressed sequences. All DNA sequences provided herein are understood to include complementary strands unless otherwise noted. Furthermore, RNA sequences can be prepared from DNA sequences by substituting uracil for thymine, and are included in the scope of this definition and the invention, along with RNA copies of the DNA sequences of the invention isolated from cells.

As used herein, the term "oligonucleotide" includes a nucleic acid of from about 7 to about 50 bases though they are more typically from about 15 to about 35 bases. Oligonucleotides are useful as probes or primers for use in hybridization or amplification assays such as Southern or Northern blots; molecular beacon; polymerase chain reaction (PCR); reverse transcriptive PCR (RT-PCR); quantitative RT-PCR (QRT-PCT), e.g., TAQMAN; isothermal amplification methods, such as NASBA (nucleic acid sequence-based amplification); and rolling circle amplification, including use of padlock probes. The oligonucleotides of the invention can be modified by the addition of peptides, labels (including fluorescent, quantum dot, or enzyme tags), and other chemical moieties and are understood to be included in the scope of this definition and the invention.

As used herein, in the context of the novel nucleotide sequences described herein, a nucleic acid is "specific to" a given sequence, such as the pyruvate carboxylase cDNA and genomic sequences provided, if it can hybridize specifically to a given sequence under stringent conditions, such as, without limitation, 0.2×SSC at 65° C. or in a PCR reaction under typical reaction (annealing) temperatures. Typically, one sequence is "specific" to a reference sequence if the nucleic acid has 90 to 100% homology (sequence identity) to the reference sequence.

The following terms are used to describe the sequence relationships between two or more nucleic acids or polynucleotides: (a) "reference sequence", (b) "comparison window", (c) "sequence identity", (d) "percentage of sequence identity", and (e) "substantial identity". As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence. As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches. Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) CABIOS 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, as modified in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is described by Higgins et al. (1988) *Gene* 73:237-244 (1988); Higgins et al. (1989) CABIOS 5:151-153; Corpet et al. (1988) *Nucleic Acids Res.* 16:10881-90; Huang et al. (1992) CABIOS 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, and PSI-BLAST, the default parameters of the respective programs (e.g., BLASTN for nucleotide sequences, BLASTX for proteins) can be used. See the National Center for Biotechnology Information website on the world wide web at ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3 and the nwsgapdna.cmp scoring matrix; or any equivalent program thereof. By "equivalent program" is intended to mean any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, at least 80%, at least 90%, or at least 95%, compared to a reference sequence using one of the alignment programs described using standard parameters.

In the context of the sequences provided herein, a sequence is specific to that reference sequence if, under any given reaction condition that can be used to distinguish one sequence from another, such as, without limitation, PCR, Southern blot or Northern blot, the nucleic acid can hybridize specifically to a nucleic sequence provided herein, but not to other sequences, such as sequences from other species including without limitation those of *S. cerevisiae, A. niger, A. terreus, P. pastoris*, and *S. pombe*. Thus, in a nucleic acid detection assay, a probe/primer is "specific to" a sequence if it can bind to a specific transcript or desired family of transcripts extracted from a specimen, to the practical exclusion (i.e., does not interfere substantially with the detection assay) of other sequences. In a PCR assay, primers are specific to a reference sequence if they specifically amplify a portion of that sequence, to the practical exclusion of other sequences in a sample.

As used herein, a "primer" or "probe" for detecting a specific nucleic acid species includes any primer, primer set, and/or probe that can be utilized to detect and/or quantify the specific nucleic acid species. A "nucleic acid species" can be a single nucleic acid species, corresponding to a single gene, or can be nucleic acids that are detected by a single common primer and/or probe combination.

As used herein, the term "host cell" includes any prokaryotic or eukaryotic cell where a desired nucleic acid sequence has been introduced into the cell. The metabolic processes and pathways of such a host cell are capable of maintaining, replicating, and/or expressing a vector containing a foreign gene or DNA molecule. There are a variety of suitable host cells, including but not limited to bacterial, fungal, insect, mammalian, and plant cells, that can be utilized in various ways (for example, as a carrier to maintain a plasmid comprising a desired sequence). Representative microbial host cells include, but are not limited to, fungal cells such as *Rhizopus* ssp., *Saccharomyces* ssp., *Streptomyces* ssp., *Pichia* ssp., *Aspergillus* ssp., and bacterial cells such as *Lactobacillus* ssp., *Escherichia* ssp., *Corynebacterium* ssp., *Brevibacterium* ssp., *Pseudomonas* ssp., *Proteus* ssp., *Enterobacter* ssp., *Citrobacter* ssp., *Erwinia* ssp., *Xanthomonas* ssp., *Flavobacterium* ssp., *Streptococcus* ssp., *Lactococcus* ssp., *Leuconostoc* ssp., and *Enterococcus* ssp. In one embodiment, the host cell is *Rhizopus oryzae*. In another embodiment, the host cell is *Escherichia coli*.

As used herein, the term "polynucleotide" includes any single-stranded sequence of nucleotide, connected by phosphodiester linkages, or any double-stranded sequences comprising two such complementary single-stranded sequences held together by hydrogen bonds. Unless otherwise indicated, each polynucleotide sequence set forth herein is presented as a sequence of deoxyribonucleotides (abbreviated A, G, C and T). The term "polynucleotide" encompasses DNA molecules or polynucleotide, sequences of deoxyribonucleotides, and RNA molecules or polyribonucleotides and combinations thereof.

As used herein, the term "promoter" includes a DNA sequence within a larger DNA sequence that provides or defines a site to which RNA polymerase can bind and initiate transcription. The promoters described herein can be used to over-express or up-regulate, for example, and without limitation, genes encoding enzymes that increase carbon flux to lactic acid, fumarate, and other desired metabolites during changes in fermentation conditions.

As used herein, the term "carbon flux" includes the biochemical pathway by which carbon is metabolized in an organism. A change in carbon flux, therefore, is a change in the metabolic processing of carbon in response to a change in the organism or its environment. Carbon flux may be changed in any manner, including but not limited to changing the environment of the organism, such as limiting oxygen and/or changing the expression of genes and gene products in the organism (e.g. introducing heterdogous gene sequences).

An "equivalent" of a given reference nucleotide sequence or element contained therein is a nucleotide sequence containing, as compared to the reference nucleotide sequence, all elements of that reference nucleotide sequence, such that the characteristic function of that reference nucleic acid or peptide is retained. Those of skill in the art understand that a functional protein may be encoded by equivalent DNA sequences due to degeneracy in the genetic code. For example, one codon may be substituted for another, yet encode the same amino acid, such as, for example and without limitation, in reference to the Ala codon, the substitution of GCC or GCG for GCA. In the case of proteins, a sequence can contain amino acids that represent conservative amino acid substitutions, including but not limited to, the conservative substitution groups: Ser and Thr; Leu, Ile and Val; Glu and Asp; and Gln and Asn. A sequence as claimed herein thus includes the referenced sequence as well as its equivalents due to degeneracy in the genetic code. Conservative substitutions also can be determined by other methods, such as, without limitation, those used by the BLAST (Basic Local Alignment Search Tool) algorithm, the BLOSUM Substitution Scoring Matrix, and the BLOSUM 62 matrix (see also, for example, Altschul et al., *Methods in Enzymology* 266:460-479 (1996)). Importantly, "equivalents" and "conserved equivalents" of a reference nucleic acid or peptide/protein substantially retain or enhance the function of the reference nucleic acid or peptide/protein.

As used herein, a "tef promoter" or "tef Pol II promoter" is the promoter for transcription of translation elongation factor. See, for example, FIGS. 2 and 3; and SEQ ID NO:1 and SEQ ID NO:2. Likewise, an "rRNA cluster promoter" is the promoter for transcription of ribosomal RNA such as the 5s (comprising the NTS1 promoter region) and 18s (comprising the NTS2 region) ribosomal RNA. Those of skill in the art recognize that ribosomal DNA (rDNA) in eukaryotes is arranged in tandemly repeated units containing the coding regions for 18S, 5.8S, and 28S ribosomal RNA separated by spacers. A large intergenic spacer (IGS) separates the 28S and 18S coding regions, and contains signals for transcription initiation and termination. The structure of the 35S pre-mRNA cluster is: NTS1::5S::NTS2::5'ETS::18S::ITS1::5.8S::ITS2::28S::3'ETS. The internal transcribed spacers (ITS), which separate the 5.8S gene from the 18S and 28S genes on either side of it, contain motifs responsible for the correct splicing of the mature 18S, 28S and 5.8S rRNA molecules from the primary rRNA transcript wherein the promoter regions drive expression of such rRNA. Examples of an rRNA cluster promoter sequence include that shown in FIG. 10 and the sequence listed in SEQ ID NO:10 and SEQ ID NO:11.

In the context of the promoters described herein, equivalents of those promoters substantially retain the promoter activity, host cell tropism and strength of the promoter. Methods of making "equivalent" promoters include any of the large variety of genetic engineering and/or mutational methods known to those of skill in the art. These methods can be used to create nucleic acid substitutions, deletions or insertions that do not substantially affect the promoter function.

For example, and without limitation, in the case of the tef promoter (see, for example, FIGS. 2 and 3; and SEQ ID NO:1 and SEQ ID NO:2), in the region located between the TATA box and the downstream transcription start site (AUG), one or more nucleotides may be inserted, deleted or substituted without substantially decreasing promoter function. Similarly, other cis-acting elements present in the tef promoter, such as those found 5' to the TATA box (bases 735 to 739 of SEQ ID NO:1, with the ATG start codon at bases 777 to 779; bases 208 to 213 of SEQ ID NO:2, with the ATG start codon at bases 251 to 253), may be retained, yet one or more nucleotides between those cis-acting elements may be inserted, deleted or modified without substantially decreasing promoter function. Even small 1 or 2 nucleotide substitutions, insertions and deletions within promoter elements may be tolerated without substantial loss of promoter function. As such, "equivalents" of the tef promoter contain sequences having at least about 90%, at least about 95% or at least about 97.5% sequence identity with the sequences of the invention. Both sequences presented in SEQ ID NO:1 and 2 retain the essential promoter characteristics of the tef promoter.

As with the tef promoter, certain portions of the rRNA cluster promoter are necessarily substantially conserved in "equivalents," while others are not. As discussed herein, and as is well-known in the art, Pol I promoters such as the rRNA cluster promoters contain a core element and an upstream control element ("UCE"). As such, nucleotide sequences between those elements need not be conserved, only their general spacing. Thus, outside the core and UCE sequences, any nucleotide can be deleted, inserted or substituted, so long as the ability of the promoter to cause expression of an operably linked expressed sequence is not substantially affected. Thus, for the tef promoter and the rRNA cluster promoter, an "equivalent" thereof retains, substantially, the ability of the promoters contained within the sequences to cause expression of gene product in a host cell. As discussed herein, methods for producing such equivalents, for example, by PCR-based or oligonucleotide-based mutational methods or other methods well known in the art. A person of ordinary skill in the art would be able to produce such equivalents with little difficulty. Testing for efficacy of the equivalent promoters can be performed in many ways known to those of average skill in the art. For the tef promoter, promoter function can be determined in *E. coli*, yeast and *Rhizopus* species, or another suitable host cell. Similarly, the rRNA cluster promoter can be tested in *E. coli*, yeast, and *Rhizopus* cells, or in any other suitable host cell. Expression levels can be determined by, for example and without limitation, Northern blot, by quantitative RT-PCR (e.g., TAQMAN) or by expression of an indicator gene product.

As used herein, the term "vector" includes a means for introducing a foreign nucleotide sequence into a cell, including without limitation, a plasmid or virus. Such vectors can operate under the control of a host cell's gene expression machinery. A vector contains sequences that facilitate replication and/or maintenance of a segment of foreign nucleic acid in the host cell. Generally, the vector is introduced into a host cell for replication and/or expression of the segment of foreign DNA or for delivery of the foreign DNA into the host genome. A typical plasmid vector contains: (i) an origin of replication, so that the vector can be maintained and/or replicated in a host cell; (ii) a selectable marker, such as an antibiotic resistance gene to facilitate propagation of the plasmid; and (iii) a polylinker site containing several different restriction endonuclease recognition and cut sites to facilitate cloning of a foreign DNA sequence. Yep353, discussed below in the Examples, is one such plasmid vector.

RNA interference (RNAi) is a powerful and robust method for disrupting gene expression. It is based on a highly conserved gene silencing method that uses double-stranded RNA (dsRNA) or single-stranded RNA (ssRNA, see, e.g., Martinez J, et al., *Cell* 110(5):563-74 (2002)) as a signal to trigger the degradation of homologous cellular RNA. The mediators of the sequence-specific degradation are 21- to 23-nucleotide (nt) dsRNA small interfering RNAs (siRNA). Selection of appropriate siRNA sequences and preparation of the siRNA are discussed in detail in Elbashir, S. M. et al., *Methods* 26: 199-213 (2002) and in U.S. Patent Application Nos. 2002/0173478, 2002/0182223, 2002/0183276, 2002/0160393 and 2002/0162126.

Xia et al. describes construction of suitable plasmid containing a gene for expression of an siRNA. That reference also describes recombinant viral vectors and delivery systems The reference describes appropriate expression of an siRNA hairpin which down-regulation of the expression of a target β-glucuronidase gene in mouse brain and liver, thereby providing proof of concept of the usefulness of siRNA technology as a gene therapy for human diseases (Xia et al., *Nature Biotechnology,* 20:1006-1010 (2002)). See also, for example, U.S. Patent Application Nos. 2004/0241854 and 2004/0053876. Vectors for siRNA production are widely available from commercial sources, such as, without limitation, Ambion, Inc. of Austin Tex., Invivogen of San Diego, Calif., and GenScript Corporation of Piscataway, N.J. Vectors containing appropriate promoters, such as Pol III promoters, include for example and without limitation, H1 and U6 promoters and have proven especially useful in producing sufficient quantities of siRNA. A typical siRNA "gene" would therefore comprise an appropriate promoter operably linked to a sequence encoding an siRNA. Ambion's Technical Bulletin #506 ("siRNA Design Guidelines") provides non-limiting examples of siRNA design considerations. Computer software for generating suitable siRNA sequences from, for example and without limitation, a cDNA or ORF sequence also is commercially available.

Using well-established methods for determining effective siRNA sequences, siRNA sequences can be made to silence *R. oryzae* pyruvate dehydrogenase, pyruvate carboxylase and pyruvate decarboxylase. One non-limiting example of an siRNA sequence designed to silence the pyruvate dehydrogenase sequence from *R. oryzae* (FIG. 5) is:

```
Sense
5'-CAGACGAUGACCUUCCUUA       (SEQ ID NO: 12)

Antisense
5'-UAAGGAAGGUCAUCGUCUG       (SEQ ID NO: 13)
```

One non-limiting example of an siRNA sequence designed to silence pyruvate decarboxylase from *Rhizopus oryzae* (GenBank Accession Nos. AF282846 and AF282847) is:

```
Sense
5'-CUUUGAUGUGUUCUUCAAC       (SEQ ID NO: 14)

Antisense
5'-GUUGAAGAACACAUCAAAG       (SEQ ID NO: 15)
```

One non-limiting example of an siRNA sequence designed to silence pyruvate carboxylase from *Rhizopus oryzae* is:

```
Sense
5'-UUGGCCACUCGUGUGAG         (SEQ ID NO: 30)

Antisense
5'-CUCACACGAGUGGCCAA         (SEQ ID NO: 31)
```

In one example, the sense/antisense pairs provided above may be expressed under the control of the $P_{TEF}$ promoter or rRNA cluster promoter in a vector construct, such as for example and without limitation in pPYR225b containing the pyrG gene for selection.

Along with RNAi, antisense RNA is another method of interference with gene function. In antisense technology, RNA complementary to portions of mRNA are introduced into a cell, thereby down-regulating production of the protein product of the mRNA. Unlike RNAi technology, antisense does not completely silence the target gene in most cases. Production of useful antisense constructs and reagents are well within the abilities of those of ordinary skill in the art. At least 450 U.S. patents directed to antisense technologies and applications thereof have been issued to date.

In one example, U.S. Pat. No. 6,838,283 describes antisense modulation of survivin, which is accomplished by providing antisense compounds which specifically hybridize with survivin mRNA. As described in that patent, the specific hybridization of an antisense sequence with its target nucleic acid ("target nucleic acid" encompasses DNA encoding the gene to be modulated), as well as RNA (including pre-mRNA and mRNA) interferes with the normal function of the nucleic acid. The functions of DNA to be interfered with include replication and transcription. The functions of RNA to be interfered with include, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of the gene to be modulated. "Modulation" therefore means either an increase or a decrease in the expression of a gene or its product.

In some embodiments, the target is a nucleic acid molecule encodes, for example, pyruvate dehydrogenase, wherein expression of the molecule shunts pyruvate towards the production of lactate, ethanol and/or fumarate and away from the mitochondrial Krebs cycle. In yet other embodiments, the nucleic acid molecule encodes pyruvate decarboxylase, thereby shunting pyruvate away from ethanol production. Down-regulation of both pyruvate dehydrogenase and pyruvate decarboxylase favors production of fumarate. It is necessary to determine a site or sites within a gene for the antisense interaction to occur such that the desired inhibition of gene expression will result. Within the context of the present invention, an intragenic target for the antisense compound can be the region encompassing the translation initiation or termination codon of the open reading frame (ORF) of the target gene. The ORF can be pyruvate dehydrogenase or pyruvate decarboxylas,e though the ORF of any given gene may be used. The translation initiation codon or "start codon" can be 5'-AUG (in transcribed mRNA molecules; 5'-ATG in the corresponding DNA molecule) or any equivalent, for example, genes having a start codon RNA sequence of 5'-GUG, 5'-UUG, 5'-CUG, 5'-AUA, and 5' ACG. Some genes have two or more alternate start codons, which may also be used to initiate translation. As used herein, "start codon" and "translation initiation codon" include the codon or codons that are used to initiate translation of an mRNA molecule transcribed from a target gene, regardless of the sequence(s) of such codons. It is also known in the art that a translation termination codon (or "stop codon") of a gene may have one of three (RNA) sequences: 5'-UAA, 5'-UAG, and 5'-UGA (i.e., the corresponding DNA sequences are 5'-TAA, 5'-TAG, and 5'-TGA, respectively).

The open reading frame (ORF) or "coding region," which is known in the art to refer to the region between the translation initiation codon and the translation termination codon, is also a region which may be targeted effectively by antisense. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene. Similarly, the 3' untranslated region (3'UTR) may be targeted, e.g., the portion of an mRNA in the 3' direction from the translation termination codon, including nucleotides between the translation termination codon and 3' end of an mRNA or corresponding nucleotides on the gene. The 5' cap of a eukaryotic mRNA comprises an N7-methylated guanosine residue joined to the 5'-most residue of the mRNA via a 5'-5' triphosphate linkage. The 5' cap region of an mRNA is considered to include the 5' cap structure itself, as well as the first 50 nucleotides adjacent to the cap. The 5' cap region may also be a target region.

Once one or more target sites have been identified, oligonucleotides are chosen which are sufficiently complementary to the target; that is, they hybridize sufficiently well and with sufficient specificity, to give the desired effect. As used herein, the term "hybridization" includes hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementarity," as used herein, includes pairing between two nucleotides according to the rules of nucleotide base-pairing (i.e., A:T/U; C:G). For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA may hybridize to each other when a sufficient number of corresponding positions in each molecule are occupied by nucleotides which can hydrogen bond with each other. Thus, "specifically hybridizable" and "complementarity" are terms which are used to indicate a sufficient degree of precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a down-regulation of the expression of the target DNA or RNA, and there is a sufficient degree of complementarity to avoid non-specific binding of the antisense compound to non-target sequences under conditions in which specific binding is desired, that is, under conditions in which the host cell is grown.

A typical antisense construct contains a transcribed portion of the gene to be modulated in antisense orientation. Thus, a typical antisense construct contains a promoter operably linked to a transcribed sequence or a portion thereof as the expressed sequence and a transcription terminator (polyadenylation signal, for example), where the transcribed sequence is oriented in the 3' to 5' direction as compared to the wild-type transcribed sequence.

Eukaryotic cells regulate the expression of genes in many ways. The expression of many eukaryotic genes, however, is controlled primarily at the level of transcription. Promoters can specify the time and manner in which transcription can occur from a particular gene. Therefore, genes can be effectively regulated by strong promoters. Promoters that drive such expression of genes in *Rhizopus* were heretofore not known.

Two *Rhizopus* genes described in public databases include the open reading frames of the translation elongation factor (tef) gene (GenBank Accession No. AF157289) and the ribosomal RNA cluster (rRNA cluster) gene (GenBank Accession No. AB109757). These two genes are expressed at high levels in all eukaryotic cells regardless of growth state or most environmental changes.

The rRNA cluster is a tandem repeat of identical copies of a single gene. These genes, which encode the precursor of the 18S, 5.8S and 28S ribosomal RNAs, are transcribed in the nucleolus by RNA Polymerase I ("Pol I"). Pol I produces a single primary transcript that is processed post-transcriptionally to generate all three RNAs. The promoter region of the rRNA cluster genes spans about 150 base pairs just upstream of (5' to) the transcription initiation start site. These promoters are recognized by two transcription factors, upstream binding factor ("UBF") and promoter selectivity factor-1 ("SL-1"), which bind cooperatively to recruit Pol I to form a transcription initiation complex.

In a particular embodiment, Pol I, along with transcription factors and enhancer elements, binds to the novel promoters of the rRNA cluster genes to regulate expression of the genes. Pol I transcription is localized to the nucleolus and is not inhibited by a-amanitin, a toxic peptide found in certain types of mushrooms. Pol I, alone, cannot initiate or terminate transcription. UBF and SL-1 are necessary and sufficient for full transcription by Pol I. Pol I promoters contain an essential core element immediately surrounding the transcription start site and an upstream control element (UCE) beginning about 100 bases upstream of the start site. UBF binds both the UCE and an upstream portion of the core elements.

Pol I termination of transcription occurs at well-defined sites. The termination sites, called Sal boxes, specifically terminate transcription and comprise an 18 base pair consensus sequence. The Sal box serves as the binding site for transcription termination factor I (TTFI). A single Sal box, which is in the proper orientation and to which TTFI is bound, is sufficient for termination of transcription.

Transcription Elongation Factors (TEFs) are universally conserved proteins that promote the GTP-dependent binding of an aminoacyl-tRNA to ribosomal A-site in protein synthesis. Especially conserved is the N-terminus of the protein containing the GTP binding domain. TEFs are very abundant in cells, comprising about 4-6% of total soluble proteins. Tef genes have been isolated from several organisms. In some organisms, they constitute a multigene family. A number of tef pseudogenes also have been isolated from some organisms. Tef is constitutively expressed, except in aging and quiescent cells. Tef is not known to be regulated by the growth substrates of the host.

Tef promoters are RNA Polymerase II (Pol II) promoters. That is, Pol II is responsible for transcription of the tef gene. Pol II is responsible for synthesizing the precursors to messenger RNA (mRNA) and several small nuclear RNA molecules localizes to the nucleoplasm. Like Pol I, Pol II requires a number of transcription factors to assemble on the promoter to initiate transcription. One of the best characterized Pol II promoter elements is the TATA box. The TATA box includes a specific sequence of nucleotides (TATAAA) located approximately 25 base pairs upstream of the transcription initiation site. It is present in most eukaryotic genes that encode mRNA.

The mRNAs transcribed by Pol II are polyadenylated. Polyadenylation is signaled by a poly (A) addition (AAUAAA) (also known as a poly (A) site) at the 3' end of the processed mRNA. The poly (A) site not only contributes to the addition of the poly (A) tail, but also to transcription termination. Transcription is terminated 200 to 2,000 bases downstream of the poly (A) site.

In particular embodiments, the present invention is directed to isolated polynucleotides that include a promoter from the *Rhizopus* transcription elongation factor (tef) gene and/or from the *Rhizopus* ribosomal RNA cluster (rRNA cluster) gene. Such sequences may be isolated from any species such as *Rhizopus delemar, Rhizopus niveus* or *Rhizopus oryzae.*

In certain embodiments, an isolated polynucleotide may comprise an expressed sequence, such as an ORF, operably linked to the promoter. In particular embodiments, the promoter is operably linked to a protein coding sequence that encodes an enzyme that increases carbon flux to lactic acid or fumarate production. The increase in carbon flux is a result of an increase in the transcription of the gene encoding that enzyme. The protein coding sequence may encode, for example and without limitation, pyruvate carboxylase (e.g., SEQ ID NO: 8 and/or SEQ ID NO: 27), phosphoenolpyruvate carboxylase (e.g., SEQ ID NO:9), pyruvate dehydrogenase (e.g., SEQ ID NO:4 and SEQ ID NO:5), glucokinase, phosphoglucose isomerase, phosphofructokinase, aldolase, triose phosphate isomerase, glyceraldehyde 3-phosphate dehydrogenase, phosphoglycerate kinase, phosphoglycerate mutase, enolase and/or pyruvate kinase. The gene also may encode enzymes that catalyze reactions that regenerate nicotinamide adenine dinucleotide (NAD), for example, lactate dehydrogenase (Idh).

In other particular embodiments, an isolated polynucleotide comprises the nucleotide sequence of base pairs 1-877 or 1-351 of the tef gene promoter of Rhizopus oryzae (FIGS. 2 and 3; SEQ ID NO: 1 and SEQ ID NO: 2, respectively). The isolated polynucleotide can also be the nucleotide sequence of base pairs 1-1043 of the rRNA cluster gene promoter of *Rhizopus oryzae* (FIG. 10; SEQ ID NO: 10; SEQ ID NO: 11) or the core rRNA promoter found therein (SEQ ID NO:11). Alternatively, the isolated polynucleotide can also be fused to a reporter gene, for example, but not limited to, the β-galactosidase (Iac-Z) reporter gene from *Escherichia coli.*

The invention also includes vectors comprising an isolated polynucleotide, wherein the polynucleotide comprises a promoter derived from a *Rhizopus* tef gene or a *Rhizopus* rRNA cluster gene. In certain embodiments, the vectors include a multiple cloning site (MCS) 3' to the promoter, permitting insertion of an expressed sequence into the vector to produce the expression product of the expressed sequence, such as a protein or functional nucleic acid. In yet another embodiment, the vector contains both a promoter derived from a *Rhizopus* tef gene and from a *Rhizopus* rRNA cluster gene, optionally including an MCS 3' to both promoters, permitting insertion of two different expressed sequences in the same vector.

In other embodiments, the vector includes an ORF or coding sequence, with or without introns, for expressing an enzyme that affects carbon flux in a host cell containing the vector. In one embodiment, the expressed sequence encodes an enzyme, such as Idh, that increases carbon flux to lactic acid production during changes in fermentation conditions. The increase in carbon flux to lactic acid would result from an increase in the transcription of the gene. Any Idh gene can be used so long as that Idh accepts pyruvic acid as a substrate. For example, any of the genes encoding bacterial Idh described herein can be used. In one embodiment, the Idh is derived from microorganisms, including but not limited to, *Rhizopus oryzae* (GenBank Accession Nos. AF226154 (IdhA) and AF226155 (IdhB)) or *Lactobacillus casei* (GenBank Accession No. M76708). In yet another embodiment, a host cell comprises a gene in which the tef or rRNA cluster promoter is operably linked to a gene that encodes an enzyme that modifies carbon flux in the host cell, for example and without limitation, the Idh enzyme or any other suitable gene described above and known in the art.

Likewise, a coding sequence for pyruvate carboxylase (e.g., SEQ ID NOS: 6-7 and SEQ ID NO: 26), phosphoenolpyruvate carboxylase (e.g., SEQ ID NO:9) would increase flux of carbon from pyruvate or phosphoenolpyruvate, respectively, to oxaloacetate, resulting in increased production of fumarate through action of malate dehydrogenase and fumarase (see FIG. 1). Further, carbon flux can be changed by changing expression of pyruvate dehydrogenase (e.g., SEQ ID NO:4 and SEQ ID NO:5) in the TCA cycle (see FIG. 1). In yet other embodiments, fumarase (e.g., *R. oryzae* fumR; GenBank Accession No. X78576) may be overexpressed to further increase carbon flux to fumarate. In some other embodiments, the tef and rRNA cluster gene promoters can be fused to a β-galactosidase lac-Z reporter gene from, for example, *Escherichia coli.*

Alternatively, carbon flux can be increased by expressing a gene product that interferes with shunting of pyruvate and its precursors into undesirable metabolic pathways, for example by interfering with the enzymes involved in the conversion of pyruvate into ethanol, or enzymes involved in conversion of 3-phosphoglycerate to glycerol. Genes of interest also include pyruvate decarboxylase genes, such as those of *R. oryzae* (GenBank Accession Nos. AF282846 (pdcA) and AF282847(pdcB)).

In another embodiment, the present invention is directed to a host cell comprising an isolated polynucleotide, wherein the polynucleotide comprises a promoter derived from a *Rhizopus* tef gene promoter or a *Rhizopus* rRNA cluster gene promoter. Microorganisms capable of acting as a host cell include, but are not limited to, fungal cells such as *Rhizopus* ssp., *Saccharomyces* ssp., *Streptomyces* ssp., *Pichia* ssp., *Aspergillus* ssp., and bacterial cells such as *Lactobacillus* ssp., *Escherichia* ssp., *Corynebacterium* ssp., *Brevibacterium* ssp., *Pseudomonas* ssp., *Proteus* ssp., *Enterobacter* ssp., *Citrobacter* ssp., *Erwinia* ssp., *Xanthomonas* ssp., *Flavobacterium* ssp., *Streptococcus* ssp., *Lactococcus* ssp., *Leuconostoc* ssp., and *Enterococcus* ssp.

Nucleic acids can be introduced into cells according to standard methodologies including electroporation, or any other transformation or nucleic acid transfer method known in the art. For example, *R. oryzae* can be transfected by electroporation. *R. oryzae* cells can be permanently transformed by insertion of a gene of interest into the cell by electroporation, so long as the introduced DNA integrates into the host cell genome. This is accomplished, without any intention to be bound by this theory, by homologous recombination of the introduced DNA with the genomic DNA via single or double crossover, or is randomly integrated. The efficiency of transformation is increased when the introduced DNA is linearized and contains non-complementary ends, as is the case when a DNA fragment containing a gene is excised from a plasmid using two different restriction endonucleases which yield non-complementary ends. In such instances, the sequence can be purified from the plasmid backbone prior to transfection. Circularized DNA tends to concatamerize in *R. oryzae*, yielding large, circular extrachromosomal elements, which are eventually lost from the host cell during successive passage of the transfected cell line. Linearized DNA having complementary ends can also re-circularize and concatamerize (not necessarily in that order) and be lost in the same manner as an extrachromosomal element during successive passage of the transfected host cell line.

Host cells may be cultured under any conditions, such as those known in the art. As stated previously, fermentation conditions can affect the flux of carbon in an organism. For example, strong aeration shifts the flux of carbon to production of acetic acid and acetoin, and away from lactic acid production in lactic acid-producing bacteria. Fermentation conditions include, without limitation: the level of aeration, pH, and oxygen saturation level of the medium, as well as the amount of carbon and other growth factors available in the medium. The carbon source can be, for example and without limitation, various sugar alcohols, polyols, aldol sugars or keto sugars, including but not limited to arabinose, cellobiose, fructose, glucose, glycerol, inositol, lactose, maltose, mannitol, mannose, rhamnose, raffinose, sorbitol, sorbose, sucrose, trehalose, pyruvate, succinate or methylamine or other substrates which may be determined by one skilled in the art. As described herein, many organisms will thrive on common growth media. For example and without limitation, *R. oryzae* can be grown in LB (Luria-Bertani) Broth.

Host cells may also be engineered to change carbon flux. Provided in one embodiment is a method of increasing carbon flux to lactic acid comprising culturing in a culture medium a host cell comprising a *Rhizopus* tef gene promoter, a *Rhizopus* rRNA cluster gene promoter, or another promoter operably linked to an Idh coding sequence and recovering lactic acid from the culture medium. Likewise, a method of increasing carbon flux to fumarate is provided comprising culturing in a culture medium a host cell comprising a *Rhizopus* tef gene promoter, a *Rhizopus* rRNA cluster gene promoter, or another promoter operably linked to a pyruvate carboxylase or phosphoenolpyruvate carboxylase coding sequence and recovering fumarate from the culture medium.

In another embodiment, regulation of the expression of a gene product includes providing a coding region that encodes a gene product; operably linking the coding region to an isolated tef gene promoter or an rRNA cluster gene promoter to form a promoter-coding region within genomic DNA in cells wherein the promoter regulates the expression of the gene product in the cells. In some embodiments, the promoter-coding region can be integrated into a genomic DNA in cells wherein the promoter regulates the expression of the gene product in the cells.

In yet another embodiment, the methods of manipulating carbon flux in a cell, such as, without limitation a *R. oryzae* cell, are provided. Referring to FIG. 1, expression of a number of genes may be utilized to engineer a cell with altered metabolic pathways. As discussed in detail above, the expression of certain genes native to the host cell, for example and without limitation, *R. oryzae*, such as Idh (to produce lactate), pyruvate carboxylase (to produce oxaloacetate), fumarase (for example and without limitation, *R. oryzae* fumR, GenBank Accession No. X78576; and Freidberg, et al., Gene. 163(1):139-44(1995)) (to produce fumarate), or, glycerol-3-phosphate dehydrogenase (to produce glycerol) can be increased by the methods described herein. In a similar manner, genes not native to the host cell may be introduced into the host cell under constitutive or inducible control of a promoter with the goal of increasing carbon flux to a desired end-product metabolite, such as fumarate. In one example for production of fumarate, alfalfa (*Medicago sativa*) phosphoenolpyruvate (PEP) carboxylase is introduced into an *R. oryzae* cell to shunt carbon from PEP directly to oxaloacetate, preventing diversion of pyruvate to the Krebs cycle and to ethanol and lactate production (see FIG. 1, dotted line).

In a further example, antisense or RNAi technologies may be used alone, or in combination with increased gene expression of lactate dehydrogenase, PEP carboxylase or pyruvate carboxylase to further divert carbon from one metabolic pathway to another. It is noted that under some conditions, complete gene silencing may prevent sufficient cell culture growth unless a specific metabolite is provided in the culture medium (auxotroph). Thus, production of a bradytroph may be optimized in many instances with antisense technology or RNAi technology. One particular candidate enzyme for antisense or RNAi targeting is pyruvate dehydrogenase, which converts pyruvate to acetyl coenzyme A (acetyl-coA), which donates its acetyl group to oxaloacetate to form citrate in the citric acid cycle, resulting in overproduction of fumarate. A cell co-transfected with genes for overexpressing pyruvate carboxylase and for down-regulating expression of pyruvate dehydrogenase is expected to shunt carbon to fumarate. Use of an inducible promoter, such as the TET-ON or TET-OFF promoter (BD Biosciences Clontech) can avoid the growth inhibition connected with the silencing of pyruvate dehydrogenase. In such a case, the cells can be grown to a desired density in culture before pyruvate dehydrogenase (and the Krebs cycle) is silenced.

Another embodiment includes a method to construct selectable markers for more efficient metabolic engineering of a microorganism, comprising introducing into a lactose auxotroph host cell a nucleic acid comprising lac-Z (encoding β-galactosidase) operably linked to a promoter derived from a *Rhizopus* tef gene or a *Rhizopus* rRNA cluster gene. The nucleic acid can be a vector containing a second gene for expression in the host cell. The ability of a transfected host cell to grow on lactose would facilitate selection of transfected host cells.

In yet an additional embodiment, the compositions of the invention may be produced at a first geographic location and transported or shipped to a second geographic location. For instance, a facility at the first geographic location may be able to produce a product more economically than a facility at the second location due to various factors. The factors may include, inter alia, lower costs of materials (i.e., the mannitol), lower costs of energy (i.e., electricity or gas), lower costs of labor (i.e., wages paid to employees), lower costs of environmental controls or effects, or any other requirement for production of the compositions of the invention. Further, a certain product may be well suited for production in the first geographic location and desired, but not produced well, in the second geographic location. As a non-limiting example, residents of Alaska may desire bananas produced in Central America. Thus, the costs of producing the products in a first geographic location may be less than the costs of producing the products in a second geographic location, resulting in the production costs of the product being less in the first geographic location.

In such an instance, the compositions of the invention may be produced at the first geographic location and shipped to the second geographic location, such as by transport over water with ships or barges, trucking, flying, or other means of transportation. The geographic location may be a county, a state, a country, a continent and/or combinations of any thereof. In this manner, the product may be produced in a first country and transported and/or sold in a second country.

The following are examples of methods and compositions of the invention. The examples are not meant to limit the scope of the invention, as defined by the claims.

Example 1

Isolation of the tef Gene Promoters and *Rhizopus* ETS Region

Promoter regions of the tef and regions of the External Transcribed Sequences (ETS) were cloned by cutting total genomic DNA of *R. oryzae* with restriction endonuclease. The DNA was ligated to adapters (LA PCR in vitro Cloning Kit, Takara Mirus Bio, Inc. of Madison, Wis., see also U.S. Pat. No. 5,436,149) and the promoter regions were amplified with the polymerase chain reaction using one primer complementary to known gene sequences and one primer complementary to the adapter, as follows:

```
C2 cassette primer
                                          (SEQ ID NO: 16)
5'-CGTTAGAACGCGTAATACGACTCACTATAGGGAG (Takara);

TEF reverse primer
                                          (SEQ ID NO: 17)
5'-GTAATCATGTTCTTGATGAAATCACGG;

ETS reverse primer
                                          (SEQ ID NO: 18)
5'-GATTCACTGAATATGCAATTCACACTAG.
```

Three products were amplified using the respective primers. The resulting products were a 351 base pair tef polynucleotide (FIG. 2), a 877 base pair tef polynucleotide (FIG. 3) and an ETS polynucleotide (FIG. 4). The 351 base pair tef polynucleotide (FIG. 2) was inserted into the multiple cloning site to the *E. coli* β-galactosidase lac-Z reporter gene of YEP353 plasmid (GenBank Accession No. U03500).

Yep353 (GenBank Accession No. U03500) is a shuttle vector that has origins of replication for bacteria and yeast. It has a multiple cloning site situated in front of the reporter gene lacZ. When a piece of DNA that responds to transcriptional machinery is cloned into it in the proper direction, the lacZ gene is expressed and β-galactosidase activity is quantifiable. If nothing is cloned in the MCS, or if the insert DNA in the MCS does not behave as a promoter in these organisms, then no activity is expressed.

The 351 base pair tef polynucleotide showed strong expression in *E. coli* and yeast. *E. coli* cultures containing the YEP353 PTEF:lacZ plasmid were grown on LB plates containing X-gal. The strong promoter capability of tef in *E. coli* and yeast indicates that it has a broad host cell tropism, making the promoter useful in a large variety of organisms.

Example 2

Effect of Promoter Constructs on Lactic Acid Production

In another construct, the 351 base pair tef polynucleotide is fused to Idh genes from *Rhizopus oryzae* and *Lactobacillus casei*. The effect of over-expression of these genes on lactic acid production can be evaluated.

Example 3

Reporter-Promoter Constructs

In another construct, the 351 base pair tef polynucleotide was fused to the β-galactosidase lac-Z reporter gene from *Escherichia coli*. This construct can be used to select for transformants that show a gain of ability to use lactose as a carbon source and can facilitate more effective metabolic engineering. With this construct, an auxotroph will not need to be created before genetic engineering begins.

Example 4

Construction of $P_{TEF}$:pyrC:$T_{PGK}$ Plasmid—Using Ligation Independent Cloning TEF promoter (PTEF) is amplified by PCR using primers that will create a smal site on the 5' end and add the ATG codon and 10 bases of the 5'end of pyruvate carboxylase to the 3' end of the amplicon (Product 1=Smal-PTEF-ATG-10 by of pyrC). Pyruvate carboxylase (pyrC) from cDNA clone is amplified by PCR using primers that will add 10 base pairs of the 3' end of PTEF and the ATG codon to the 5' end of the amplicon and an spel restriction site to the 3' end of the amplicon (Product 2=10 bp of PTEF-ATG-pyrC-Spel). PCR products 1 and 2 are mixed with $P_{TEF}$ smal forward primer and pyrC spel reverse primer. $P_{TEF}$:pyrC product is amplified by PCR. The smal-PTEF:pyrC-spel, PCR product 3, and pyr225b vector are cut with small and spel and ligated. *S. cerevisiae* PGK terminator ($T_{PGK}$, terminator on vector Ylp-DCE1 GenBank—AF039102) is amplified by using primers that will introduce spel and sacl restriction sites. Pyr225b containing $P_{TEF}$:pyrC and the amplified Tpgk terminator are cut with spel and sacl and ligated. pPYR225B vector (pBluescript KS-containing a 2.25 Eco RI genomic *Rhizopus* fragment (GenBank AF497632) contains the pyrG gene.

The resulting plasmid is linearized within the pyrG gene to facilitate Type I or single crossover into genomic DNA, and used to transform a pyrG deletion mutant generated from *Rhizopus oryzae* wild-type strain ATCC 10260 (*Rhizopus oryzae* NRRL 1526).

Example 5

Construction of $P_{TEF}$:pepc:$T_{PGK}$ Plasmid—Using Ligation Independent Cloning The plasmid construction outlined in Example 5 above can be used to build a similar construct containing the alfalfa PEP carboxylase coding sequence (see U.S. Pat. No. 6,599,732, SEQ ID NO: 1). The pyrC fragment of $P_{TEF}$:pyrC:$T_{PGK}$ can be excised with restriction endonucleases sbfl and apal and replaced with a PEP carboxylase ORF that has been PCR-modified to contain sbfl and apal restriction sites.

Example 6

*Rhizopus Oryzae* Pyruvate Carboxylase

The isolation and characterization of *Rhizopus oryzae* genomic and cDNA is described herein. Both the nucleic acid molecule and the encoded pyruvate carboxylase protein are provided. The properties of this enzyme and potential application for fumaric acid and during lactic acid production are discussed.

As part of an effort to characterize the genes encoding the enzymes in the pathway leading to the synthesis of lactic acid, malic acid, fumaric acid, ethanol and glycerol during fermentation, a pyruvate carboxylase gene was isolated from *R. oryzae* and the relatedness of its deduced protein to other known orthologs was studied. Two degenerate oligonucleotide primers were synthesized based on conserved regions pyruvate carboxylase-related amino acid sequences of *A. bisporus* (GenBank Accession No.: AJ276430), *A. terreus* (GenBank Accession No.: AF097728), *P. pastoris* (GenBank Accession No.: Y11106), and *S. pombe* (GenBank Accession No.: D78170,). Amplification by polymerase chain reaction (PCR) with *R. oryzae* genomic DNA as template yielded a product of the predicted size (648 bp). Additional PCR reactions using gene-specific and degenerate primers were used to isolate the pyruvate carboxylase gene and cDNA fragments from *R. oryzae*. The cDNA, genomic DNA, and encoded amino acid sequence of the protein, were described (SEQ ID NOS:6-8 and SEQ ID NOS: 26-27) (FIGS. 6 and 11).

*Rhizopus oryzae* strain 28.51 was maintained on YM agar plates (per liter: 3 g yeast extract, 3 g malt extract, 5 g peptone, 10 g dextrose, and 20 g agar). The fungus was grown in YML liquid media (per liter: 3 g yeast extract, 3 g malt extract, 5 g peptone, and 10 g dextrose) at room temperature with shaking (100 to 150 rpm) or YM agar plates at 30° C.

DNA and total RNA were extracted from frozen spores (−80° C.) of *R. oryzae*. Genomic DNA was isolated using the Omniprep™ purification system (Geno Technology, Inc., St. Louis, Mo.) or by a CTAB buffer (100 mM Tris-HCl, pH 7.5, 1% mixed alkyltri-methyl ammonium bromide (Sigma, St. Louis, Mo.), 0.7M NaCl, 10 mM EDTA 1% β-mercaptoethanol (v/v)) plus 0.03% proteinase K. The frozen spores were ground by mortar and pestle and extracted in the CTAB buffer followed by incubation at 65° C. for 30 min. One volume of chloroform/isoamyl alcohol (24:1) was added, gently mixed for 5 min., and centrifuged at 3,000 rpm for 20 min. The supernatant was removed and a 2/3 volume of 2-propanol was added and recentrifuged as above. The precipitated DNA was rinsed with 75% ethanol and suspended in 0.5 ml sterile water. Contaminating RNA was removed by addition of 5 μl of 10 mg/ml RNAse A and incubation at 37° C. for about 30 min.

Total RNA was isolated using RNAqueous™ Kit (Ambion, Inc., Austin, Tex.) and mRNA was purified from the total RNA using the PolyATtract™ mRNA Isolation Systems (Promega Corporation, Madison, Wis.). The methods used for DNA and RNA electrophoresis have been described elsewhere (Sambrook, J., Fritsch, E. F., and Maniatis, T., in Molecular Cloning: A Laboratory Manual. Cold Spring Harbor Laboratory Press, NY, Vol. 1, 2, 3 (1989)).

PCR was performed in a GeneAmp PCR System 9700™ (Applied Biosystems, Foster City, Calif.) using Taq DNA polymerase (Life Technologies, Gaithersburg, Md.) and two degenerate primers based on conserved amino acid sequences of pyruvate carboxylase homologs from *Aspergillus agricarus, A. terreus, Pichia pastoris*, and *Schizosaccharomyces pombe*. Forward primer 5' CARAGRAGRCAYCARAARGT 3' (SEQ ID NO:19) is based on the amino acid sequence "QRRHQKV," and reverse primer 5' TCRTCDATRAANGTNGTCCA 3' (SEQ ID NO:20) is based on the amino acid sequence "WTTFIDD" (where Y=T or C; R=G or A; D=A, G or T; N=A, T, G, or C) (SEQ ID NO:21). The degenerate primers were used in Touchdown PCR (Don, R. H., et al., *Nucleic Acids Res.* 19:4008 (1991)) to amplify a 648-bp fragment from *R. oryzae* genomic DNA. Touchdown PCR was performed under the following conditions: initial denaturation at 94° C. for 3 min; 38 cycles of denaturation, 94° C. for 30 sec; annealing for 30 sec; and polymerization at 72° C. for 2 min. The annealing temperature ranged from 55° C. to 45° C. with a decrease of 1° C. every three cycles. This was followed by 14 cycles of denaturation at 94° C. for 1 min; annealing at 45° C. for 30 sec.; and polymerization at 72° C. for 2 min. The PCR product was cloned into pGEM T-easy™ vector (Promega, Madison, Wis.). Additional PCR products were isolated using pyruvate carboxylase (PYC) gene-specific primers, genomic DNA or cDNA and other degenerate primers.

The 5' end of the pyruvate carboxylase (PYC) cDNA was determined using the GeneRacer™ kit, following the instructions of the manufacturer (Invitrogen Corporation, Carlsbad, Calif.). A PYC-specific oligonucleotide of sequence 5'-CCAATACGACCGAGTTGATAGGATTCAT-3' (SEQ ID NO:22) was used to prime first-strand cDNA synthesis, which was then amplified by PCR using a nested primer of the sequence 5'-GCATAGATAATGTATCTTCATGA-3' (SEQ ID NO:23).

Automated fluorescence DNA sequencing was done at the W. M. Keck Center for Comparative and Functional Genomics Facility, University of Illinois at Urbana-Champaign. Sequence data were analyzed with DNASTAR™ software (DNASTAR, Inc., Madison, Wis.).

Figure 8:
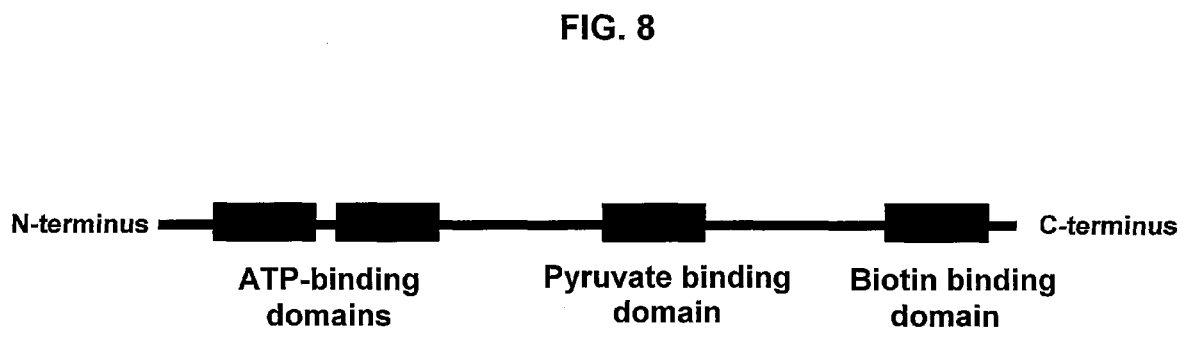
Figure 9:
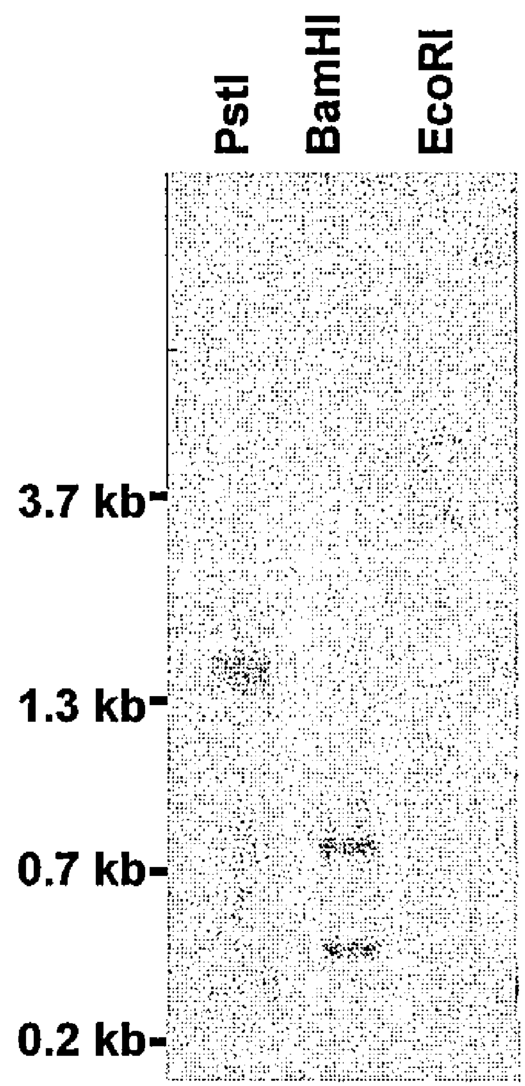
FIG. 9 is a Southern blot of total genomic DNA from *R. oryzae* digested with restriction enzymes PstI, BamHI, or EcoRI showing relative copy numbers of the pyruvate carboxylase (pyrC) containing plasmid.

The open reading frame of the product of PYC, PYCp, is 1178 amino acids and has a molecular mass of 130 kD. PYCp has ~61 to 67% overall identity with *S. cerevisiae* (Morris, C. P., et al., *Biochem. Biophys. Res. Commun.* 145:390-396 (1987)); *Aspergillus niger* (Panneman, H., Ruijter, G. J. G., Van den Broeck, H. C. and Visser, J., unpublished); *A. terreus* (Li, Y. F., Chen, M. C., Lin, Y. H., Hsu, C. C. and Tsai, Y. C., unpublished); *P. pastoris* (Menendez, J., et al., *Yeast* 14:647-654 (1998)); and *S. pombe* (Saito, A., et al., unpublished) pyruvate carboxylase proteins. The similarity is very strong throughout the protein sequence (FIG. 8). The two ATP and biotin binding domains are 100% conserved, while the pyruvate binding domain is 89% conserved among these fungal proteins (FIG. 8), like its yeast homolog (Lim, F., et al., *Arch. Biochem. Biophys.* 258:259-264 (1987)). The PSORT program (Nakai, K., et al., *Genomics* 14:897-911 (1992)) strongly predicts the subcellular localization of *R. oryzae* pyruvate carboxylase to the cytoplasm. The computed probability of PYCp having a cytoplasmic localization is 78%. Hybridization of a PYC probe to a blot of *R. oryzae* genomic DNA digested with different restriction enzymes (PstI, BamHI, or EcoRI) resulted in a single band in one case and multiple bands in the others. Preliminary data indicates that there may be a single copy of this pyruvate carboxylase gene in *R. oryzae* (FIG. 9).

The production of fumaric acid by *R. oryzae* has been shown to result from a cytosolic pathway during which pyruvate is converted to oxaloacetate by pyruvate carboxylase (Osmani and Scrutton, *Ann NY Acad Sci* 447: 56-71 (1985)). Therefore, this gene expression can be enhanced by introducing multiple copies or expressing it from a strong promoter to increase fumaric acid production. Moreover, the disruption of this gene can also lead to the reduction of fumaric acid produced during lactic acid production by *R. oryzae.*

Example 7

Cloning of Pyruvate Carboxylase from *Rhizopus Oryzae* NRRL Strain 1526

Mycelia were harvested 48 hours after inoculation into fumaric acid production media. Total RNA was isolated from the *Rhizopus oryzae* NRRL strain 1526 using an RNAqueous™ Kit as set forth in Example 6. The total RNA was used to generate cDNA using a GeneRacer™ kit as set forth in Example 6. One pyruvate carboxylase specific primer 5'-ATAACGATGCCTGCTGCACC-3' (SEQ ID NO: 28) and a GeneRacer™ kit 3' nested oligo dT primer 5' CGCTACGTAACGGCATGACAGTG 3' (SEQ ID NO: 29) were used to PCR amplify the pyrC cDNA. The pyrC-specific primer (SEQ ID No: 28) was designed from the pyrC genomic sequence cloned from the lactic acid producing *Rhizopus oryzae* NRRL 395. Once amplified, the putative pyrC cDNA was purified using Wizard® SV Gel and PCR clean-up system (Promega Corporation, Madison, Wis.). PCR-Script™ AMP Cloning kit (Stratagene, La Jolla, Calif.) was used to clone the amplicon into pPCRScript vector. The pyrC cDNA was then subcloned into pPUC19, sequenced, and transformed into *E. coli* strain JCL1242 (a phosphoenolpyruvate carboxylase knockout) (Gokarn et al., Appl. Microbiol. Biotech., 2001 (56): 188-195). The putative pyrC cDNA complemented the phosphoenolpyruvate (PEP) carboxylase deficiency to allow growth on glucose. After demonstrating growth on glucose by the PEP carboxylase deficient organism, the pyrC cDNA was subcloned (both by ligation dependent and ligation independent methods) into a variety of other vectors.

Example 8

Cloning and Construction of $P_{rRNA\ cluster}$ Plasmid

A search of GenBank for the 28S-IGS-18S region for yielded a *Rhizopus oligosporus* sequence (GenBank Accession No. AY847625). A cloned a portion of the 18S gene upstream from the GenBank sequence ab109757 was used for the search. Two putative rRNA clusters were found (AY847625 and and other fungal 5S sequences). These were aligned with the two putative rRNA clusters to identify the promoter region of interest. Thus, by using GenBank sequence AY847625 from *R. oligosporus* to blast the public but un-annotated genome sequence for *R. oryzae* (Broad Institute), the putative desirable 18S promoter sequence of NTS2 was identified. Primers were designed against this sequence and a fragment isolated. The forward primer was (EcoRI restriction site in italics):

TC*GAATTC*GGGGGACCACATGGGAATAC (SEQ ID NO: 24)

The reverse primer was (PstI restriction site in italics):

TGG*CTGCAG*GTCATGTTGGCAGGATC (SEQ ID NO: 25)

Using the methods described in Example 1, the isolated fragment (SEQ ID NO:10) was operably linked in frame to the lacZ expression marker and cloned into a Yep353 plasmid. Expression of lacZ was detected in *E. coli*, but not yeast. This is as predicted since in eukaryotes the rRNA core promoter (e.g., SEQ ID NO:11) recruits polymerase I (Pol I) and Pol I transcripts do not have a 7-methylguanylate cap nor are they recruited to ribosomes for translation. Conversely, in prokaryotes, transcription and translation are simultaneous and capping is not present so translation of the protein occurs. Thus, the rRNA promoter can be used as a promoter in eukaryotes for transcription of antisense or RNAi constructs.

Having now fully described this invention, it will be understood to those of ordinary skill in the art that the same can be performed within a wide and equivalent range of conditions, formulations and other parameters without affecting the scope of the invention or any embodiment thereof. It will be appreciated by those skilled in the art that changes could be made to the embodiments described herein without departing from the broad concept of the invention. It is understood, therefore, that this invention is not limited to the particular embodiments disclosed, but is intended to cover modifications that are within the spirit and scope of the invention as defined by the claims.

What is claimed is:

1. An isolated or recombinant polynucleotide comprising a sequence selected from the group consisting of:

a polynucleotide sequence that encodes a protein that is at least 95% sequence identical to SEQ ID NO: 8, the protein having pyruvate carboxylase activity;

a complementary polynucleotide sequence which is fully complementary to the polynucleotide sequence that encodes the protein that is at least 95% sequence identical to the SEQ ID NO: 8; and a sequence that hybridizes to the complementary polynucleotide sequence under conditions of 0.2×SSC at 65° C.

2. The isolated or recombinant polynucleotide of claim 1, wherein the sequence is the polynucleotide sequence that encodes the protein that is at least 95% sequence identical to SEQ ID NO: 8.

3. The isolated or recombinant polynucleotide of claim 1, further comprising a promoter operably linked to the sequence.

4. A vector comprising the isolated or recombinant polynucleotide of claim 1.

5. A vector comprising a promoter and a polynucleotide sequence encoding a polypeptide having at least 95% sequence identity to the amino acid sequence of SEQ ID NO: 8, said polypeptide having pyruvate carboxylase activity.

6. An isolated recombinant host cell comprising the vector of claim 5.

7. The isolated recombinant host cell of claim 6, wherein the host cell is of a genus selected from the group consisting of *Rhizopus, Saccharomyces, Streptomyces, Pichia, Aspergillus, Lactobacillus, Escherichia coli, Corynebacterium, Brevibacterium, Pseudomonas, Proteus, Enterobacter, Citrobacter, Erwinia, Xanthomonas, Flavobacterium, Streptococcus, Lactococcus, Leuconostoc*, and *Enterococcus*.

* * * * *

SEQUENCE LISTING

<160> NUMBER OF SEQ ID NOS: 31

<210> SEQ ID NO 1
<211> LENGTH: 866
<212> TYPE: DNA
<213> ORGANISM: Rhizopus oryzae

<400> SEQUENCE: 1
gaattctata ataaacagcg atatcaagac agatcaaaac tcctggacga cttgaatcac 60
aaacatactc ttggaaacat gcatcatact aatgcatgct gaaaggcact tcagtagttc 120
aaaagatatt tgttaccgcc actcattaaa ttaaatttcg accaaaacga tgctaaaaaa 180
atttttatct tttgttcctg aaaatttttt aaaggtaacc aatagcagac tattccgaaa 240
ttgaattgac tagagaaaaa caacctttat gacagcaaca aagtagctta taaccaagtc 300
gtgtgttatt tgagtataaa aacaattttt ttttccatat tggttttcta aaccatagtt 360
ctcattcgtt acaaggataa agactacttt ggcggagtaa aaagaaaaaa gcaaaacaga 420
gagtctccga ataaaataga agcatttcga aaaaagtttg cttcacttaa aataacagta 480
aacgtaaagc aaacattgtg gctgtcatac attgctcatt ttaggatcca tttccactgt 540
gagaatggac aagaaagaaa aaggtaaaag aacaacaaag agtaactcct aaagtaaaac 600
ttttgttgtg caacccaatc aagtcatgcc gttgtgacca tttccgcggt ggcttttcac 660
gcggaacaag aaaaaaaaat tttaaaacga gaaatttttt tgttattgtt tgttttctct 720
tttttctgtt actttataaa cttcctcaag taaggatact cactacgcca tccaacatgt 780
actaattcta ttcatcatag ccatgggtaa agataagact aacatcagta ttgttgtcat 840
cggtcacgtc gattccggta agtcta 866

<210> SEQ ID NO 2
<211> LENGTH: 340
<212> TYPE: DNA
<213> ORGANISM: Rhizopus oryzae

<400> SEQUENCE: 2
tccatttcca ctgtgagaat ggacaagaaa gaaaaaaata aaagaacaac aaagagtaac 60
tcctaaagta aaacttttgt tgtgcaaccc aatcaagtca tgccgttgtg accatttccg 120
cggtggcttt tcacgcggaa caagaaaaaa aaattttaaa acgagaaatt tttttgttat 180
tgtttgtttt ctcttttttc tgttacttta taaacttcct caagtaagga tactcactac 240
gccatccaac atgtactaat tctattcatc atagccatgg gtaaagataa gactaacatc 300
agtattgttg tcatcggtca cgtcgattcc ggtaagtcta 340

<210> SEQ ID NO 3
<211> LENGTH: 1033
<212> TYPE: DNA
<213> ORGANISM: Rhizopus oryzae
<220> FEATURE:
<221> NAME/KEY: misc_feature
<222> LOCATION: (636)..(636)
<223> OTHER INFORMATION: n is a, c, g, or t

<400> SEQUENCE: 3
agcttgaatg tgttagcatg gaataatgaa atatgacttt agtcctattt tcgttggttt 60
aggtacttca gtaatgatga atagaaacgg ttaggggcat ttgtatttgg tcgctagagg 120
tgaaattctt ggattgaccg aagacaaact actgcgaaag catttgaccc gggacgtttt 180

-continued

```
cattgatcaa ggtctaaagt taagggatcg aagacgatta gataccgtcg tagtcttaac    240
cacaaactat gccgactaga gattgggcgt gtttattatg actcgctcag catcttagcg    300
aaagtaaagt ttttgggttc tggggggagt atgggacgca aggctgaaac ttaaaggaat    360
tgacggaagg gcaccaccag gagtggagcc tgcggcttaa tttgactcaa cacggggaaa    420
ctcaccaggt ccagacatag taaggattga cagattgaaa gctctttcta gattctatgg    480
gtggtggtgc atggccgttc ttagttcgtg gagtgatttg tctggttaat tcccgataac    540
gaacgagacc ttattctgct aattagacag gctaactctt tcgggttggt ttatatttaa    600
tatttaactg gcttcttaaa gaaactatcg gcttcnagcc gaaggaagtt ttaggcaata    660
acaggtctgt gatgccctta gatgttctgg gccgcacgcg cgctacactg atgaagtcag    720
cgagtttata accttggccg gaaggtctgg gtaaactttt gaaacttcat cgtgctgggg    780
atagagcatt gtaattattg ctcttcaacg aggaattcct agtaagcgca agtcatcagc    840
ttgcgttgat tacgtcccct gccctttgta cacaccgccc gtcgctacta ccgattgaat    900
ggttatagtg agcatatggg atcagtagga tttgactggc aacagtcatt tcctgcagag    960
aactatggca aactaggcta tttagaggaa gtaaaagtcg taacaaggtt tccgtaggtg   1020
aacctgcgga agg                                                      1033
```

<210> SEQ ID NO 4
<211> LENGTH: 1575
<212> TYPE: DNA
<213> ORGANISM: Rhizopus oryzae

<400> SEQUENCE: 4

```
gaaaccctat ctttctcaac agacgatgac cttccttaca gctattcacc gtatggctcc     60
tgctgccatt aagcaggctg ctactgcctc tgttaagccc actgctgttg ctttcactca    120
aaagcgtttc aactccactg gctctgaggt atagaaaaaa aaaaaaatag ataatgtaaa    180
cttatatccc ccggctttta gatgactgtt cgtgaagctt taaaccaagc tttggaagaa    240
gaaatgatca aggatgaaac agtctacatc ctcggtgaag aagttgctca atacaacggt    300
gcttataagg tattttatcg cgtattttat ttgtaggggt attatgggat tattcgggaa    360
aaagcgaaaa aagattgggg tgacgaaaag ggaggagttt aaaaagaaaa ctttttttaat   420
ttttttcca ttgcctaggt gaccaaaggt ttattagaca agtttggtgc taagcgtgtg    480
atcgataccc ccattaccga aatgggtttt gctggtattg ctgttggttc tgccttcagc    540
ggtttgaagc ctgtttgtga attcatgact ttcaattttg ccatgcaggt aaatacagaa    600
attttttcac taaaaaaata tattcacagt gtttgtatta ggctattgat caaatcgtta    660
actctgctgc caagacctac tacatgtctg gtggtggtgt caagtgtcct atcgttttcc    720
gtggcctacc gtgctgctgc tggtgtccgg ccccaacctc tcaagattct ctgcctggat    780
gggtctgttc ccgcttgaag gtccctttc ctggaccctt gaagatgcta aggttgttga     840
aggctgccat tcgtgacccc aaccctgttg tcttccttga aaacgaactc gaatatggtg    900
tctcttaccc tgtctcttcc gaagctcttt cttctgactt tgttctccct atcggtaagg    960
ccaagattga acgtgaaggt aaggatgtga ctatcgtttc ccactctcgt cctgttggtt   1020
tcgccatgaa ggccgctgaa cttttggcca aggatggtat ttctgctgaa gttatcaact   1080
tgagatctat caagcctctt gatgttgaca ctatcatcaa gtccgtcaag aagaccaacc   1140
accttatctc tgttgaaaac gcctgggcct ctttcggtgt cggttctgaa attgctgctc   1200
```

```
aagttatgga aagtaagtag tatagattta aaaagatgca tttgtacaag tatagatgtt   1260

aatttctgtt aaaaggtgag gctttctggc acttggatgc tcctatgagc cgtgtcactg   1320

gtgctgatgt tcccactccc tatgctgcca accttgaagc ccttgctttc cctgatgaac   1380

acgtcattgc taaggctgtt agagataact tggacaaaaa agttggtttc taaaaaggat   1440

tataattttt tactattcca ataatatttg ttttttttctt ctactttttt ccctctctct   1500

acacacatct ttttctttta tagattggag atcaagaaaa aaaaaaccag caaaatcaaa   1560

agaagtattt gatgt                                                    1575
```

<210> SEQ ID NO 5
<211> LENGTH: 1287
<212> TYPE: DNA
<213> ORGANISM: Rhizopus oryzae

<400> SEQUENCE: 5

```
gaaaccctat ctttctcaac agacgatgac cttccttaca gctattcacc gtatggctcc     60

tgctgccatt aagcaggctg ctactgcctc tgttaagccc actgctgttg ctttcactca    120

aaagcgtttc aactccactg gctctggaaa tgatcaagga tgaaacagtc tacatcctcg    180

gtgaagaagt tgctcaatac aacggtgctt ataaggtgac caaaggttta ttagacaagt    240

ttggtgctaa gcgtgtgatc gatacccccca ttaccgaaat gggttttgct ggtattgctg    300

ttggttctgc cttcagcggt ttgaagcctg tttgtgaatt catgactttc aattttgcca    360

tgcaggctat tgatcaaatc gttaactctg ctgccaagac ctactacatg tctggtggtg    420

gtgtcaagtg tcctatcgtt ttccgtggcc taccgtgctg ctgctggtgt ccggccccaa    480

cctctcaaga ttctctgcct ggatgggtct gttcccgctt gaaggtccct tttcctggac    540

ccttgaagat gctaaggttg ttgaaggctg ccattcgtga ccccaaccct gttgtcttcc    600

ttgaaaacga actcgaatat ggtgtctctt accctgtctc ttccgaagct ctttcttctg    660

actttgttct ccctatcggt aaggccaaga ttgaacgtga aggtaaggat gtgactatcg    720

tttcccactc tcgtcctgtt ggtttcgcca tgaaggccgc tgaacttttg gccaaggatg    780

gtatttctgc tgaagttatc aacttgagat ctatcaagcc tcttgatgtt gacactatca    840

tcaagtccgt caagaagacc aaccacctta tctctgttga aaacgcctgg gcctctttcg    900

gtgtcggttc tgaaattgct gctcaagtta tggaaagtga ggctttctgg cacttggatg    960

ctcctatgag ccgtgtcact ggtgctgatg ttcccactcc ctatgctgcc aaccttgaag   1020

cccttgcttt ccctgatgaa cacgtcattg ctaaggctgt tagagataac ttggacaaaa   1080

aagttggttt ctaaaaagga ttataatttt ttactattcc aataatattt gttttttttct   1140

tctacttttt tccctctctc tacacacatc tttttctttt atagattgga gatcaagaaa   1200

aaaaaaacca gcaaaatcaa aagaagtatt tgatgtaaaa aaaaaaaaaa aaaaaaaaaa   1260

aaatttccca ctctcgtcct gttggtt                                       1287
```

<210> SEQ ID NO 6
<211> LENGTH: 3853
<212> TYPE: DNA
<213> ORGANISM: Rhizopus oryzae

<400> SEQUENCE: 6

```
ggacactgac atggactgaa cgagtagaaa cgactggagc ttttggacac tgacatggac     60

tgaaggagta gaaacgactg gagcacgagg acactgacat ggactgaagg agtagaaaat    120

ttctttcttg tatttttttt taaacacaca cacacttaaa taataacgat gcctgctgca    180
```

-continued

```
ccagtacgtg aacattcagt ggataccatt cgcagaaata gcgaagtgat gggtaacctg    240
agaaaattga tggtggttaa tcgtggtgaa attgctatac gtgtctttcg tacagctcat    300
gaactctcta tgaagacagt agctattttc tctcatgaag atagattatc tatgcacaga    360
tataaggctg atgaatccta tcaactcggt cgtattggtc aatacacacc tgtaggtgat    420
tatttggcac aagatgaagt cgttcgaatc gcaaaggaac gtggtgttag catgattcat    480
cctggttatg gtttcttatc tgaaaatgct gaattcgctc gcaaggtgga agctgcagga    540
gtcactttca ttggtccctc tcctgatgtc attgaaagtt taggcgataa aacaaaagcc    600
agaacgattg ccatgcagtg tgaagtccct gttgtccctg gtacacctgg accagtcagt    660
gaatataaag aggccctgaa ctttatcaaa gaatatggtt ttcctattat catcaaggct    720
gccatgggtg gtggtggtcg tggtatgcgt gtggttcgtg acgaagccag tctagaggac    780
gcgtttaccc gtgcgaaatc tgaagcttta gctgcctttg gtgatggtac tgtcttcatc    840
gaacgtttcc ttgataagcc tcgtcatatt gaggttcaat tgttggcaga tcgtgcaggt    900
aacgtagtcc atctctttga acgtgattgg tctgtgcaac gtcgtcacca aaaggtcgta    960
aaaattgcac ctgccaaaaa cttggataac aaggtacgtg aggccatctt gaacgatgcg   1020
atcaagattg ccaaggctgt aaagtacaag aacgctggta ctgcagaatt cttggttgat   1080
aaccaaaacc gtcactactt tatcgaaatc aatcctcgta tccaagtcga acacaccatc   1140
acagaagaaa tcacaggtat cgatatcgtt gccgctcaaa ttcagatcgc tgctggtgcc   1200
ctcttgcctc aattgggtct tacccaacaa cgtatccgtc aacgtgggtt cgcgatccag   1260
tgtcgtgtga caaccgagga ccccgaaaag aatttccagc ctgacacggg taagatcgaa   1320
gtttaccgtt cctctggtgg taacggtgtt cgtctggatg gtggtgctgg ttacgcaggt   1380
gctatcatta cccctcatta tgattcactt ttggtcaaag tctcttgttc tggatccacc   1440
tacgaagtcg ctcgtcgaaa gatcgttcgt gccttggtcg aattcagaat tcgtggcgtc   1500
aagaccaata tccccttctt acaacgtctc ttgacccatg atactttcat caacggtaac   1560
tgctggacaa ctttcattga tgatactccc gatcttttcc gtcttgttca attccaaaac   1620
cgtgctcaaa gacttttggg ttaccttggt gatgtcgtcg tcaatggttc tcaaatcaag   1680
ggtcaaatgg gtgatcctat tctgaacaag agatcgaaat tcctgttgcg tgaaagtggc   1740
agcgacaaga cggtcgatgt ctctgctcct gctactgaag gctggagaaa gatcattgtg   1800
gaacaaggac ctgaagcttt cgcaaaagct gtccgtgctt accctggtgt cttgatcacc   1860
gataccacct ggagagacgc tcatcagagt ttattggcca ctcgtgtgag aaccgtcgat   1920
ctcttacgta tcgcacctgc tacctctcat gctttggcca acgccttttc attggaatgt   1980
tggggaggtg ctacctttga cgttgctatg cgtttccttc atgaagatcc ttgggaccgt   2040
cttgctgctt tgcgaaagtt ggtacccaat gtacccttcc aaatgctttt gcgtggtgcc   2100
aatgcggtag gttacacctc ttaccctgat aatgttatct atgaattctg tgacaaggca   2160
gtcaagtgtg gtatggatgt cttccgtatc tttgattctc tcaattatgt tgaaaacatg   2220
agattgggta ttgacgctgt caagaaggcc ggtggtgttg ttgaagccac catctgttac   2280
actggtgatg tctccaaccc tagccgcaag aagtacgact tgaagtacta ccttgacctt   2340
acacaatcct tggttaacga aggtattcac atcttgggta tcaaggacat ggctggtctt   2400
gtcaaacccc aggcagccaa attagtggtc cccagtatcc gtgccaagtt ccctgacttg   2460
cccattcacg ttcacacaca cgatactgca ggtactggtg ttgctagcat gatggctgct   2520
```

-continued

```
gccgctgctg gtgctgacgt tgttgatgtt gccgttgacg ccatgtccgg tatgacctct   2580

caacccgcta tgggtgccat tgtcgctgga cttgaacaga ccaatttggg taccggtatc   2640

cgcatggaag acattcatgc catcaatgct tactgggagc aatgtcgttt gctttactct   2700

tgcttcgaag ccaacgtgcg ttcagccgat tctggtgtct atgaacatga aatgcctggt   2760

ggacaatata ccaacttgat gttccaagca caacaactcg gcttgggaac tcaatggaag   2820

caaatcaaga aggcttataa ggaggcaaac gaactctgtg gtgacttggt caaggtcacg   2880

ccttcgtcca aggtcgttgg tgatcttgct caattcatgg tttccaacca actttctgcc   2940

aaagaatttg aagaacgcgc ctctagtctc tctctcccta cctctgtcat cgagttcttc   3000

caaggttatc tcggtcaacc ctatggtggt ttccccgagc ccttgcgctc caacatcctt   3060

cgtgatctac ctcgcctcga cggtcgccct ggtgctagct tgccttcact tgacatggct   3120

aaactcaagg aagagttggt tgaaaagtac ggttcaagta tccgtgatta cgatgtgatc   3180

tctgctgctc tttaccccaa ggtctttgcc gaataccgtg ataccgtcag tcaatacggt   3240

gatctctccg ttttgcctac acgttacttt ttgactaagc ctgagatcaa tgaagaattc   3300

catgttgaga ttgaagaagg aaagacgttg attataaagt tattggccgt tggtcctctg   3360

aacaatgacg gtaaacgtga tgtttacttt gaattgaacg gtgaagctcg tgtagtgggt   3420

attgtcgatc gcaattctgc tattgaaatc gtcacacgtg aaaaggcaaa tccctctaac   3480

cccggtgaca ttggtgctcc tatgtctggt gttgttgttg agatccgtgc caaggaaggt   3540

acccatgtta aggctggcga tcctcttgct gttctctctg ctatgaaaat ggaaacagtg   3600

gtcactgctc ccgtggctgg taaagttgag cgtgttccca tccaagaagg tgattcgtta   3660

tccgctggtg atttggtggc taaggttgtc aaagaggaag cctaaaaaag gaaatttctt   3720

tttcccctca tctgaatttt ttttttctg tagaataata ataaaataag ctaaaaaaat   3780

actttgttat cttatcaaaa aaaaaaaaaa aaaaaaaaaa aaaaaaaaat ttcccactct   3840

cgtcctgttg gtt                                                      3853
```

<210> SEQ ID NO 7
<211> LENGTH: 3857
<212> TYPE: DNA
<213> ORGANISM: Rhizopus oryzae

<400> SEQUENCE: 7

```
ggacactgac atggactgaa cgagtagaaa cgactggagc ttttggacac tgacatggac     60

tgaaggagta gaaacgactg gagcacgagg acactgacat ggactgaagg agtagaaaat    120

ttctttcttg tatttttttt taaacacaca cacacttaaa taataacgat gcctgctgca    180

ccagtacgtg aacattcagt ggataccatt cgcagaaata gcgaagtgat gggtaacctg    240

agaaaattga tggtggttaa tcgtggtgaa attgctatac gtgtctttcg tacagctcat    300

gaactctcta tgaagacagt agctattttc tctcatgaag atagattatc tatgcacaga    360

tataaggctg atgaatccta tcaactcggt cgtattggtc aatacacacc tgtaggtgat    420

tatttggcac aagatgaagt cgttcgaatc gcaaaggaac gtggtgttag catgattcat    480

cctggttatg gtttcttatc tgaaaatgct gaattcgctc gcaaggtgga agctgcagga    540

gtcactttca ttggtccctc tcctgatgtc attgaaagtt taggcgataa aacaaaagcc    600

agaacgattg ccatgcagtg tgaagtccct gttgtccctg gtacacctgg accagtcagt    660

gaatataaag aggccctgaa ctttatcaaa gaatatggtt ttcctattat catcaaggct    720

gccatgggtg gtggtggtcg tggtatgcgt gtggttcgtg acgaagccag tctagaggac    780
```

-continued

```
gcgtttaccc gtgcgaaatc tgaagcttta gctgcctttg gtgatggtac tgtcttcatc    840
gaacgtttcc ttgataagcc tcgtcatatt gaggttcaat tgttggcaga tcgtgcaggt    900
aacgtagtcc atctctttga acgtgattgg tctgtgcaac gtcgtcacca aaaggtcgta    960
aaaattgcac ctgccaaaaa cttggataac aaggtacgtg aggccatctt gaacgatgcg   1020
atcaagattg ccaaggctgt aaagtacaag aacgctggta ctgcagaatt cttggttgat   1080
aaccaaaacc gtcactactt tatcgaaatc aatcctcgta tccaagtcga acacaccatc   1140
acagaagaaa tcacaggtat cgatatcgtt gccgctcaaa ttcagatcgc tgctggtgcc   1200
ctcttgcctc aattgggtct tacccaacaa cgtatccgtc aacgtgggtt cgcgatccag   1260
tgtcgtgtga caaccgagga ccccgaaaag aatttccagc ctgacacggg taagatcgaa   1320
gtttaccgtt cctctggtgg taacggtgtt cgtctggatg gtggtgctgg ttacgcaggt   1380
gctatcatta cccctcatta tgattcactt ttggtcaaag tctcttgttc tggatccacc   1440
tacgaagtcg ctcgtcgaaa gatcgttcgt gccttggtcg aattcagaat tcgtggcgtc   1500
aagaccaata tcccctctt acaacgtctc ttgacccatg atactttcat caacggtaac   1560
tgctggacaa ctttcattga tgatactccc gatcttttcc gtcttgttca attccaaaac   1620
cgtgctcaaa gacttttggg ttaccttggt gatgtcgtcg tcaatggttc tcaaatcaag   1680
ggtcaaatgg gtgatcctat tctgaacaag agatcgaaat tcctgttgcg tgaaagtggc   1740
agcgacaaga cggtcgatgt ctctgctcct gctactgaag gctggagaaa gatcattgtg   1800
gaacaaggac ctgaagcttt cgcaaaagct gtccgtgctt accctggtgt cttgatcacc   1860
gataccacct ggagagacgc tcatcagagt ttattggcca ctcgtgtgag aaccgtcggt   1920
aagttgtaaa aaaaaagtgg tatgattttt tattgatttt tttttttttt tttgaaaaga   1980
tctcttacgt atcgcacctg ctacctctca tgctttggcc aacgcctttt cattggaatg   2040
ttggggaggt gctacctttg acgttgctat gcgtttcctt catgaagatc cttgggaccg   2100
tcttgctgct ttgcgaaagt tggtacccaa tgtacccttc caaatgcttt tgcgtggtgc   2160
caatgcggta ggttacacct cttaccctga taatgttatc tatgaattct gtgacaaggc   2220
agtcaagtgt ggtatggatg tcttccgtat ctttgattct ctcaattatg ttgaaaacat   2280
gagattgggt attgacgctg tcaagaaggc cggtggtgtt gttgaagcca ccatctgtta   2340
cactggtgat gtctccaacc ctagccgcaa gaagtacgac ttgaagtact accttgacct   2400
tacacaatcc ttggttaacg aaggtattca catcttgggt atcaaggaca tggctggtct   2460
tgtcaaaccc caggcagcca aattagtggt ccccagtatc cgtgccaagt tccctgactt   2520
gcccattcac gttcacacac acgatactgc aggtactggt gttgctagca tgatggctgc   2580
tgccgctgct ggtgctgacg ttgttgatgt tgccgttgac gccatgtccg gtatgacctc   2640
tcaacccgct atgggtgcca ttgtcgctgg acttgaacag accaatttgg gtaccggtat   2700
ccgcatggaa gacattcatg ccatcaatgc ttactgggag caatgtcgtt tgctttactc   2760
ttgcttcgaa gccaacgtgc gttcagccga ttctggtgtc tatgaacatg aaatgcctgg   2820
tggacaatat accaacttga tgttccaagc acaacaactc ggcttgggaa ctcaatggaa   2880
gcaaatcaag aaggcttata aggaggcaaa cgaactctgt ggtgacttgg tcaaggtcac   2940
gccttcgtcc aaggtcgttg gtgatcttgc tcaattcatg gtttccaacc aactttctgc   3000
caaagaattt gaagaacgcg cctctagtct ctctctccct acctctgtca tcgagttctt   3060
ccaaggttat ctcggtcaac cctatggtgg tttccccgag cccttgcgct ccaacatcct   3120
```

-continued

```
tcgtgatcta cctcgcctcg acggtcgccc tggtgctagc ttgccttcac ttgacatggc   3180

taaactcaag gaagagttgg ttgaaaagta cggttcaagt atccgtgatt acgatgtgat   3240

ctctgctgct ctttacccca aggtctttgc cgaataccgt gataccgtca gtcaatacgg   3300

tgatctctcc gttttgccta cacgttactt tttgactaag cctgagatca atgaagaatt   3360

ccatgttgag attgaagaag gaaagacgtt gattataaag ttattggccg ttggtcctct   3420

gaacaatgac ggtaaacgtg atgtttactt tgaattgaac ggtgaagctc gtgtagtggg   3480

tattgtcgat cgcaattctg ctattgaaat cgtcacacgt gaaaaggcaa atccctctaa   3540

ccccggtgac attggtgctc ctatgtctgg tgttgttgtt gagatccgtg ccaaggaagg   3600

tacccatgtt aaggctggcg atcctcttgc tgttctctct gctatgaaaa tggaaacagt   3660

ggtcactgct cccgtggctg gtaaagttga gcgtgttccc atccaagaag gtgattcgtt   3720

atccgctggt gatttggtgg ctaaggttgt caaagaggaa gcctaaaaaa ggaaatttct   3780

ttttcccctc atctgaattt tttttttct gtagaataat aataaaataa gctaaaaaaa   3840

tactttgtta tcttatc                                                  3857
```

<210> SEQ ID NO 8
<211> LENGTH: 1216
<212> TYPE: PRT
<213> ORGANISM: Rhizopus oryzae

<400> SEQUENCE: 8

```
Met Pro Ala Ala Pro Val Arg Glu His Ser Val Asp Thr Ile Arg Arg
1               5                   10                  15

Asn Ser Glu Val Met Gly Asn Leu Arg Lys Leu Met Val Val Asn Arg
            20                  25                  30

Gly Glu Ile Ala Ile Arg Val Phe Arg Thr Ala His Glu Leu Ser Met
        35                  40                  45

Lys Thr Val Ala Ile Phe Ser His Glu Asp Arg Leu Ser Met His Arg
    50                  55                  60

Tyr Lys Ala Asp Glu Ser Tyr Gln Leu Gly Arg Ile Gly Gln Tyr Thr
65                  70                  75                  80

Pro Val Gly Asp Tyr Leu Ala Gln Asp Glu Val Val Arg Ile Ala Lys
                85                  90                  95

Glu Arg Gly Val Ser Met Ile His Pro Gly Tyr Gly Phe Leu Ser Glu
            100                 105                 110

Asn Ala Glu Phe Ala Arg Lys Val Glu Ala Ala Gly Val Thr Phe Ile
        115                 120                 125

Gly Pro Ser Pro Asp Val Ile Glu Ser Leu Gly Asp Lys Thr Lys Ala
    130                 135                 140

Arg Thr Ile Ala Met Gln Cys Glu Val Pro Val Val Pro Gly Thr Pro
145                 150                 155                 160

Gly Pro Val Ser Glu Tyr Lys Glu Ala Leu Asn Phe Ile Lys Glu Tyr
                165                 170                 175

Gly Phe Pro Ile Ile Ile Lys Ala Ala Met Gly Gly Gly Gly Arg Gly
            180                 185                 190

Met Arg Val Val Arg Asp Glu Ala Ser Leu Glu Asp Ala Phe Thr Arg
        195                 200                 205

Ala Lys Ser Glu Ala Leu Ala Ala Phe Gly Asp Gly Thr Val Phe Ile
    210                 215                 220

Glu Arg Phe Leu Asp Lys Pro Arg His Ile Glu Val Gln Leu Leu Ala
225                 230                 235                 240
```

-continued

```
Asp Arg Ala Gly Asn Val Val His Leu Phe Glu Arg Asp Trp Ser Val
                245                 250                 255

Gln Arg Arg His Gln Lys Val Val Lys Ile Ala Pro Ala Lys Asn Leu
            260                 265                 270

Asp Asn Lys Val Arg Glu Ala Ile Leu Asn Asp Ala Ile Lys Ile Ala
        275                 280                 285

Lys Ala Val Lys Tyr Lys Asn Ala Gly Thr Ala Glu Phe Leu Val Asp
    290                 295                 300

Asn Gln Asn Arg His Tyr Phe Ile Glu Ile Asn Pro Arg Ile Gln Val
305                 310                 315                 320

Glu His Thr Ile Thr Glu Glu Ile Thr Gly Ile Asp Ile Val Ala Ala
                325                 330                 335

Gln Ile Gln Ile Ala Ala Gly Ala Leu Leu Pro Gln Leu Gly Leu Thr
            340                 345                 350

Gln Gln Arg Ile Arg Gln Arg Gly Phe Ala Ile Gln Cys Arg Val Thr
        355                 360                 365

Thr Glu Asp Pro Glu Lys Asn Phe Gln Pro Asp Thr Gly Lys Ile Glu
    370                 375                 380

Val Tyr Arg Ser Ser Gly Gly Asn Gly Val Arg Leu Asp Gly Gly Ala
385                 390                 395                 400

Gly Tyr Ala Gly Ala Ile Ile Thr Pro His Tyr Asp Ser Leu Leu Val
                405                 410                 415

Lys Val Ser Cys Ser Gly Ser Thr Tyr Glu Val Ala Arg Arg Lys Ile
            420                 425                 430

Val Arg Ala Leu Val Glu Phe Arg Ile Arg Gly Val Lys Thr Asn Ile
        435                 440                 445

Pro Phe Leu Gln Arg Leu Leu Thr His Asp Thr Phe Ile Asn Gly Asn
    450                 455                 460

Cys Trp Thr Thr Phe Ile Asp Asp Thr Pro Asp Leu Phe Arg Leu Val
465                 470                 475                 480

Gln Phe Gln Asn Arg Ala Gln Arg Leu Leu Gly Tyr Leu Gly Asp Val
                485                 490                 495

Val Val Asn Gly Ser Gln Ile Lys Gly Gln Met Gly Asp Pro Ile Leu
            500                 505                 510

Asn Lys Arg Ser Lys Phe Leu Leu Arg Glu Ser Gly Ser Asp Lys Thr
        515                 520                 525

Val Asp Val Ser Ala Pro Ala Thr Glu Gly Trp Arg Lys Ile Ile Val
    530                 535                 540

Glu Gln Gly Pro Glu Ala Phe Ala Lys Ala Val Arg Ala Tyr Pro Gly
545                 550                 555                 560

Val Leu Ile Thr Asp Thr Thr Trp Arg Asp Ala His Gln Ser Leu Leu
                565                 570                 575

Ala Thr Arg Val Arg Thr Val Asp Leu Leu Arg Ile Ala Pro Ala Thr
            580                 585                 590

Ser His Ala Leu Ala Asn Ala Phe Ser Leu Glu Cys Trp Gly Gly Ala
        595                 600                 605

Thr Phe Asp Val Ala Met Arg Phe Leu His Glu Asp Pro Trp Asp Arg
    610                 615                 620

Leu Ala Ala Leu Arg Lys Leu Val Pro Asn Val Pro Phe Gln Met Leu
625                 630                 635                 640

Leu Arg Gly Ala Asn Ala Val Gly Tyr Thr Ser Tyr Pro Asp Asn Val
                645                 650                 655

Ile Tyr Glu Phe Cys Asp Lys Ala Val Lys Cys Gly Met Asp Val Phe
```

-continued

```
            660                 665                 670

Arg Ile Phe Asp Ser Leu Asn Tyr Val Glu Asn Met Arg Leu Gly Ile
        675                 680                 685

Asp Ala Val Lys Lys Ala Gly Gly Val Val Glu Ala Thr Ile Cys Tyr
    690                 695                 700

Thr Gly Asp Val Ser Asn Pro Ser Arg Lys Lys Tyr Asp Leu Lys Tyr
705                 710                 715                 720

Tyr Leu Asp Leu Thr Gln Ser Leu Val Asn Glu Gly Ile His Ile Leu
                725                 730                 735

Gly Ile Lys Asp Met Ala Gly Leu Val Lys Pro Gln Ala Ala Lys Leu
            740                 745                 750

Val Val Pro Ser Ile Arg Ala Lys Phe Pro Asp Leu Pro Ile His Val
        755                 760                 765

His Thr His Asp Thr Ala Gly Thr Gly Val Ala Ser Met Met Ala Ala
    770                 775                 780

Ala Ala Ala Gly Ala Asp Val Val Asp Val Ala Val Asp Ala Met Ser
785                 790                 795                 800

Gly Met Thr Ser Gln Pro Ala Met Gly Ala Ile Val Ala Gly Leu Glu
                805                 810                 815

Gln Thr Asn Leu Gly Thr Gly Ile Arg Met Glu Asp Ile His Ala Ile
            820                 825                 830

Asn Ala Tyr Trp Glu Gln Cys Arg Leu Leu Tyr Ser Cys Phe Glu Ala
        835                 840                 845

Asn Val Arg Ser Ala Asp Ser Gly Val Tyr Glu His Glu Met Pro Gly
    850                 855                 860

Gly Gln Tyr Thr Asn Leu Met Phe Gln Ala Gln Gln Leu Gly Leu Gly
865                 870                 875                 880

Thr Gln Trp Lys Gln Ile Lys Lys Ala Tyr Lys Glu Ala Asn Glu Leu
                885                 890                 895

Cys Gly Asp Leu Val Lys Val Thr Pro Ser Ser Lys Val Val Gly Asp
            900                 905                 910

Leu Ala Gln Phe Met Val Ser Asn Gln Leu Ser Ala Lys Glu Phe Glu
        915                 920                 925

Glu Arg Ala Ser Ser Leu Ser Leu Pro Thr Ser Val Ile Glu Phe Phe
    930                 935                 940

Gln Gly Tyr Leu Gly Gln Pro Tyr Gly Gly Phe Pro Glu Pro Leu Arg
945                 950                 955                 960

Ser Asn Ile Leu Arg Asp Leu Pro Arg Leu Asp Gly Arg Pro Gly Ala
                965                 970                 975

Ser Leu Pro Ser Leu Asp Met Ala Lys Leu Lys Glu Glu Leu Val Glu
            980                 985                 990

Lys Tyr Gly Ser Ser Ile Arg Asp  Tyr Asp Val Ile Ser  Ala Ala Leu
        995                 1000                1005

Tyr Pro  Lys Val Phe Ala Glu  Tyr Arg Asp Thr Val  Ser Gln Tyr
    1010                1015                1020

Gly Asp  Leu Ser Val Leu Pro  Thr Arg Tyr Phe Leu  Thr Lys Pro
    1025                1030                1035

Glu Ile  Asn Glu Glu Phe His  Val Glu Ile Glu Glu  Gly Lys Thr
    1040                1045                1050

Leu Ile  Ile Lys Leu Leu Ala  Val Gly Pro Leu Asn  Asn Asp Gly
    1055                1060                1065

Lys Arg  Asp Val Tyr Phe Glu  Leu Asn Gly Glu Ala  Arg Val Val
    1070                1075                1080
```

```
Gly Ile  Val Asp Arg Asn Ser  Ala Ile Glu Ile Val  Thr Arg Glu
    1085                 1090                 1095

Lys Ala  Asn Pro Ser Asn Pro  Gly Asp Ile Gly Ala  Pro Met Ser
    1100                 1105                 1110

Gly Val  Val Val Glu Ile Arg  Ala Lys Glu Gly Thr  His Val Lys
    1115                 1120                 1125

Ala Gly  Asp Pro Leu Ala Val  Leu Ser Ala Met Lys  Met Glu Thr
    1130                 1135                 1140

Val Val  Thr Ala Pro Val Ala  Gly Lys Val Glu Arg  Val Pro Ile
    1145                 1150                 1155

Gln Glu  Gly Asp Ser Leu Ser  Ala Gly Asp Leu Val  Ala Lys Val
    1160                 1165                 1170

Val Lys  Glu Glu Ala Met Glu  Thr Val Val Thr Ala  Pro Val Ala
    1175                 1180                 1185

Gly Lys  Val Glu Arg Val Pro  Ile Gln Glu Gly Asp  Ser Leu Ser
    1190                 1195                 1200

Ala Gly  Asp Leu Val Ala Lys  Val Val Lys Glu Glu  Ala
    1205                 1210                 1215


<210> SEQ ID NO 9
<211> LENGTH: 2901
<212> TYPE: DNA
<213> ORGANISM: Medicago sativa

<400> SEQUENCE: 9

atggcaaaca agatggaaaa aatggcatca attgatgcac agcttagaca attggttcct     60

gcaaaagtga gtgaagatga taaacttatt gagtatgatg ctttgttgtt ggatcggttt    120

cttgatattc ttcaagattt acatggagag gatctgaagg attctgttca agaagtgtat    180

gaactgtctg ctgaatatga aagaaagcat gatcctaaga aacttgaaga gcttggaaat    240

ttgatcacaa gtttcgatgc aggtgactca attgttgttg ccaagtcctt ttcacacatg    300

cttaacttgg ccaacttagc tgaagaggtt caaattgcgc accgccgaag gaacaagttg    360

aagaaaggtg attttaggga tgagagcaat gcaaccactg aatctgacat tgaggaaact    420

ctcaagaaac ttgtgtttga catgaagaaa tctcctcaag aggtttttga tgcattgaag    480

aaccagactg ttgatcttgt tcttactgct catcctactc agtcggttcg tcgatctttg    540

cttcaaaagc acggaagggt aaggaactgt ttatctcaat tgtatgctaa agacatcact    600

cctgatgata agcaggagct tgatgaagct ctccagaggg agattcaagc tgcattccgt    660

actgacgaaa tcaagaggac tccaccaact ccccaagatg aaatgagagc tgggatgagt    720

tacttccatg aaacaatttg gaagggtgtc cctaaatttc ttcgccgtgt tgatacggca    780

ttgaagaaca tagggattaa cgaacgtgtt ccctataatg ctcctcttat tcaattttct    840

tcttggatgg gtggtgatcg tgacggtaat ccaagagtga ctcctgaagt gacaagggat    900

gtttgcttac tagctagaat gatggctgct aacttgtatt attcacagat agaagatctt    960

atgtttgaac tttctatgtg gcgttgcaat gacgagctac gtgttcgcgc agaagaactt   1020

cacaggaatt ccaagaaaga tgaagttgca aaacactata tagagttttg gaaaaaaatt   1080

cctttgaatg aaccataccg tgttgtactc ggggaggtaa gggacaagct ctatcgcact   1140

cgtgagcgtt ctcgttatct cctagctcat ggctactgtg aaattcctga agaagccaca   1200

ttcaccaatg tcgatgagtt tctggaacct cttgaactct gctacagatc actctgtgct   1260

tgtggtgatc gtgcaattgc tgatggaagc cttcttgatt tcttgaggca agtttccact   1320
```

-continued

```
tttggactgt cacttgtaag gcttgatata cggcaagagt ctgatcgtca cactgacgtg   1380

atggatgcca ttaccaaaca tttggaaatt ggatcctacc aagaatggtc tgaagaaaaa   1440

agacaggaat ggcttttgtc cgagttgatt ggcaaaaggc cactctttgg acctgaccta   1500

ccccaaaccg atgaaattag agatgtttta gacacgttcc gtgtcatagc agaacttcca   1560

tctgacaact ttggagccta catcatttcg atggcaactg caccgtctga tgtgctggca   1620

gttgagcttc ttcaacgtga atgcaaagtc aggaatccat taagagtcgt tccgttgttt   1680

gaaaagcttg atgatcttga gtctgctcct gctgcattgg ctcggttgtt ctccatagac   1740

tggtacatta accggatcga tgggaagcaa gaagttatga ttggatattc tgattcagga   1800

aaagatgctg gaaggttttc tgcagcatgg cagctatata aggctcagga ggacctcatc   1860

aaagtcgcac agaaatttgg tgttaagcta accatgttcc acggtcgtgg tggaactgtt   1920

ggaagaggag gtggacctac ccatcttgct atcttgtctc aaccaccaga aacaattcac   1980

ggatctcttc gtgtgacagt tcaaggtgaa gttattgaac agtcgttcgg tgaggaacac   2040

ttgtgcttta ggacactgca acgtttcact gctgctactc tagaacatgg aatgcgtccc   2100

ccaagctctc caaaaccaga atggcgcgcc ttgatggatc agatggctgt cattgcaact   2160

gaggaatacc gttcaattgt gttcaaggaa ccacgttttg ttgagtattt ccgtctggct   2220

acaccagaga tggagtatgg taggatgaac attggaagtc gaccggcaaa gagaaggcct   2280

agtggaggca ttgaaacact gcgtgcgata ccatggatct ttgcctggac acagacaagg   2340

tttcatcttc cagtatggct gggctttgga gcagcattta gacaagttgt tcagaaggat   2400

gttaagaatc tccatatgct gcaagagatg tacaatcaat ggcctttctt tagggttaca   2460

attgatttag ttgaaatggt gtttgccaag ggtgaccctg gtattgcagc actgaatgat   2520

aggctcctag tttcaaagga tctgtggcca tttggggaac aattgagaag caaatatgaa   2580

gaaactaaga aactcctact tcaggtggct gcacacaagg aagttcttga aggtgacccc   2640

tacttgaagc aaagactcag actccgtgat tcgtacatta caacccttaa tgttttccaa   2700

gcctacacat tgaaacggat ccgcgatcca aactacaagg tggaggtgcg ccccccaata   2760

tcgaaagagt ctgctgaaac aagtaaacca gctgatgaac ttgtaacatt gaatccaaca   2820

agtgaatatg ctcctggttt ggaagacaca ctcattctta ccatgaaggg tattgctgct   2880

ggcatgcaga acactggtta a                                             2901
```

```
<210> SEQ ID NO 10
<211> LENGTH: 1639
<212> TYPE: DNA
<213> ORGANISM: Rhizopus oryzae
<220> FEATURE:
<221> NAME/KEY: rRNA
<222> LOCATION: (1)..(46)
<223> OTHER INFORMATION: Partial 5s encoding flanking sequence
<220> FEATURE:
<221> NAME/KEY: promoter
<222> LOCATION: (47)..(901)
<220> FEATURE:
<221> NAME/KEY: rRNA
<222> LOCATION: (902)..(1617)
<223> OTHER INFORMATION: Transcription start point; start of 5' ETS and
      beginning of 35s pre-mRNA
<220> FEATURE:
<221> NAME/KEY: misc_feature
<222> LOCATION: (1422)..(1444)
<223> OTHER INFORMATION: Region of 50% homology to the U3 sno-RNA
      binding site of Ashbya gossypii
<220> FEATURE:
<221> NAME/KEY: rRNA
```

-continued

<222> LOCATION: (1618)..(1630)
<223> OTHER INFORMATION: 18s rRNA encoding region

<400> SEQUENCE: 10
gggggaccac atgggaatac tggttgctgt agttttgctt ttttttactt tttttttact 60 ttttttttt tttactttac tttaaatgtt tccttaacag ctctaaaaca atcttagaac 120
aatttaatat atcttttttt tttttttttg catataaaat ataggcttaa aatgacctat 180
attgattgta aactatgata tagttcacta gtagtaagca tgccaaagat gaataaaaaa 240
gaatatgtgt ttaaaaaaat tcgaaaatca tatttttttt tacatgtaaa agatagttaa 300
aaatgggggg ttttttttat ttttattttt tttacatata aaacataggc ttaaaatgac 360
ctgtattgat tgtaaactat aatatagttc actagcagta cgcatgccaa agataagtaa 420
aaaagaatat gtgtttaaaa aagttcgaaa attatatttt ttttttttac atgtaaaaga 480
tagccttaaa atggggatta ttttttattt ttttttttac atataaaaca taggcttaaa 540
atgacctata ttgatcaagg attatagtaa agtacatttg taataggtaa ggtggctaag 600
attttaaaaa aaaagcctac ttaaaaattc caaaaaatag tttttttttt ttacatataa 660
attgtatctc caaaatgatt taaattgatc aaggactaca tcaaagtaca ttaacaataa 720
gtagggtaag taaagttaca aaagaaagcg catttaaaat gactaagaat ccatcactaa 780
gaatttatca ctaaaattta ccaagtgcat atctgggatt aaaattgaat caccgatttc 840
atctcaaact ctatgaaaaa acaccttaaa ttctaaataa ctctatgaaa acttatccaa 900
aatgaacaag caatacgtag aattgtagaa aaaaaaatta ggtttttgac tatattttcg 960
gatttttgct aagtcatttt tggctgagat aaatttagtt ttgtccaaac cttgattttt 1020
ttttttcgga ccgatgattt tactaaaaaa taaataatca atgtccggat agcacatatt 1080
gaacctcatg gaaggcgaaa acgaaagttt gagcttttca cacatcgagg ctgtgagtct 1140
tggataacct atggtagaaa ggaaatatct tttctactgt taaagttccc ggattaaatc 1200
ttgtcgtaca cttccttatg ggagcagatg ggcgagtcgc tggctcctgc ggaagctctt 1260
tgagttaccg tagtgagaaa agatggggat tgtatattat tacctatcca ggtatgatta 1320
caagccaact cctgggcacc tttattggag tccatcgact gatctgctgg gaaaaattta 1380
tttttctttg cgttgatcgg acgaaaactg taggattgct aaagggaaat taaagtagat 1440
tgtgcaaacg ttcagcagat atgcagaatg tagtatgatc tgctttctct ttcaaagggt 1500
ttatcccctt tgggtagtcg actggtacgc catggaaaaa aagtgggctc ttctttgaag 1560
agtctcgtct aagctttcga gtttaggcta actttttaac ctgatagtta cctggttgat 1620
cctgccaaca tgacctgca 1639

<210> SEQ ID NO 11
<211> LENGTH: 855
<212> TYPE: DNA
<213> ORGANISM: Rhizopus oryzae

<400> SEQUENCE: 11 acttttttt tactttttt ttttttact ttactttaaa tgtttcctta acagctctaa 60
aacaatctta gaacaattta atatatcttt tttttttttt tttgcatata aaatataggc 120
ttaaaatgac ctatattgat tgtaaactat gatatagttc actagtagta agcatgccaa 180
agatgaataa aaaagaatat gtgtttaaaa aaattcgaaa atcatatttt tttttacatg 240
taaaagatag ttaaaaatgg ggggtttttt ttatttttat ttttttttaca tataaaacat 300

-continued

```
aggcttaaaa tgacctgtat tgattgtaaa ctataatata gttcactagc agtacgcatg    360

ccaaagataa gtaaaaaaga atatgtgttt aaaaaagttc gaaaattata tttttttttt    420

ttacatgtaa aagatagcct taaaatgggg attatttttt attttttttt ttacatataa    480

aacataggct taaaatgacc tatattgatc aaggattata gtaaagtaca tttgtaatag    540

gtaaggtggc taagatttta aaaaaaaagc ctacttaaaa attccaaaaa atagtttttt    600

ttttttacat ataaattgta tctccaaaat gatttaaatt gatcaaggac tacatcaaag    660

tacattaaca ataagtaggg taagtaaagt tacaaaagaa agcgcattta aaatgactaa    720

gaatccatca ctaagaattt atcactaaaa tttaccaagt gcatatctgg gattaaaatt    780

gaatcaccga tttcatctca aactctatga aaaaacacct taaattctaa ataactctat    840

gaaaacttat ccaaa                                                     855


<210> SEQ ID NO 12
<211> LENGTH: 19
<212> TYPE: RNA
<213> ORGANISM: Rhizopus oryzae

<400> SEQUENCE: 12

cagacgauga ccuuccuua                                                  19


<210> SEQ ID NO 13
<211> LENGTH: 19
<212> TYPE: RNA
<213> ORGANISM: Rhizopus oryzae

<400> SEQUENCE: 13

uaaggaaggu caucgucug                                                  19


<210> SEQ ID NO 14
<211> LENGTH: 19
<212> TYPE: RNA
<213> ORGANISM: Rhizopus oryzae

<400> SEQUENCE: 14

cuuugaugug uucuucaac                                                  19


<210> SEQ ID NO 15
<211> LENGTH: 19
<212> TYPE: RNA
<213> ORGANISM: Rhizopus oryzae

<400> SEQUENCE: 15

guugaagaac acaucaaag                                                  19


<210> SEQ ID NO 16
<211> LENGTH: 34
<212> TYPE: DNA
<213> ORGANISM: Rhizopus oryzae

<400> SEQUENCE: 16

cgttagaacg cgtaatacga ctcactatag ggag                                 34


<210> SEQ ID NO 17
<211> LENGTH: 27
<212> TYPE: DNA
<213> ORGANISM: Rhizopus oryzae

<400> SEQUENCE: 17

gtaatcatgt tcttgatgaa atcacgg                                         27
```

<210> SEQ ID NO 18
<211> LENGTH: 28
<212> TYPE: DNA
<213> ORGANISM: Rhizopus oryzae

<400> SEQUENCE: 18
gattcactga atatgcaatt cacactag 28

<210> SEQ ID NO 19
<211> LENGTH: 20
<212> TYPE: DNA
<213> ORGANISM: Rhizopus oryzae

<400> SEQUENCE: 19
caragragrc aycaraargt 20

<210> SEQ ID NO 20
<211> LENGTH: 20
<212> TYPE: DNA
<213> ORGANISM: Rhizopus oryzae
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 20
tcrtcdatra angtngtcca 20

<210> SEQ ID NO 21
<211> LENGTH: 7
<212> TYPE: PRT
<213> ORGANISM: Rhizopus oryzae

<400> SEQUENCE: 21

Trp Thr Thr Phe Ile Asp Asp
1 5

<210> SEQ ID NO 22
<211> LENGTH: 28
<212> TYPE: DNA
<213> ORGANISM: Rhizopus oryzae

<400> SEQUENCE: 22
ccaatacgac cgagttgata ggattcat 28

<210> SEQ ID NO 23
<211> LENGTH: 23
<212> TYPE: DNA
<213> ORGANISM: Rhizopus oryzae

<400> SEQUENCE: 23
gcatagataa tgtatcttca tga 23

<210> SEQ ID NO 24
<211> LENGTH: 28
<212> TYPE: DNA
<213> ORGANISM: Rhizopus oryzae

<400> SEQUENCE: 24
tcgaattcgg gggaccacat gggaatac 28

<210> SEQ ID NO 25
<211> LENGTH: 26
<212> TYPE: DNA
<213> ORGANISM: Rhizopus oryzae

<400> SEQUENCE: 25
tggctgcagg tcatgttggc aggatc 26

<210> SEQ ID NO 26
<211> LENGTH: 3540
<212> TYPE: DNA
<213> ORGANISM: Rhizopus oryzae

<400> SEQUENCE: 26
atgcctgctg caccagtacg tgaacactct gtggatacca ttcgtagaaa tagcgaagtg 60
atgggtaacc tgagaaaatt gatggtggtt aatcgtggtg aaattgctat ccgtgtcttt 120
cgtacagctc atgaactctc tatgaagaca gtagctattt tctctcatga agatagatta 180
tccatgcaca gatataaggc ggatgaatcc tatcaactcg gtcgtattgg tcaatacaca 240
cctgtaggtg cttatctggc acaagatgaa gtcgttcgaa tcgcaaagga acgtggtgtg 300
agcatgattc atcctggtta tggtttcttg tctgaaaatg ctgaattcgc tcgcaaggtg 360
gaagctgcag gaatcacttt cattggtccc tctcctgatg tcattgaaag tttaggcgat 420
aagacaaaag ccagaacgat tgccatgaag tgtgaagtcc ctgttgtccc tggtacacct 480
ggacctgtca gtgaatacaa agaggccctg aactttatca aagaatatgg ttttcctatc 540
atcatcaagg ctgccatggg tggtggtggt cgtggtatgc gtgtggttcg tgacgaagcc 600
agtctagagg acgcgtttac ccgtgcgaaa tctgaagctt tggctgcctt tggtgatggc 660
actgtcttta tcgaacgttt ccttgataag cctcgtcata tcgaggttca attgttggca 720
gatcgtgcag gtaacgtggt ccatctcttt gaacgtgatt gttctgttca gcgtcgtcac 780
caaaaggtgg ttgaaatcgc ccctgccaaa aacttggata acaaggtacg tgaggccatc 840
ttgaacgatg cgatcaagat tgccaaggct gtaaagtaca agaacgcggg tactgcagaa 900
ttcttggtgg ataaccaaaa ccgtcactac tttatcgaaa tcaatcctcg tatccaagtc 960
gaacatacca tcacagaaga aatcacgggt attgatatcg ttgccgctca aattcagatc 1020
gctgccggtg ccctcttgcc tcaattgggt cttacccaac aacgtatccg tcaacgtggg 1080
ttcgcgatcc agtgtcgtgt gacaaccgag gaccccgaaa agaatttcca gcctgacacg 1140
ggtaagatcg aagtgtaccg ttcctctggt ggtaacggtg ttcgtctgga tggtggtgct 1200
ggttacgcag gtgctatcat tacccctcac tatgattcac ttttggtcaa agtctcttgt 1260
tctggatcca cctacgaagt cgctcgtcgc aagatcgtcc gtgccttggt cgaattcaga 1320
atccgtggtg tcaagaccaa tatccccttc ttacaacgtc tcttgaccca tgataccttc 1380
atcaacggta actgctggac aactttcatt gatgatactc ccgatctttt ccgtcttgtt 1440
caattccaaa accgtgctca aagactcttg ggttacctgg gtgatgtcgt cgtcaatggt 1500
tctcaaatca agggtcaaat gggtgatccc attctgaagc aagagatcga aatccccgtg 1560
ttgcgtgaaa gtggtagtga caagacggtc gatgtctctg ctcctgctac ggaaggctgg 1620
agaaagatca ttgtggaaca aggacctgaa gctttcgcaa aagctgtccg tgcttaccct 1680
ggtgtcttga tcaccgatac cacctggaga gacgctcatc agagtttatt ggccactcgt 1740
gtgagaactg tcgatctctt gcgtatcgcc cctgctacct ctcacgcttt ggccaacgcc 1800

-continued

```
ttttcattgg aatgttgggg aggtgctacg tttgatgttg ctatgcgttt ccttcatgaa   1860

gatccttggg accgtcttgc tgctttgcga aagttggtac ccaatgtacc cttccaaatg   1920

cttttgcgtg gtgccaatgc ggtaggttac acctcttacc ctgataacgt tatctatgaa   1980

ttctgtgaca aggcagtcaa gtgtggtatg gatgtcttcc gtatctttga ctctctcaat   2040

tatgttgaaa acatgagatt gggtattgac gctgtcaaga aggccggtgg tgttgttgaa   2100

gccaccatct gttacacggg tgatgtctcc aaccctaacc gcaagaagta cgacttgaag   2160

tactaccttg acctgacaca atccttggtg aacgaaggta ttcacatctt gggtatcaag   2220

gacatggctg gtcttctcaa acccgaggca gccaagttac tggtctccag tatccgtgcc   2280

aagttccccg acttgcccat tcacgttcac acacacgata ccgcaggtac gggtgttgct   2340

agcatgatgg ccgctgccgc tgctggtgct gacattgttg atgttgccgt ggacgccatg   2400

tccggcatga cctctcaacc ggcgatgggt gccattgtcg ctggacttga acagaccaat   2460

ttgggtaccg gtatccgcat ggaagacatt catgccatca attcttactg ggagcaatgc   2520

cgtttgcttt actcttgctt cgaagccaac gtgcgttcgg ccgattcggg tgtctatgaa   2580

catgaaatgc ctggtggaca atataccaac ttgatgttcc aagcccaaca actcggcttg   2640

ggaactcagt ggaagcaaat caagaaggct tacaaggagg ccaacgaact ctgtggtgac   2700

ttggtcaagg tcacgccttc gtccaaggtc gtgggtgatc ttgctcaatt catggtttcc   2760

aaccaactct ctgccaaaga atttgaagaa cgcgcctcga gtctctctct gcccacctct   2820

gtcatcgagt tcttccaagg ttatctcggt caaccctatg gcggtttccc cgagcccttg   2880

cgctccaaca tccttcgtga tctccctcgc ctcgacggtc gccctggtgc tagcctgcct   2940

ccgttggaca tggctaaact caaggaagag ttggttgaaa agtacggttc gagcatccgt   3000

gattacgacg tgatctcggc tgctctttac cccaaggtct ttgccgacta ccgtgatacc   3060

gtcagtcaat acggtgatct ctccgttttg cctacacgct actttttgtc caagcccgag   3120

atcaatgaag aattccatgt ggagattgaa gaaggaaaga cgttgatcat caagttattg   3180

gccgtcggtc ctctgaacaa tgacggtaaa cgtgatgttt actttgaatt gaacggtgaa   3240

gctcgtgtgg tgggcattgt ggatcgcaat tctgctattg aaatcgtcac acgtgaaaag   3300

gccaacccct ccaaccccgg tgacattggt gctcctatgt cgggtgtggt tgtcgagatc   3360

cgtgccaagg aaggtagcca tgtcaaggcc agtgatcctc tggctgttct ctctgctatg   3420

aagatggaaa cagtggtcac tgctcccgtg gctggtagag ttgagcgtgt tgctatccaa   3480

gaaggtgatt cattatccgc tggtgatttg gtggccaagg ttgtcaaaga ggaagcctaa   3540
```

```
<210> SEQ ID NO 27
<211> LENGTH: 1179
<212> TYPE: PRT
<213> ORGANISM: Rhizopus oryzae

<400> SEQUENCE: 27

Met Pro Ala Ala Pro Val Arg Glu His Ser Val Asp Thr Ile Arg Arg
1               5                   10                  15

Asn Ser Glu Val Met Gly Asn Leu Arg Lys Leu Met Val Val Asn Arg
            20                  25                  30

Gly Glu Ile Ala Ile Arg Val Phe Arg Thr Ala His Glu Leu Ser Met
        35                  40                  45

Lys Thr Val Ala Ile Phe Ser His Glu Asp Arg Leu Ser Met His Arg
    50                  55                  60

Tyr Lys Ala Asp Glu Ser Tyr Gln Leu Gly Arg Ile Gly Gln Tyr Thr
```

-continued

```
65                  70                  75                  80

Pro Val Gly Ala Tyr Leu Ala Gln Asp Glu Val Val Arg Ile Ala Lys
                85                  90                  95

Glu Arg Gly Val Ser Met Ile His Pro Gly Tyr Gly Phe Leu Ser Glu
            100                 105                 110

Asn Ala Glu Phe Ala Arg Lys Val Glu Ala Ala Gly Ile Thr Phe Ile
        115                 120                 125

Gly Pro Ser Pro Asp Val Ile Glu Ser Leu Gly Asp Lys Thr Lys Ala
    130                 135                 140

Arg Thr Ile Ala Met Lys Cys Glu Val Pro Val Val Pro Gly Thr Pro
145                 150                 155                 160

Gly Pro Val Ser Glu Tyr Lys Glu Ala Leu Asn Phe Ile Lys Glu Tyr
                165                 170                 175

Gly Phe Pro Ile Ile Ile Lys Ala Ala Met Gly Gly Gly Gly Arg Gly
            180                 185                 190

Met Arg Val Val Arg Asp Glu Ala Ser Leu Glu Asp Ala Phe Thr Arg
        195                 200                 205

Ala Lys Ser Glu Ala Leu Ala Ala Phe Gly Asp Gly Thr Val Phe Ile
    210                 215                 220

Glu Arg Phe Leu Asp Lys Pro Arg His Ile Glu Val Gln Leu Leu Ala
225                 230                 235                 240

Asp Arg Ala Gly Asn Val Val His Leu Phe Glu Arg Asp Cys Ser Val
                245                 250                 255

Gln Arg Arg His Gln Lys Val Val Glu Ile Ala Pro Ala Lys Asn Leu
            260                 265                 270

Asp Asn Lys Val Arg Glu Ala Ile Leu Asn Asp Ala Ile Lys Ile Ala
        275                 280                 285

Lys Ala Val Lys Tyr Lys Asn Ala Gly Thr Ala Glu Phe Leu Val Asp
    290                 295                 300

Asn Gln Asn Arg His Tyr Phe Ile Glu Ile Asn Pro Arg Ile Gln Val
305                 310                 315                 320

Glu His Thr Ile Thr Glu Glu Ile Thr Gly Ile Asp Ile Val Ala Ala
                325                 330                 335

Gln Ile Gln Ile Ala Ala Gly Ala Leu Leu Pro Gln Leu Gly Leu Thr
            340                 345                 350

Gln Gln Arg Ile Arg Gln Arg Gly Phe Ala Ile Gln Cys Arg Val Thr
        355                 360                 365

Thr Glu Asp Pro Glu Lys Asn Phe Gln Pro Asp Thr Gly Lys Ile Glu
    370                 375                 380

Val Tyr Arg Ser Ser Gly Gly Asn Gly Val Arg Leu Asp Gly Gly Ala
385                 390                 395                 400

Gly Tyr Ala Gly Ala Ile Ile Thr Pro His Tyr Asp Ser Leu Leu Val
                405                 410                 415

Lys Val Ser Cys Ser Gly Ser Thr Tyr Glu Val Ala Arg Arg Lys Ile
            420                 425                 430

Val Arg Ala Leu Val Glu Phe Arg Ile Arg Gly Val Lys Thr Asn Ile
        435                 440                 445

Pro Phe Leu Gln Arg Leu Leu Thr His Asp Thr Phe Ile Asn Gly Asn
    450                 455                 460

Cys Trp Thr Thr Phe Ile Asp Asp Thr Pro Asp Leu Phe Arg Leu Val
465                 470                 475                 480

Gln Phe Gln Asn Arg Ala Gln Arg Leu Leu Gly Tyr Leu Gly Asp Val
                485                 490                 495
```

-continued

```
Val Val Asn Gly Ser Gln Ile Lys Gly Gln Met Gly Asp Pro Ile Leu
            500                 505                 510

Lys Gln Glu Ile Glu Ile Pro Val Leu Arg Glu Ser Gly Ser Asp Lys
        515                 520                 525

Thr Val Asp Val Ser Ala Pro Ala Thr Glu Gly Trp Arg Lys Ile Ile
    530                 535                 540

Val Glu Gln Gly Pro Glu Ala Phe Ala Lys Ala Val Arg Ala Tyr Pro
545                 550                 555                 560

Gly Val Leu Ile Thr Asp Thr Thr Trp Arg Asp Ala His Gln Ser Leu
                565                 570                 575

Leu Ala Thr Arg Val Arg Thr Val Asp Leu Leu Arg Ile Ala Pro Ala
            580                 585                 590

Thr Ser His Ala Leu Ala Asn Ala Phe Ser Leu Glu Cys Trp Gly Gly
        595                 600                 605

Ala Thr Phe Asp Val Ala Met Arg Phe Leu His Glu Asp Pro Trp Asp
    610                 615                 620

Arg Leu Ala Ala Leu Arg Lys Leu Val Pro Asn Val Pro Phe Gln Met
625                 630                 635                 640

Leu Leu Arg Gly Ala Asn Ala Val Gly Tyr Thr Ser Tyr Pro Asp Asn
                645                 650                 655

Val Ile Tyr Glu Phe Cys Asp Lys Ala Val Lys Cys Gly Met Asp Val
            660                 665                 670

Phe Arg Ile Phe Asp Ser Leu Asn Tyr Val Glu Asn Met Arg Leu Gly
        675                 680                 685

Ile Asp Ala Val Lys Lys Ala Gly Gly Val Val Glu Ala Thr Ile Cys
    690                 695                 700

Tyr Thr Gly Asp Val Ser Asn Pro Asn Arg Lys Lys Tyr Asp Leu Lys
705                 710                 715                 720

Tyr Tyr Leu Asp Leu Thr Gln Ser Leu Val Asn Glu Gly Ile His Ile
                725                 730                 735

Leu Gly Ile Lys Asp Met Ala Gly Leu Leu Lys Pro Glu Ala Ala Lys
            740                 745                 750

Leu Leu Val Ser Ser Ile Arg Ala Lys Phe Pro Asp Leu Pro Ile His
        755                 760                 765

Val His Thr His Asp Thr Ala Gly Thr Gly Val Ala Ser Met Met Ala
    770                 775                 780

Ala Ala Ala Ala Gly Ala Asp Ile Val Asp Val Ala Val Asp Ala Met
785                 790                 795                 800

Ser Gly Met Thr Ser Gln Pro Ala Met Gly Ala Ile Val Ala Gly Leu
                805                 810                 815

Glu Gln Thr Asn Leu Gly Thr Gly Ile Arg Met Glu Asp Ile His Ala
            820                 825                 830

Ile Asn Ser Tyr Trp Glu Gln Cys Arg Leu Leu Tyr Ser Cys Phe Glu
        835                 840                 845

Ala Asn Val Arg Ser Ala Asp Ser Gly Val Tyr Glu His Glu Met Pro
    850                 855                 860

Gly Gly Gln Tyr Thr Asn Leu Met Phe Gln Ala Gln Gln Leu Gly Leu
865                 870                 875                 880

Gly Thr Gln Trp Lys Gln Ile Lys Lys Ala Tyr Lys Glu Ala Asn Glu
                885                 890                 895

Leu Cys Gly Asp Leu Val Lys Val Thr Pro Ser Ser Lys Val Val Gly
            900                 905                 910
```

-continued

```
Asp Leu Ala Gln Phe Met Val Ser Asn Gln Leu Ser Ala Lys Glu Phe
        915                 920                 925

Glu Glu Arg Ala Ser Ser Leu Ser Leu Pro Thr Ser Val Ile Glu Phe
    930                 935                 940

Phe Gln Gly Tyr Leu Gly Gln Pro Tyr Gly Gly Phe Pro Glu Pro Leu
945                 950                 955                 960

Arg Ser Asn Ile Leu Arg Asp Leu Pro Arg Leu Asp Gly Arg Pro Gly
                965                 970                 975

Ala Ser Leu Pro Pro Leu Asp Met Ala Lys Leu Lys Glu Glu Leu Val
            980                 985                 990

Glu Lys Tyr Gly Ser Ser Ile Arg  Asp Tyr Asp Val Ile  Ser Ala Ala
        995                 1000                 1005

Leu Tyr  Pro Lys Val Phe Ala  Asp Tyr Arg Asp Thr  Val Ser Gln
    1010                 1015                 1020

Tyr Gly  Asp Leu Ser Val Leu  Pro Thr Arg Tyr Phe  Leu Ser Lys
    1025                 1030                 1035

Pro Glu  Ile Asn Glu Glu Phe  His Val Glu Ile Glu  Glu Gly Lys
    1040                 1045                 1050

Thr Leu  Ile Ile Lys Leu Leu  Ala Val Gly Pro Leu  Asn Asn Asp
    1055                 1060                 1065

Gly Lys  Arg Asp Val Tyr Phe  Glu Leu Asn Gly Glu  Ala Arg Val
    1070                 1075                 1080

Val Gly  Ile Val Asp Arg Asn  Ser Ala Ile Glu Ile  Val Thr Arg
    1085                 1090                 1095

Glu Lys  Ala Asn Pro Ser Asn  Pro Gly Asp Ile Gly  Ala Pro Met
    1100                 1105                 1110

Ser Gly  Val Val Val Glu Ile  Arg Ala Lys Glu Gly  Ser His Val
    1115                 1120                 1125

Lys Ala  Ser Asp Pro Leu Ala  Val Leu Ser Ala Met  Lys Met Glu
    1130                 1135                 1140

Thr Val  Val Thr Ala Pro Val  Ala Gly Arg Val Glu  Arg Val Ala
    1145                 1150                 1155

Ile Gln  Glu Gly Asp Ser Leu  Ser Ala Gly Asp Leu  Val Ala Lys
    1160                 1165                 1170

Val Val  Lys Glu Glu Ala
    1175
```

<210> SEQ ID NO 28
<211> LENGTH: 20
<212> TYPE: DNA
<213> ORGANISM: artificial sequence
<220> FEATURE:
<223> OTHER INFORMATION: Primer

<400> SEQUENCE: 28
ataacgatgc ctgctgcacc 20

<210> SEQ ID NO 29
<211> LENGTH: 23
<212> TYPE: DNA
<213> ORGANISM: Artificial sequence
<220> FEATURE:
<223> OTHER INFORMATION: Primer

<400> SEQUENCE: 29
cgctacgtaa cggcatgaca gtg 23

-continued

```
<210> SEQ ID NO 30
<211> LENGTH: 17
<212> TYPE: RNA
<213> ORGANISM: Rhizopus oryzae

<400> SEQUENCE: 30

uuggccacuc gugugag                                                    17


<210> SEQ ID NO 31
<211> LENGTH: 17
<212> TYPE: RNA
<213> ORGANISM: Rhizopus oryzae

<400> SEQUENCE: 31

cucacacgag uggccaa                                                    17
```